US012359345B2

(12) United States Patent
Bradbury et al.

(10) Patent No.: US 12,359,345 B2
(45) Date of Patent: *Jul. 15, 2025

(54) SINGLE DOMAIN ANTIBODY LIBRARIES WITH MAXIMIZED ANTIBODY DEVELOPABILITY CHARACTERISTICS

(71) Applicant: RULES-BASED MEDICINE INC., Austin, TX (US)

(72) Inventors: Andrew Raymon Morton Bradbury, Santa Fe, NM (US); Andre A. Teixeira, Santa Fe, NM (US)

(73) Assignee: Rules Based Medicine Inc., Austin, TX (US)

( * ) Notice: Subject to any disclaimer, the term of this patent is extended or adjusted under 35 U.S.C. 154(b) by 205 days.

This patent is subject to a terminal disclaimer.

(21) Appl. No.: 18/171,063

(22) Filed: Feb. 17, 2023

(65) Prior Publication Data

US 2024/0093179 A1 Mar. 21, 2024

Related U.S. Application Data

(60) Provisional application No. 63/311,438, filed on Feb. 17, 2022.

(51) Int. Cl.

*C40B 50/06* (2006.01)
*C07K 16/00* (2006.01)
*C40B 40/10* (2006.01)

(52) U.S. Cl.

CPC .............. *C40B 40/10* (2013.01); *C07K 16/00* (2013.01); *C07K 2317/569* (2013.01); *C07K 2317/622* (2013.01)

(58) Field of Classification Search

None

See application file for complete search history.

(56) References Cited

U.S. PATENT DOCUMENTS

2021/0214720 A1 7/2021 Bradbury et al.

FOREIGN PATENT DOCUMENTS

WO WO 2021/256524 A1 12/2021

OTHER PUBLICATIONS

Knappik et al. (Feb. 11, 2000) Journal of Molecular Biology vol. 296 pp. 57 to 86 (Year: 2000).*

* cited by examiner

*Primary Examiner* — Christian C Boesen

(74) *Attorney, Agent, or Firm* — Goodwin Procter LLP

(57) ABSTRACT

Described here are VHH antibody libraries with heavy chain variable domains framework scaffolds having complementary determining regions (CDRs) found in naturally-occurring human antibodies, and methods of making such antibody libraries. The antibody libraries are free of members that comprise one or more liabilities affecting one or more features of such members.

5 Claims, 26 Drawing Sheets

Specification includes a Sequence Listing.

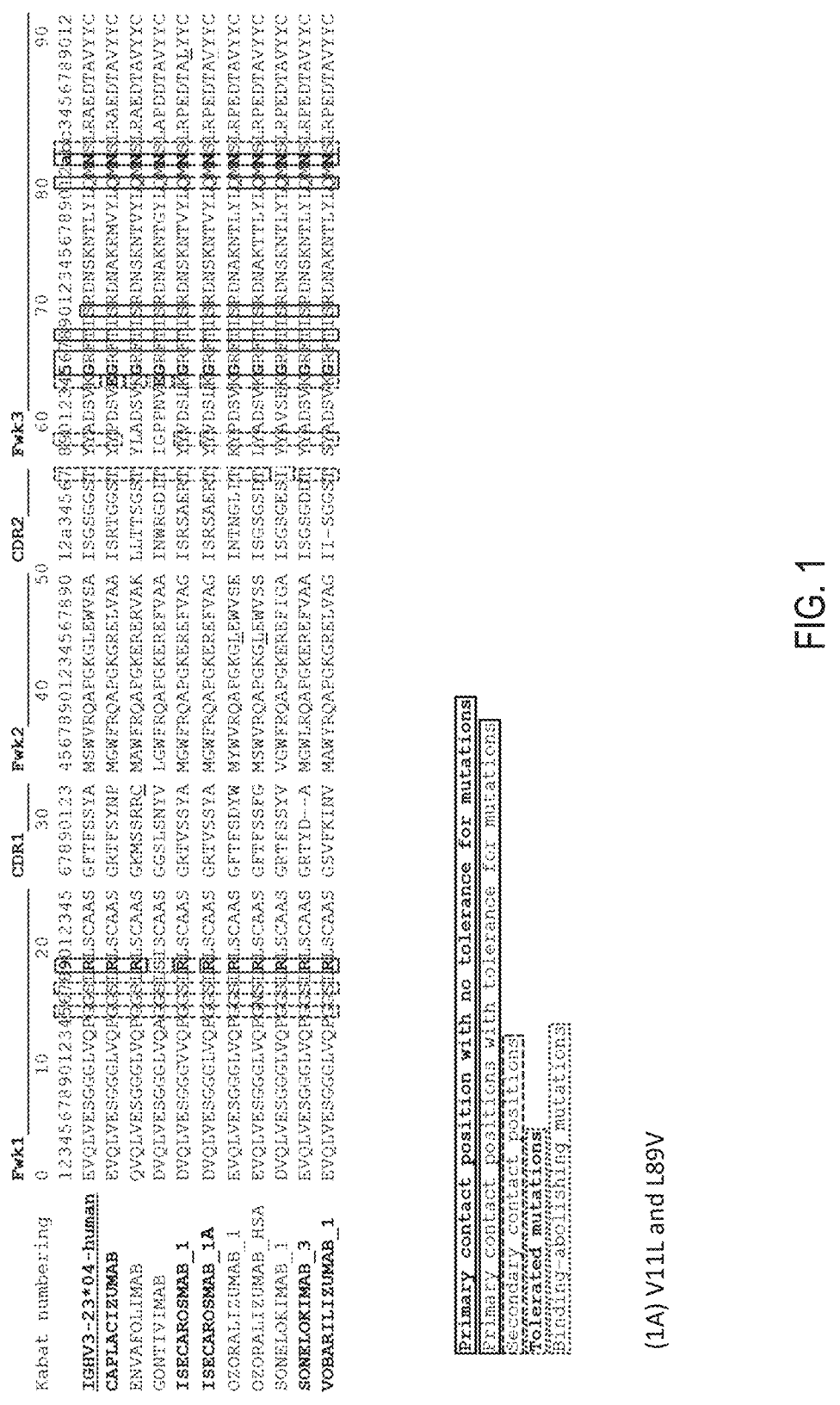

| | Fwk1 | CDR1 | Fwk2 | CDR2 | Fwk3 |
|---|---|---|---|---|---|
| Kabat numbering | 0 10 20 | 30 | 40 50 | | 60 70 80 90 |
| | 1234567890123456789012345 | 67890123 | 45678901234567890 | 12a34567 | 8901234567890123456789012abc3456789012 |
| IGHV3-23*04-human | EVQLVESGGGLVQPGGSLRLSCAAS | GFTFSSYA | MSWVRQAPGKGLEWVSA | ISGSGGST | YYADSVKGRFTISRDNSKNTLYLQMNSLRAEDTAVYYC |
| **CAPLACIZUMAB** | EVQLVESGGGLVQPGGSLRLSCAAS | GRTFSYNP | MGWFRQAPGKGRELVAA | ISRTGGST | YYPDSVEGRFTISRDNAKRMVYLQMNSLRAEDTAVYYC |
| ENVAFOLIMAB | QVQLVESGGGLVQPGGSLRLSCAAS | GKMSSRRC | MAWFRQAPGKERERVAK | LLTTSGST | YLADSVKGRFTISRDNSKNTVYLQMNSLRAEDTAVYYC |
| GONTIVIMAB | DVQLVESGGGLVQAGGSLSLSCAAS | GGSLSNYV | LGWFRQAPGKEREFVAA | INWRGDIT | IGPPNVEGRFTISRDNAKNTGYLQMNSLAPDDTAVYYC |
| **ISECAROSMAB_1** | DVQLVESGGGVVQPGGSLRLSCAAS | GRTVSSYA | MGWFRQAPGKEREFVAG | ISRSAERT | YYVDSLKGRFTISRDNSKNTVYLQMNSLRPEDTALYYC |
| **ISECAROSMAB_1A** | DVQLVESGGGLVQPGGSLRLSCAAS | GRTVSSYA | MGWFRQAPGKEREFVAG | ISRSAERT | YYVDSLKGRFTISRDNSKNTVYLQMNSLRPEDTAVYYC |
| OZORALIZUMAB_1 | EVQLVESGGGLVQPGGSLRLSCAAS | GFTFSDYW | MYWVRQAPGKGLEWVSE | INTNGLIT | KYPDSVKGRFTISPDNAKNTLYLQMNSLRPEDTAVYYC |
| OZORALIZUMAB_HSA | EVQLVESGGGLVQPGNSLRLSCAAS | GFTFSSFG | MSWVRQAPGKGLEWVSS | ISGSGSDT | LYADSVKGRFTISRDNAKTTLYLQMNSLRPEDTAVYYC |
| SONELOKIMAB_1 | DVQLVESGGGLVQPGGSLRLSCAAS | GRTFSSYV | VGWFRQAPGKEREFIGA | ISGSGESI | YYAVSEKGRFTISRDNSKNTLYLQMNSLRPEDTAVYYC |
| **SONELOKIMAB_3** | EVQLVESGGGLVQPGGSLRLSCAAS | GRTYD--A | MGWLRQAPGKEREFVAA | ISGSGDDT | YYADSVKGRFTISPDNSKNTLYLQMNSLRPEDTAVYYC |
| **VOBARILIZUMAB_1** | EVQLVESGGGLVQPGGSLRLSCAAS | GSVFKINV | MAWYRQAPGKGRELVAG | II-SGGST | SYADSVKGRFTISRDNAKNTLYLQMNSLRPEDTAVYYC |

Primary contact position with no tolerance for mutations

Primary contact positions with tolerance for mutations

Secondary contact positions

Tolerated mutations

Binding-abolishing mutations (1A) V11L and L89V

FIG. 1

1 – caplacizumab
2 – isecarosmab (1)
3 – sonelokimab (3)
4 – vobarilizumab (1)

1 – caplacizumab
2 – isecarosmab (1)
3 – sonelokimab (3)
4 – vobarilizumab (1)

Cluster A

```
A-KDRYSSYYFDY
A-RDRSSWYYFDY
A-RDSSGWYNFDY
A-RDSSSWHYFDY
A-RDSSSWYVFDY
A-REDSSWYYFDY
ARRDKSGWYYFDY
A-RISSGWYLFDY
A-IDSSGWYYFDY
```

FIG. 11A

Cluster B

```
ARDL--SSGWYRDAFDI
ARDRYYESGSY-DAFDI
AREG-YSSGWS-DAFDI
ARGRDFWSGYY-DAFDI
ARGR-YSSGWF-DAFDI
ARLR-YSGSYL-DAFDI
ARPI-YSGSYQ-PAFDI
ARPR-YSSNYY-DAFDI
ARQR--SSGWYWDAFDI
ARQV-HSSGWY-DAFDI
ARPE-DSGSYF-DAFDI
ARRG-YSSGWYKDAFDI
ARVR-YSSGWY-DAFDI
```

FIG. 11B

SINGLE DOMAIN ANTIBODY LIBRARIES WITH MAXIMIZED ANTIBODY DEVELOPABILITY CHARACTERISTICS

CROSS REFERENCE TO RELATED APPLICATIONS

This application claims the benefit of the filing date of U.S. Provisional Application No. 63/311,438, filed on Feb. 17, 2022, the entire contents of which is incorporated by reference herein.

REFERENCE TO SEQUENCE LISTING

The instant application contains a Sequence Listing which has been filed electronically in XML format and is hereby incorporated by reference in its entirety. Said XML copy, created on Feb. 17, 2023, is named 112310-0033-70003US01_SEQ.XML and is 98,332 bytes in size.

The invention relates to VHH antibody libraries with heavy chain variable domain framework scaffolds having complementary determining regions (CDRs) found in naturally-occurring human antibodies

BACKGROUND OF THE INVENTION

There are currently three recombinant antibody platforms primarily used to generate human antibodies for human therapeutic use: (1) the "humanization" of murine monoclonal antibodies; (2) the immunization of transgenic mice containing human antibody genes; and (3) in vitro selection from vast human antibody libraries. Immunization approaches depend upon the occurrence of appropriate in vivo immune responses and may not yield antibodies with desired characteristics. In contrast, in vitro selection has the advantage that antibodies with specific properties can be directly selected, and once selected, can be easily improved in terms of affinity or specificity.

In general, there are two types of antibody libraries: synthetic and natural antibody libraries. Synthetic antibody libraries can be constructed by introducing randomized complementarity determining region (CDR) sequences into antibody framework scaffolds, i.e., between framework region (FR) sequences. Such antibody libraries can have vast potential genetic diversity and improved expression via selection of well-characterized framework scaffolds. However, synthetic antibody libraries also include many non-functional antibody members and exclude much natural diversity due to the formulaic manner used to generate diversity within a restricted set of framework scaffolds.

Antibody libraries created from natural sources, known as natural antibody libraries, have the advantage that the rearranged variable (V) genes undergo quality control in the B cell, and consequently a far higher proportion of the V genes are biologically functional, even if the potential diversity is lower. Disadvantages include the challenges of obtaining large numbers of B-cells to increase diversity, and the poor expression and biophysical properties of some antibodies expressed recombinantly in *E. coli*, yeast or mammalian cells. A single-domain antibody (sdAb, VHH, nanobody) consists of a single monomeric variable antibody domain. Like a whole antibody, it is able to bind selectively to a specific antigen. The low molecular weight makes sdAbs highly soluble and stable, in addition to enabling better permeability into tissues compared to F(ab) and $F(ab')_2$ fragments. Moreover, due to the absence of an Fc region, sdAbs do not show complement triggered cytotoxicity. sdAb libraries are therefore expected to have a variety of diagnostic and therapeutic applications.

SUMMARY OF THE INVENTION

Provided herein are antibody libraries comprising a single domain heavy chain (VHH), which comprise heavy chain framework regions and complementary determining regions (CDRs), where the CDRs are derived from naturally occurring antibodies. Accordingly, one aspect of the present disclosure features a VHH antibody library, comprising a population of antibody VHH domains encoded by a plurality of nucleic acids, said population of antibody VHH domains collectively comprising a population of CDR1s, a population of CDR2s, and a population of CDR3s located at the CDR1 region, the CDR2 region, and the CDR3 region of a VHH gene. The amino acid sequences of the CDR1s, the CDR2s, and the CDR3s may be derived from naturally-occurring antibodies of a mammalian species, for example, human or camelid.

In some embodiments, the heavy chain framework (scaffold) regions (framework 1, framework 2, framework 3 and framework 4) are derived from a single VHH domain from a therapeutic antibody for example, Caplacizumab, Envafolimab, Gontivimab, Isecarosmab, Ozoralizumab, Sonelokimab or Vobarilizumab, coding nucleotide sequence for exemplary parental scaffolds shown in SEQ ID NOs: 1, 2, 3 and 4 (or nucleotide sequences encoding the corresponding amino acid sequences shown in SEQ ID NOs: 53, 54, 55, and 56 due to codon degeneracy), respectively, the nucleotide sequences for the deleted CDR1 versions of these parental scaffolds shown in SEQ ID NOs: 5, 7, 9 and 11 respectively, and the nucleotide sequences for the deleted CDR2 versions of these parental scaffolds shown in SEQ ID NOs: 6, 8, 10 and 12 respectively. Scaffolds may also be based on modified versions of these therapeutic antibodies, such modifications introduced to bring scaffolds closer to germlines or other therapeutic VHHs, eliminate sequence liabilities, or permit protein A binding. For example, Isecarosmab can be mutated in two framework positions to be closer to the human germline VH3-23 (V11L and L89V, Kabat numbering). Coding nucleotide sequence for exemplary parental scaffold shown in SEQ ID NO: 57 (or nucleotide sequences encoding the corresponding amino acid sequence shown in SEQ ID NO: 58 due to codon degeneracy), the nucleotide sequences for the deleted CDR1 versions of this parental scaffold shown in SEQ ID NO: 59, and the nucleotide sequence for the deleted CDR2 versions of these parental scaffolds shown in SEQ ID NOs: 60.

At least 90% of the population of heavy chain CDR1s and at least 90% of the population of heavy chain CDR2 are completely free of members carrying one or more liabilities that affect one or more features of an antibody carrying such. Such VHH libraries, comprising CDRs from natural antibodies such as human antibodies would have a high number of functional members and reflect natural diversity of human antibodies. Excluding members carrying one or more liabilities as described herein would enhance the percentage of members having desired properties, for example, high yield when produced by recombinant technology, high stability, reduced aggregation capacity, reduced liabilities as described below etc. Thus, the VHH libraries described herein would maximize antibody developability characteristics.

The population of heavy chain CDR1s, the population of heavy chain CDR2s, and/or the population of heavy chain CDR3s are free (e.g., substantially free) of members comprising one or more of the following liabilities:

(i) a glycosylation site,
(ii) a deamidation site,
(iii) an isomerization site,
(iv) any cysteines,
(v) net charge greater than 1,
(vi) a tripeptide motif containing at least two residues with aromatic side chains,
(vii) a polyspecificity site;
(viii) a protease sensitive or hydrolysis prone site,
(ix) an integrin binding site,
(x) a lysine glycation site,
(xi) a metal catalyzed fragmentation site,
(xii) a polyspecificity aggregation site,
(xiii) a streptavidin binding motif,
(xiv) one or more arginines;
(xv) a hydrophobic CDR sequence;
(xvi) a CDR mutation that reduces binding to protein A In this embodiment, the glycosylation site of (i) comprises the motif NXS, NXT, or NXC, in which X represents any naturally-occurring amino acid residue except for proline; the deamidation site of (ii) comprises the motif of NG, NS, NT, NN, NA, NH, ND, NQ, NF, NW or NY; the isomerization site of (iii) comprises the motif of DT, DH, DS, DG, DN, DR, DY or DD; the aromatic residues of the tripeptide motif of (vi) comprise F, H, W or Y; the polyspecificity site of (vii) comprises the motif GG, GGG, RR, VG, W, WV, WW, WWW, YY, or WXW, in which X represents any amino acid residue; the protease sensitive or hydrolysis prone site of (viii) comprises the motif of DX, in which X is P, G, S, V, Y, F, Q, K, L, or D; the integrin binding site of (ix) comprises RGD, RYD, LDV, or KGD; the lysine glycation site of (x) comprises KE, EK, or ED; the metal catalyzed fragmentation site of (xi) comprises the motif of HS, SH, KT, HXS, or SXH, in which X represents any amino acid residue; the polyspecificity aggregation site of (xii) comprises a motif of $X_1X_2X_3$, wherein each of $X_1$, $X_2$, and $X_3$ is independently selected from the group consisting of F, I, L, V, W and Y; and/or the streptavidin binding motif of (xiii) comprises the motif HPQ, EPDW (SEQ ID NO: 49), PWXWL (SEQ ID NO: 50), in which X represents any amino acid residue, GDWVFI (SEQ ID NO: 51), or PWPWLG (SEQ ID NO: 52); where the hydrophobic CDR sequence of (xv) is summed using reference numbers from Parker J M et al. Biochemistry. 1986 Sep. 23; 25(19):5425-32 and results in a value smaller than zero, and where the CDR mutation that reduces binding to protein A of (xvi) involves any mutation in the last amino acid of the CDR2, according to the IMGT definition, to A, G, C, D, E, F, G, H, I, L, M, N, P, Q, S, V, W or Y. Further, at least 95% of the population of CDR1s, at least 95% of the population of CDR2s, and at least 95% of the population of CDR3s are completely free of non-functional members.

In some embodiments, the population of antibody heavy chain CDR1 fragments, the population of antibody heavy chain CDR2 fragments, and/or the population of antibody heavy chain CDR3 fragments is free of members comprising at least two of (i)-(xvi). In some examples, at least the population of antibody heavy chain CDR1 fragments, the population of antibody heavy chain CDR2 fragments, and/or the population of antibody heavy chain CDR3 fragments is free of members comprising (i)-(ix), and optionally free of members comprising one or more of (x)-(xvi).

In some embodiments, the antibody library described herein comprise a population of heavy chain CDR1s and/or a population of heavy chain CDR2s that is free of members comprising one or more of (i)-(xvi), and a population of heavy chain CDR3s is derived from naturally-occurring human antibodies (without removal of one or more the liability (i)-(xvi) disclosed herein), for example, derived from human B lymphocytes or precursor cells thereof.

In some instances, members of the antibody library described herein comprise heavy chain CDR1, heavy chain CDR2, and/or heavy chain CDR3 that are not from the same naturally-occurring antibody. For examples, at least 50% of the members in the antibody library do not comprise heavy chain CDR1, heavy chain CDR2, and/or heavy chain CDR3 that are from the same naturally-occurring antibody.

In another aspect, the present disclosure features a method for producing a single domain heavy chain (VHH) antibody library comprising; (a) providing a first plurality of nucleic acids encoding a population of naturally-occurring CDR1 fragments; (b) providing a second plurality of nucleic acids encoding a population of naturally-occurring CDR2 fragments; (c) providing a third plurality of nucleic acids encoding a population of naturally-occurring CDR3 fragments; (d) providing a nucleic acid gene encoding a common VHH domain comprising heavy chain framework regions framework 1, framework 2, framework 3 and framework 4, and inserting the first plurality of nucleic acids, the second plurality of nucleic acids, and the third plurality of nucleic acids into the CDR1 region, the CDR2 region, and the CDR3 region, respectively, of the common VHH domain, thereby producing a population of nucleic acids encoding a VHH domain library.

The heavy chain CDR1 fragments, the heavy chain CDR2 fragments, and the heavy chain CDR3 fragments may be derived from naturally-occurring antibodies of a mammalian species as disclosed herein. In some embodiments, the heavy chain CDR1, CDR2, and CDR3 fragments can be derived from the same mammalian species. Optionally, the common heavy chain variable region gene may also be derived from the same mammalian species.

In some embodiments, the antibody library comprises members in each of which the heavy chain CDR1, the heavy chain CDR2, and/or the heavy chain CDR3 are not from the same naturally-occurring antibody. For example, at least 50% of the members in the antibody library do not contain heavy chain CDR1, the heavy chain CDR2, and/or the heavy chain CDR3 from the same naturally-occurring antibody.

The population of heavy chain CDR1s, the population of heavy chain CDR2s, and/or the population of heavy chain CDR3s are free (e.g., substantially free) of members comprising one or more of the following liabilities:

(i) a glycosylation site,
(ii) a deamidation site,
(iii) an isomerization site,
(iv) any cysteines,
(v) net charge greater than 1,
(vi) a tripeptide motif containing at least two residues with aromatic side chains,
(vii) a polyspecificity site;
(viii) a protease sensitive or hydrolysis prone site,
(ix) an integrin binding site,
(x) a lysine glycation site,
(xi) a metal catalyzed fragmentation site,
(xii) a polyspecificity aggregation site,
(xiii) a streptavidin binding motif,
(xiv) one or more arginines;
(xv) a hydrophobic CDR sequence;
(xvi) a CDR mutation that reduces binding to protein A In this embodiment, the glycosylation site of (i) comprises the motif NXS, NXT, or NXC, in which X represents any naturally-occurring amino acid residue except for proline; the deamidation site of (ii) comprises the motif of NG, NS, NT, NN, NA, NH, ND, NQ, NF, NW or NY; the isomerization site of (iii) comprises the motif of DT, DH, DS, DG, DN, DR, DY or DD; the aromatic residues of the tripeptide motif of (vi) comprise F, H, W or Y; the polyspecificity site of (vii) comprises the motif GG, GGG, RR, VG, W, WV, WW, WWW, YY, or WXW, in which X represents any amino acid residue; the protease sensitive or hydrolysis prone site of (viii) comprises the motif of DX, in which Xis P, G, S, V, Y, F, Q, K, L, or D; the integrin binding site of (ix) comprises RGD, RYD, LDV, or KGD; the lysine glycation site of (x) comprises KE, EK, or ED; the metal catalyzed fragmentation site of (xi) comprises the motif of HS, SH, KT, HXS, or SXH, in which X represents any amino acid residue; the polyspecificity aggregation site of (xii) comprises a motif of $X_1X_2X_3$, wherein each of $X_1$, $X_2$, and $X_3$ is independently selected from the group consisting of F, I, L, V, W and Y; and/or the streptavidin binding motif of (xiii) comprises the motif HPQ, EPDW (SEQ ID NO: 49), PWXWL (SEQ ID NO: 50), in which X represents any amino acid residue, GDWVFI (SEQ ID NO: 51), or PWPWLG (SEQ ID NO: 52); where the hydrophobic CDR sequence of (xv) is summed using reference numbers from Parker J M et al. Biochemistry. 1986 Sep. 23; 25(19):5425-32 and results in a value smaller than zero, and where the CDR mutation that reduces binding to protein A of (xvi) involves any mutation in the last amino acid of the CDR2, according to the IMGT definition, to A, G, C, D, E, F, G, H, I, L, M, N, P, Q, S, V, W or Y. Further, at least 95% of the population of CDR1s, at least 95% of the population of CDR2s, and at least 95% of the population of CDR3s are completely free of non-functional members.

In some embodiments, the population of antibody heavy chain CDR1 fragments, the population of antibody heavy chain CDR2 fragments, and/or the population of antibody heavy chain CDR3 fragments is free of members comprising at least two of (i)-(xvi). In some examples, at least the population of antibody heavy chain CDR1 fragments, the population of antibody heavy chain CDR2 fragments, and/or the population of antibody heavy chain CDR3 fragments is free of members comprising (i)-(ix), and optionally free of members comprising one or more of (x)-(xvi).

In some embodiments, the antibody library described herein comprise a population of heavy chain CDR1s and/or a population of heavy chain CDR2s that is free of members comprising one or more of (i)-(xvi), and a population of heavy chain CDR3s is derived from naturally-occurring human antibodies (without removal of one or more the liability (i)-(xvi) disclosed herein), for example, derived from human B lymphocytes or precursor cells thereof.

In some embodiments, the first plurality of nucleic acids, the second plurality of nucleic acids, and/or the third plurality of nucleic acids is produced by a process comprising; (a) obtaining amino acid sequences of the heavy chain CDR1 regions, heavy chain CDR2 regions and heavy chain CDR3 regions of a population of naturally-occurring antibodies; (b) excluding from (a) the heavy chain CDR1 amino acid sequences, the heavy chain CDR2 amino acid sequences, and the heavy chain CDR3 amino acid sequences amino acid sequences that comprise any or all of (i) to (xvi) to obtain liability-free heavy chain CDR1 sequences, liability-free heavy chain CDR2 sequences and liability-free heavy chain CDR3 sequences; and (c) synthesizing the first plurality of nucleic acids that encode the liability-free heavy chain CDR1 regions, the second plurality of nucleic acids that encode the liability-free heavy chain CDR2 regions, and the third plurality of nucleic acids that encode the liability-free heavy chain CDR2 regions.

In some instances, the third plurality of nucleic acids is produced by a process comprising; (a) amplifying the heavy chain CDR3 regions from a population of B cells; and (b) combining the third plurality of nucleic acids that encode the heavy chain CDR3 regions obtained in (a) with the remaining CDRs.

In some instances, the process described above may further comprise isolating functional members from the liability-free heavy chain CDR1 and CDR2 regions, and/or from the CDR3 regions. For example, the functional members of the liability-free heavy chain CDR1 and CDR2 regions or the functional members of the CDR3 regions are isolated by expressing antibodies comprising the liability-free heavy chain CDR1 and CDR2 regions, and/or the CDR3 regions in host cells in a manner that the antibodies are displayed on surface of the host cells, isolating the antibodies that display on the host cells, and identifying the CDR1, CDR2, and/or CDR3 regions in the displayed antibodies, which are functional members of the CDR1, CDR2, and/or CDR3 regions. Alternatively, the functional members of the liability-free heavy chain CDR1 and CDR2 regions, and/or the CDR3 regions are isolated by expressing antibodies comprising the liability-free heavy chain CDR1 and CDR2 regions, and/or the CDR3 regions in fusion with a folding reporter, which optionally is β-lactamase or green fluorescent protein, or fragments thereof, to obtain members with improved folding.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 1 shows sequence analysis of the indicated antibodies for prediction of Protein A binding site (SEQ ID NOs: 61 to 71, from top to bottom).

FIG. 6A shows binding of Protein A to yeast expressing the Caplacizumab framework scaffold. FIG. 6B shows binding of Protein A to yeast expressing the Isecarosmab framework scaffold. FIG. 6C shows binding of Protein A to yeast expressing the Sonelokimab framework scaffold. FIG. 6D shows binding of Protein A to yeast expressing the Vobarilizumab framework scaffold. FIG. 6E shows binding of Protein A to yeast expressing the positive control, VH3-7/Vk2-28 scFv. FIG. 6F shows absence of binding of Protein A to yeast expressing the negative control, VH4-30-4/Vk3-11 scFv.

FIG. 8A is a schematic representation of CDR1 as sequence logos selected to be inserted in the library. FIG. 8B is a schematic representation of CDR2 as sequence logos selected to be inserted in the library.

FIGS. 11A-11B shows exemplary clusters of HCDR3 from which a single sequence can be chosen to represent the given cluster. Each line shows a distinct HCDR3 sequence, with amino acids not matching cluster consensus highlighted in black. FIG. 11A shows an exemplary cluster of HCDR3s for Cluster A. (SEQ ID NOs: 81 to 89, top to bottom). FIG. 11B shows an exemplary clusters of HCDR3s for Cluster B. (SEQ ID NOs: 90 to 102, top to bottom).

FIG. 14A shows western blots of the libraries built on the 4 framework scaffolds, caplacizumab, isecarosmab (1), sonelokimab (3) and vobarilizumab (1). FIG. 14B shows western blot for a scFv library phage displaying the four VHH framework scaffolds, caplacizumab, isecarosmab (1), sonelokimab (3) and vobarilizumab (1).

DETAILED DESCRIPTION OF THE INVENTION

Figure 2:
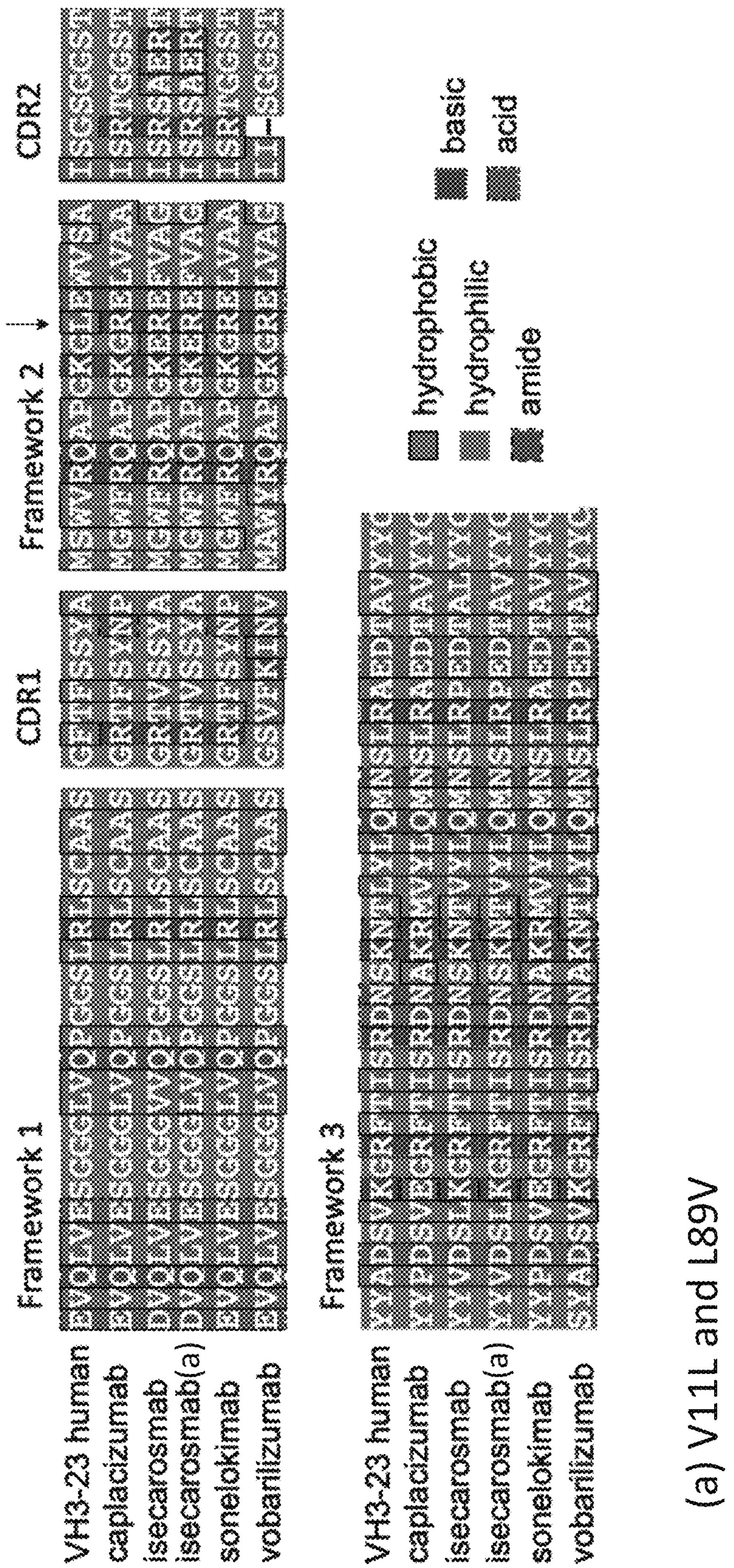
FIG. 2 shows a comparative sequence analysis of the selected VHH domains with the human VH3-23 germline sequence (SEQ ID NOs: 72 to 77, top to bottom).

It is generally accepted that the larger or more diverse an antibody library, measured in terms of the number of different antibodies, the better the antibodies that can be selected from it. Griffiths et al., *EMBOJ* 13(14):3245-3260, 1994 and Perelson et al., *J Theor Biol.,* 81(4):645-70, 1979. The diversity of most antibody libraries has been estimated by counting the number of transformants, assuming that each colony represents a different antibody.

It was generally assumed that the VH gene diversity was the same as the number of colonies obtained, e.g., $-10^8$ for the library described in Sblattero et al., *Nat Biotechnol.,* 18(1):75-80, 2000. However, next-generation sequencing (NGS) showed that the VH clonal diversity (unique HCDR3 amino acid sequences) was actually ~30 fold lower ($3\times10^6$). D'Angelo et al., *MAbs.,* 6(1):160-72, 2014. Notwithstanding this apparent low diversity, many antibodies have been selected from this library. See, e.g., Sblattero et al., *Nat Biotechnol.,* 18(1):75-80, 2000; Glanville et al., *Curr Opin Struct Biol.,* 33:146-60, 2015; Lou et al., *Journal of immunological methods;* 253(1-2):233-42, 2001; Kehoe et al., *Mol Cell Proteomics,* 5(12):2350-63, 2006; Ayriss et al., *J Proteome Res.* 6(3):1072-82, 2007; Velappan et al., *Journal of immunological methods,* 321(1-2):60-9, 2007; Lillo et al., *PLoS One,* 6(12):e27756, 2011; Ferrara et al., *PLoS One,* 7(11):e49535, 2012; Close et al., *BMC Microbiol.* 13:270, 2013; and Ferrara et al., *MAbs,* 7(1):32-41, 2015.

NGS sequencing of another natural antibody library showed an even lower measured VH diversity ($2\times10^5$), even though the number of donors used (654) was extremely high, and the estimated number of colonies was $3\times10^{10}$. Glanville et al., *Proceedings of the National Academy of Sciences of the United States of America,* 106(48):20216-21, 2009. Further, Fantini et al. *PLoS One.* 12(5):e0177574, 2017 described three libraries with maximal diversities (numbers of colonies) $6\text{-}16\times10^6$, and estimated NGS diversities of $3\text{-}9\times10^6$.

While the diversity found in CDR1-2 can be covered by array-based oligonucleotide synthesis relatively easily, this may not be the case for CDR3 where the original diversity can easily exceed $10^8$ different CDR3 s. Even after liabilities and CDRs found fewer than 4 times are eliminated, the number of different HCDR3s can exceed $10^7$ if NovaSeq ($3\times10^9$ reads) is used to assess diversity. While genetic diversity is essential, effective functional diversity is even more important: a high genetic diversity is of no utility if the encoded antibodies are non-functional and unable to fold properly. Indeed, a single amino acid change in an antibody can result in dramatic changes in expression levels and stability. Some publications have shown the superiority of natural antibody libraries over synthetic ones. Hugo et al., *Protein Eng.,* 16(5):381-6, 2003; Wang et al., *Proteins,* 82(10):2620-30, 2014; and Chan et al., *Journal of immunological methods,* 373(1-2):79-88, 2011. Natural diversity has the advantage that it has been prescreened for functionality by the immune system. However, it has the disadvantage that some antibodies are poorly expressed and folded in in vitro display systems, and that diversity can be dominated by a small number of clones.

The present disclosure aims, at least in part, at constructing single domain antibody libraries comprising natural diversity such that the members of the libraries would be prescreened by the immune system for functionality, while excluding members that contain potential liabilities, would be poorly expressed, aggregating and/or poorly folded in a common screening system (e.g., yeast display, phage display, or a folding reporter such as ß-lactamase; see, e.g., Saunders et al., *Nat. Che Biol.,* 12:94-101; 1988; and D'Angelo et al., *BMC genomics* 12, suppl. 1, S1-S5; 2011; or green fluorescent protein; see e.g. Waldo, et al., *Nat. Biotechnol.,* 17: 691-5; 1999; Cabantous, et al., *PLoS ONE.,* 3:e2387; 2008; and Cabantous, et al., *J Struct Funct Genomics,* 6:113-9; 2005). The present disclosure thus features, in some embodiments, a method to create extremely diverse, highly functional antibody libraries by combining naturally occurring CDRs, including naturally occurring CDRs containing somatic mutations generated in vivo, within antibody scaffolds such that members of the antibody libraries are expected to be well expressed and/or folded, and lacking liabilities.

As used herein, the term "liability" refers to a motif in an antibody (e.g., located in a heavy chain region) that would negatively affect one or more desired features of the antibody (e.g., stability, good expression in an expression or display system, proper folding, no or reduced aggregation, solubility, no or reduced integrin binding, no or reduced glycosylation, no or reduced deamidation, no or reduced isomerization, no unpaired cysteine, or no or reduced protease sensitivity, etc.). By virtue of being comprised of highly functional members, such an antibody library would be expected to be functionally much larger than libraries of similar genetic size, in which antibodies are present that contain any of these liabilities. In other words, the antibody libraries disclosed herein would have a much larger effective diversity.

I. VHH Antibody Libraries and Methods of Construction

Provided herein are single domain antibody (sdAb) libraries comprising the heavy chain elements (VHH antibody libraries) as described herein, wherein the heavy chain CDRs are inserted into a pre-selected heavy chain variable domain gene framework scaffold as also described herein, as well as methods of producing such antibody libraries. The heavy chain CDR1s, CDR2s, and/or CDR3s, and the pre-selected heavy chain variable domain framework scaffold may be of a mammalian species, for example, human, mouse, rat, rabbit, dog, pig, or camelid such as camel or llama. In some instances, the heavy chain CDR1s, CDR2s, and CDR3s may be derived from antibodies of the same mammalian species (e.g., human or camelid). Optionally, the pre-selected heavy chain variable domain gene may be from the same mammalian species. Alternatively, the heavy chain CDR1s, CDR2s, and/or CDR3s, and optionally the pre-selected heavy chain variable domain gene may be derived from naturally-occurring antibodies of different mammalian species. In some embodiments, the heavy chain CDRs and the pre-selected variable domain gene, are all of the same mammal species, for example, human.

A VHH antibody (interchangeably used in plural form) is a single monomeric variable antibody domain capable of specific binding to a target antigen, such as a carbohydrate, polynucleotide, lipid, polypeptide, etc., through an antigen recognition site. As used herein, the term "antibody" encompasses nanobodies, single domain antibodies (also known as nanobodies, e.g., a $V_H$ only antibody such as the VHH antibodies found in camelids). Heavy chain only antibodies (HcAb) are naturally produced by camelids and sharks. The antigen binding portion of the HcAb is comprised of the VHH fragment. Vincke et al., *Methods Mol Biol.* 911:15-26 (2012).

A VHH antibody comprises a heavy chain variable region (VH) that is subdivided into regions of hypervariability, also known as "complementarity determining regions" ("CDR"), interspersed with regions that are more conserved, which are known as "framework regions" ("FR") or scaffolds. Each VH is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Immunological Interest*, Fifth Edition, U.S. Department of Health and Human Services, NIH Publication No. 91-3242, Chothia et al., (1989) *Nature* 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinforg.uk/abs).

The antibody libraries disclosed herein comprises a VHH antibody library. Exemplary steps for constructing the antibody libraries described herein may include:

(1) Identifying suitable heavy chain variable domain gene scaffolds;

(2) Generating vectors based on the scaffolds containing a single insertion site for each CDR, the remaining CDRs may remain unchanged;

(3) Identifying naturally occurring CDRs by analysis of a database of naturally occurring antibody sequences (which may be obtained from sequencing members of a natural antibody library);

(4) Eliminating from the database of naturally occurring CDR sequences those sequences likely to encode liabilities;

(5) Synthesize the remaining set of CDRs as oligonucleotides;

(6) Inserting the CDRs at their appropriate sites within the previously modified scaffolds, each scaffold containing CDRs at only one site (e.g., the identified collection of HCDR1s is inserted at the HCDR1 site of the modified scaffold).

In some embodiments, the CDRs (e.g., CDR1, CDR2, CDR3, or a combination thereof) identified as described herein may be experimentally screened or selected for good folding and/or expression and screened or selected against liabilities such as poor folding, poor expression, polyreactivity or aggregation. The selected CDRs may be inserted into complete V domains within the context of the scaffolds. The resultant complete V domains could be further screened and selected for good folding and/or expression, and/or screened and selected against liabilities such as poor folding or expression, polyreactivity or aggregation. The selected VH complete scaffold can be assembled and cloned into an appropriate display vector (e.g., phage or yeast) for screening of antibodies having desired binding specificity.$$

A. Selection of Heavy Chain Variable Domain Framework Scaffolds

In some embodiments, the heavy chain framework scaffolds used in constructing the antibody libraries described here may be derived from commercially available therapeutic antibodies (e.g., those whose marketing authorization has been approved by the US Food and Drug Administration or/or the European Medicines Agency) or therapeutic antibodies that are currently in clinical trials, for example, in phase II or phase III trials. As used herein, a therapeutic antibody refers to the antibody molecule of an approved drug product (e.g., in the US, in EP, or in other jurisdictions such as CA or JP), or an antibody molecule that has been or is currently in a clinical trial in a suitable jurisdiction, for example, in the US or in Europe. The following is an exemplary list of factors that are taken into consideration when selecting framework scaffolds:

(i) be currently approved for therapeutic use, or undergoing clinical trials;

(ii) have affinity for *Staphylococcus aureus* protein A to facilitate purification upon manufacturing. VHH domains are similar to human VH3 domains, many of which are known to have affinity to protein A;

(iii) lack cysteine residues, except for the canonical pair at framework 1 and framework 3 (Kabat positions 22 and 92);

(iv) have an arginine residue at framework 2 as opposed to the canonical leucine residue present in the VH/VL interface in human antibodies (Kabat position 45);

(v) have the canonical tryptophan residues as the first residue of framework 4 (Kabat position 103). In the final library this region will be sourced from human donors where the majority of sequences will have tryptophan residues at this position;

The germline heavy chain variable domain genes used in such therapeutic antibodies can be examined for features such as aggregation, hydrophobic interaction, polyspecificity, monomericity, level of expression and purification characteristics. Table 1 Those having the desired features can be selected as framework scaffolds for library constructions. Features and selection criterion are provided in Table 1, which shows as exemplary examples of therapeutic antibodies considered, some of which are multidomain/multi-specific (number in parenthesis indicates the domain analyzed). A sequence analysis for these therapeutic VHH antibodies is shown in FIG. 1.

In some specific examples, the VH framework scaffolds used in the antibody library described herein are derived from Caplacizumab, Envafolimab, Gontivimab, Isecarosmab, Ozoralizumab, Sonelokimab or Vobarilizumab. Characteristics of exemplary antibodies are provided in Table 2. As used herein, "derived from" refers to the use of the VH genes of any of these therapeutic antibodies, either with no modification, or with one or more mutations introduced into one or more of the framework regions, for example, up to 5 amino acid substitutions (e.g., up to 4, 3, 2, or 1 amino acid substitutions) in the VH gene (e.g., in one or more of the framework regions).

In some instances, the mutations introduced into a germline VH gene or introduced into the VH gene of a reference therapeutic antibody (e.g., those listed in Table 2) may be conservative substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The nucleotide sequences of exemplary VH framework scaffolds are shown in Table 3. Nucleotide sequences for deleted CDR1 and CDR2 versions of the exemplary VH framework scaffolds are shown in Table 4.

Any of the VH framework scaffolds described herein can be used to construct a cassette that allows for cloning of one or more of pluralities of nucleic acids each encoding a diverse population of a heavy chain CDRs into the corresponding framework scaffold at the corresponding CDR position.

In some instances, restriction sites can be introduced into a heavy chain framework scaffold flanking the CDR1 region or the CDR2 region for cloning a plurality of nucleic acids encoding a diverse population of heavy chain CDR1s, or heavy chain CDR2s respectively. In one example, restriction sites can be introduced into a heavy chain framework scaffold flanking all of the CDR1 and CDR2 regions for cloning diverse heavy chain CDR1s and CDR2s at the corresponding locations.

Figure 3:
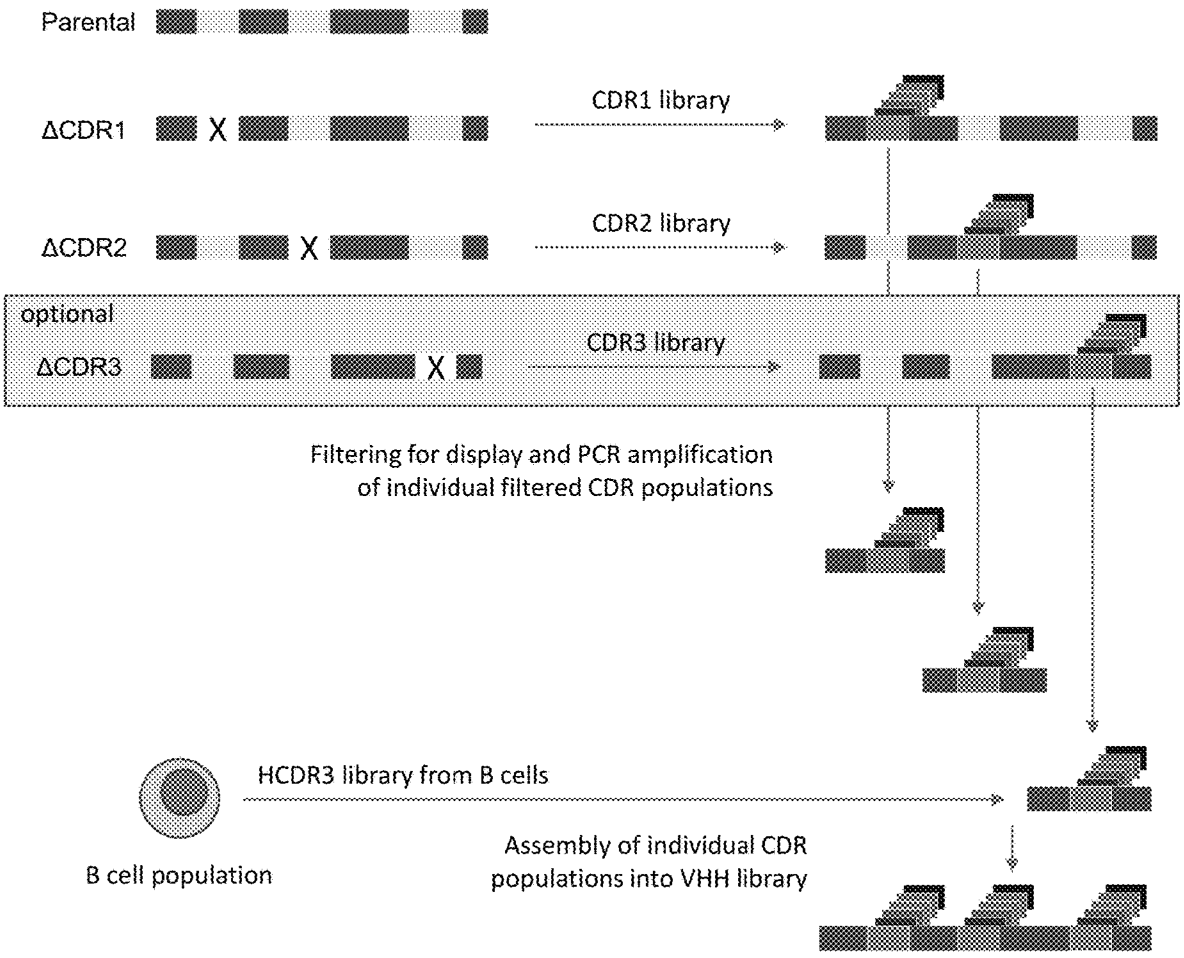
FIG. 3 shows schematic representations of the parental VHH framework scaffold, the deleted CDR (ΔCDR) versions used in building single-CDR libraries, and the assembly of final VHH libraries from filtered CDR libraries using either replicated natural HCDR3s or HCDR3s derived from B cells.

FIGS. 2 and 3 illustrate an exemplary scheme for construction of cassettes for introducing heavy chain CDR1, CDR2, or CDR3 diversities into a heavy chain framework scaffold. The resultant cassettes can be located in a suitable expression vector for producing the encoded antibodies in a suitable expression, display or folding reporter system.

B. Heavy Chain CDR Populations

The heavy chain CDR1, CDR2, and/or CDR3 populations in the antibody libraries can be derived from naturally-occurring human antibodies. Such CDR sequences can be obtained by sequencing naturally-occurring antibodies (e.g., human antibodies) in existing natural antibody libraries and analyzing the heavy chain sequences thus obtained by conventional methods to identify heavy chain CDR sequences. Alternatively, or in addition, naturally-occurring antibody CDR sequences can be obtained by analyzing sequences of such antibodies in publicly available databases of naturally-occurring antibody sequences (e.g., human antibody sequences or camelid VHH antibody sequences), e.g., the NCBI database, the IMGT database, sequences from Jackson et al., J. Immunol. Methods, 324:26, 2007, and/or the sequences from Lee et al., Immunogenetics, 57:917, 2006, The Observed Antibody Space (antibodymap.org) described in Kovaltsuk, A. et al. Observed Antibody Space: A Resource for Data Mining Next-Generation Sequencing of Antibody Repertoires. *Journal of Immunology*, doi:10.4049/jimmunol.1800708 (2018), and/or the iReceptor database (ireceptor.irmacs.sfu.ca) described in Corrie, B. D. et al. iReceptor: A platform for querying and analyzing antibody/B-cell and T-cell receptor repertoire data across federated repositories. *Immunol Rev* 284, 24-41, doi:10.1111/imr.12666 (2018), and/or the sequence database described in Briney, B. et al., Commonality despite exceptional diversity in the baseline human antibody repertoire. *Nature*, doi:10.1038/s41586-019-0879-y (2019).

The extent of the framework region and CDRs can be precisely identified using methodology known in the art, for example, by the Kabat definition, the IMGT definition, the Chothia definition, the AbM definition, and/or the contact definition, all of which are well known in the art. See, e.g. Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec.

Biol. 273:927-948; Lefranc, M. P. et al. IMGT unique numbering for immunoglobulin and T cell receptor variable domains and Ig superfamily V-like domains. *Dev Comp Immunol* 27, 55-77 (2003) and Almagro, J. Mol. Recognit. 17:132-143 (2004). See also hgmp.mrc.ac.uk, IMGT.org and bioinforg.uk/abs.

Figure 8A:
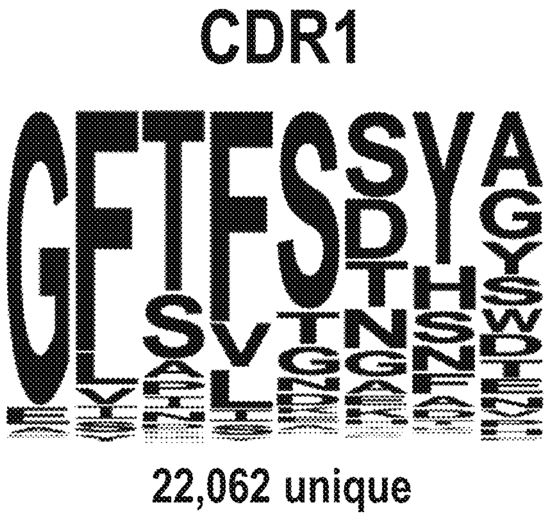
FIGS. 8A-8B are schematics of sequence logos of CDRs selected to be inserted in the library.
Figure 8B:
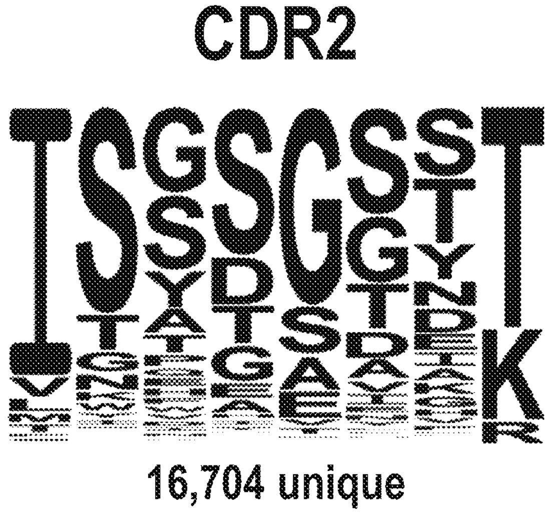

The heavy chain CDR1, CDR2, and/or CDR3 sequences thus obtained may be further analyzed to remove those that comprise a liability, e.g., those listed in Table 6. In some instances, heavy chain CDR1, CDR2, and/or CDR3 sequences comprising one of the liabilities listed in Table 6 (e.g., a glycosylation site, a deamidation site, an isomerization site, an unpaired cysteine, a net charge greater than 1 (e.g., in HC CDR1-2), a tripeptide motif containing at least two aromatic residues (which may affect viscosity), a motif that promotes aggregation, (viii) a polyspecificity site such as those containing a motif of GG, GGG, RR, VG, W, WV, WW, WWW, YY, or, WW, in which X represents any amino acid residue; a protease sensitive site (fragmentation sensitive site), or an integrin binding site). FIGS. 8A-8B show a logo representation of the final CDR1 and CDR2 sequences. Additional, or different, sequence liabilities in any combination may be similarly eliminated from databases of CDRs, so providing a list of CDRs free of sequence liabilities.

Alternatively, or in addition, potential glycation sites such as lysine glycation sites may be removed. A glycation site refers to a site in a protein molecule that can be linked to a sugar molecule via a nonenzymatic process. Exemplary glycation sites include, but are not limited to, KE, EK, and ED. Additional liabilities include metal catalyzed fragmentation site (e.g., HS, SH, KT, HXS, or SXH, in which X represents any amino acid residue), polyspecificity aggregation site (e.g., having a motif of $X_1X_2X_3$, in which each of $X_1$, $X_2$, and $X_3$ is independently F, I, L, V, W, or Y), and streptavidin binding motif (e.g., HPQ EPDW (SEQ ID NO:49), PWXWL (SEQ ID NO: 50), in which X represents any amino acid residue, GDWVFI (SEQ ID NO: 51), and PWPWLG (SEQ ID NO: 52)).

Substantially free means that the number of a heavy CDR comprising the liability is less than 20% in the library, e.g., less than 15% or less than 10%. In some examples, heavy chain CDR1, CDR2, and/or CDR3 sequences comprising two or more (e.g., 3, 4, 5, 6, 7, or more) of the liabilities noted above can be removed such that the resultant library is free of (substantially free of or completely free of) members comprising the excluded liabilities. In one example, heavy chain CDR1, CDR2, and/or CDR3 sequences comprising all of the liabilities listed in Table 6 can be removed such that the resultant library is free of (substantially free of or completely free of) members comprising any of the liabilities. Alternatively, or in addition, heavy chain CDR1, CDR2, and/or CDR3 sequences comprising all of the liabilities listed in Table 6 can be removed such that the resultant library is free of (substantially free of or completely free of) members comprising any of the liabilities, as illustrated in FIGS. 8A-8B. In one specific example, heavy chain CDR1, CDR2, and/or CDR3 sequences comprising all of the liabilities disclosed herein can be removed such that the resultant library is free of (substantially free of or completely free of) members comprising any of the liabilities.

In some examples, heavy chain CDR1 and CDR2 sequences comprising one or more of liabilities, e.g., those listed in Table 6, can be removed, while heavy chain CDR3 sequences can be derived from naturally-occurring human antibodies without removal of members having the liabilities. Alternatively, heavy chain CDR3 sequences comprising one or more liabilities can also be removed.

In some examples, heavy chain CDR1, CDR2, and/or CDR3 sequences having anomalous lengths can also be excluded.

In some examples, heavy chain CDR1 and CDR2 members containing deamidation sites (e.g., NG, NS, NT, NN, NA, NH, ND, NQ, NF, NW or NY), isomerization sites (e.g., DT, DH, DS, DG, DN, DR, DY or DD), aggregation site (FHW); motifs affecting viscosity (e.g., HYF and HWH), motifs indicating poor developability (e.g., net charge ≥+1 in HCDR1-2), unpaired cysteine, polyspecificity site (e.g., GG, GGG, RR, VG, W, WV, WW, WWW, YY, or WW, X referring to any amino acid residue), and glycosylation sites (e.g., NXS, NXT, or NXC, in which X is any amino acid residue except for proline) can be excluded. In some examples, one or more of the following liabilities in heavy chain CDR1 and heavy chain CDR2 members can also be excluded: additional glycosylation sites (e.g., NXC, X being any amino acid residue except for proline), additional deamination sites (e.g., NA, NH, and/or ND), additional isomerization sites (e.g., DT and/or DH), lysine glycation sites (e.g., KE, EK, and ED), integrin binding sites (e.g., RGD, RYD, LDV, and KGD), protease sensitive sites (fragmentation site) (e.g., DP, DG, DS, DV, DY, DF, DQ, DK, DL, and DD), metal catalyzed fragmentation sites (e.g., HS, SH, KT, HXS, and SXH, in which X represents any amino acid residue), polyspecificity aggregation sites (e.g., having a motif of $X_1X_2X$ 3, in which each of $X_1$, $X_2$, and $X_3$ independently is F, I, L, V, W, or Y), and/or streptavidin binding sites (e.g., HPQ EPDW (SEQ ID NO: 49), PWXWL (SEQ ID NO: 50), in which X represents any amino acid residue, GDWVFI (SEQ ID NO: 51), and PWPWLG (SEQ ID NO: 52)).

In some examples, the heavy chain CDR3 members having the one or more liabilities described herein can also be excluded. Alternatively, the heavy chain CDR3 members may include those derived from naturally-occurring antibodies directly without removal of the one or more liabilities described herein.

The resultant heavy chain CDR1, CDR2, and/or CDR3 sequences obtained from naturally-occurring antibodies, either excluding sequences comprising one or more liabilities or maintaining all sequences, can be used as templates to synthesize nucleic acids encoding, and replicating, the CDR sequences. Such nucleic acids can be inserted into the corresponding CDR position in the VH scaffolds disclosed herein, and are termed “replicated natural CDRs”.

When desired, expression vectors carrying the VH scaffolds with one or more heavy chain CDRs inserted can be introduced into a suitable expression/display system for isolating functional members. Functional members include those having one or more superior features, for example, good expression and display in a suitable display system, improved folding, reduced aggregation or polyreactivity, and/or greater Tm. Such functional members can be identified by collecting host cells displaying antibodies produced from the expression vectors and sequencing the corresponding heavy chain CDR sequences encoded by the expression vectors in the collected host cells.

For example, an initial antibody library may also be sorted for yeast displaying antibodies that have been stained with conformational probes that detect correct antibody folding. Traxlmayr et al., Arch Biochem Biophys. 526(2):174-80, 2012. Examples of such conformational probes include protein A (Hillson et al., The Journal of experimental medicine. 178(1):331-6, 1993; Akerstrom et al., 1994; J. Imm Methods, 177(1-2):151-63, 1994; and Roben et al., J. Immunology 154(12):6437-45, 1995), that is able to bind to VH3 and VHH domains, and derivatives of indole 3-butyric acid (Alves et al., Langmuir, 28(25):9640-8, 2012; Alves et al., Anal Chem., 84(18):7721-8, 2012; Alves et al., Bioconjug Chem., 25(7):1198-202, 2014; and Mustafaoglu et al., Biotechnol Bioeng., 112(7):1327-34, 2015) that binds to the "nucleotide binding site" found in all antibodies (Raj agopalan et al., Proceedings of the National Academy of Sciences of the United States of America, 93(12):6019-24, 1993).

The previous use of conformational probes has been shown to predict high expression and thermostability (Traxlmayr et al., 2012; Shusta et al., J Mol Biol. 292(5):949-56, 1999; Traxlmayr et al., Biochim Biophys Acta., 1824(4): 542-9, 2012; Traxlmayr et al., Protein Eng Des Sel., 26(4): 255-65, 2013; and Hasenhindl et al., Protein Eng Des Sel., 26(10):675-82, 2013) in yeast display. This approach selects for antibody fragments that are well expressed and well folded. Rather than positive selection for good display, each individual CDR library can be depleted of CDRs that contain liabilities. For example, adapting screens used for antibody screening (Yang et al., MAbs., 5(5):787-94, 2013; Kelly et al., MAbs, 7(4):770-7, 2015; Kohli et al., MAbs. 7(4):752-8, 2015; Obrezanova et al., MAbs., 7(2):352-63, 2015; Wu et al, Protein Eng Des Sel., 28(10):403-14, 2015; Yang et al., MAbs., 9(4):646-53, 2017; Xu et al., Protein Eng Des Sel., 26(10):663-70, 2013; and Kelly et al., MAbs., 9(7):1036-40, 2017) to yeast display sorting, and isolating those yeast displaying antibodies that correspond to the more "developable" phenotype selects for suitable CDRs that can then be combined to create highly functional libraries.

Examples of such selections include polyspecificity reagents, heparin or chaperones and only retaining those antibodies that do not bind such substances. Further stability increases can be generated by applying a heat shock step (Traxlmayr et al., 2012; Shusta et al., J Mol Biol. 292(5): 949-56, 1999; Traxlmayr et al., Biochim Biophys Acta., 1824(4):542-9, 2012; Traxlmayr et al., Protein Eng Des Sel., 26(4):255-65, 2013; and Hasenhindl et al., Protein Eng Des Sel., 26(10):675-82, 2013).

The sequences encoding functional members of the heavy chain CDR1, CDR2, and/or CDR3 can be used as templates for synthesizing nucleic acids coding for such functional members or used directly. The resultant nucleic acids can then be inserted into the VHH scaffold as described herein to produce antibody libraries as also described herein. In some embodiments, the antibody library disclosed herein is substantially free of non-functional members, e.g., having less than 10% (e.g., less than 8%, less than 5%, less than 3%, less than 1%, or lower) non-functional members.

C. Antibody Libraries

The antibody libraries described herein may comprise a plurality of nucleic acids encoding a population of antibody VHH domains collectively comprising a population of CDR1s, a population of CDR2s, and a population of CDR3s located at the CDR1 region, the CDR2 region, and the CDR3 region of a VHH gene and inserted at the corresponding CDR positions. Further, the amino acid sequences of the CDR1s, the CDR2s, and the CDR3s are from naturally-occurring antibodies and, at least 90% of the population of heavy chain CDR1s and at least 90% of the population of heavy chain CDR2s are completely free of members comprising liabilities.

In some embodiments, the antibody library described herein is a heavy chain or VHH library comprising a plurality of nucleic acids encoding a plurality of antibody heavy chain variable domains. In some examples, the heavy chain or VHH library may comprise at least $10^2$ diversity of heavy chain CDR1s (having at least $10^2$ unique heavy chain CDR1 sequences), for example, at least $10^3$, $10^4$, $10^5$ diversity or at least $10^6$ diversity. Alternatively, or in addition, the heavy chain or VHH library may comprise at least $10^2$ diversity of heavy chain CDR2s (having at least $10^2$ unique heavy chain CDR2 sequences), for example, at least $10^3$, $10^4$, $10^5$ diversity or at least $10^6$ diversity. In other examples, the heavy chain or VHH library may comprise at least $10^2$ diversity of heavy chain CDR3s (having at least $10^2$ unique heavy chain CDR3 sequences), for example, at least $10^3$, $10^4$, $10^5$ diversity, at least $10^6$ diversity, at least $10^7$ diversity, or at least $10^8$ diversity.

In some examples, the heavy chain or VHH library may comprise diversity only in the heavy chain CDR1s, or the heavy chain CDR2s. In one specific example, the heavy chain or VHH library comprises diversity in all of the heavy chain CDR1, CDR2, and CDR3 regions.

In some embodiments, the heavy chain or VHH library is a secondary library generated for affinity maturation of a pre-selected antibody (the parent antibody) with binding activity to a target antigen. Such a secondary library may comprise diversity in one or two of the heavy chain CDR regions, while keeping the other CDR sequence(s) of the parent antibody. For example, the secondary library may comprise the same heavy CDR1 and CDR2 sequences as the parent antibody, and a diverse population of heavy chain CDR3 sequences. Alternatively, the secondary library may comprise the same heavy CDR3 sequence as the parent antibody and a diverse population of heavy chain CDR1 and/or CDR2 sequences.

II. Antibody Library Screening

Any of the antibody libraries described herein may be used to screen for antibodies having binding specificity to an antigen of interest. Antibodies encoded by the nucleic acids in the library can be expressed and displayed using a suitable expressing/display system, for example, a cell-free display system (e.g., ribosome display), a phage display system, a prokaryotic cell-based display system (e.g., bacterial display), or a eukaryotic cell-based display system (e.g., yeast display or mammalian cell display). In certain embodiments, the antibody libraries are expressed and displayed on yeast cells. In other embodiments, the antibody libraries are expressed and displayed on phage particles (phage display). In other embodiments two or more display systems are used, e.g. phage display followed by yeast display.

The library of antibodies may be expressed/displayed in a suitable system, e.g., those described herein, in any format.

Phage display is a protein display format using bacteriophages (e.g., phage fl, fd, and M13). In this system, at least one antibody chain (e.g., the heavy chain) is typically covalently linked to a bacteriophage coat protein, for example, a gene III protein, a gene VIII protein, or a major coat protein (see, e.g., WO 00/71694). Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mot Biol* 226:889-896; Clackson et al. (1991)

*Nature* 352:624-628; Gram et al. (1992) *PNAS* 89:3576-3580; Garrard et al. (1991) *Bio/Technology* 9:1373-1377; and Hoogenboom et al. (1991) *Nuc Acid Res* 19:4133-4137.

Bacteriophage displaying the protein component can be grown and harvested using standard phage preparatory methods, e.g., PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

In other embodiments, a eukaryotic expression/display system, e.g., yeast cells or mammalian cells, can be used for expressing and displaying the library of VHHs as described herein. Yeast display is a protein display format, in which a protein component (e.g., an antibody component) is linked to a yeast cell wall protein (e.g., Aga1p or Aga2p) directly or indirectly. In some instances, the VHH can be covalently fused to the yeast cell wall protein for direct display. In other instances, the association between the VHH and a yeast cell wall component can be mediated by an intermediate agent. Yeast display is described in, e.g., Cho et al., J. Immunol. Methods, 220(1-2):179-188, 1998; Boder et al., Methods Enzymol. 192(2):243-248, 2000; van den Beucken et al., FEBS Lett 546(2-3):288-294, 2003; and Boder et al., Arch Biochem Biophys 526(2):99-106, 2012.

To screen a VHH library as described herein for isolating VHHs capable of binding to a target antigen, the library of VHHs can be in contact with the target antigen under suitable conditions allowing for antibody-antigen binding. Phage particles or host cells displaying VHHs binding to the target antigen can be isolated, for example, by retention or a support member on which the target antigen is immobilized, amplified if needed, and the nucleic acids coding for the displayed VHHs can be determined. The screening process can be repeated multiple time, and display systems can be used in combination. When needed different antigens can be used for selecting VHH members having desired binding specificity or for negative selection to exclude VHH members having binding activity to a non-target antigen.

The screening of the VHHs derived from the libraries described herein can be carried out by any appropriate means. For example, binding activity can be evaluated by standard immunoassay and/or affinity chromatography. Determining the ability of candidate VHHs to bind therapeutic targets can be assayed in vitro using, e.g., a BIACORE™ instrument, which measures binding rates of a VHH to a given target antigen based on surface plasmon resonance. In vivo assays can be conducted using any of a number of animal models and then subsequently tested, as appropriate, in humans. Cell-based biological assays are also contemplated.

A lead VHH identified from VHH library screening may be subject to affinity maturation as described herein. A secondary library resulting from affinity maturation may be screened for binders having desired features, e.g., high binding affinity and/or binding specificity, following routine practice and/or disclosures provided herein.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology, Humana Press; Cell Biology: A Laboratory Notebook* (J. E. Cellis, ed., 1989) Academic Press; Animal Cell Culture (R. I. Freshney, ed. 1987); Introuction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; Animal Cell Culture (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Identifying Suitable VHH Molecules for Use as Framework Scaffolds This example describes choosing a suitable VHH framework scaffold for CDR insertions is crucial for creating highly diverse, highly functional single-domain antibody (sdAb) libraries. The usual rationale for selecting framework scaffolds are:

(i) the framework scaffolds are chosen from known antibodies;
(ii) the framework scaffolds are widely used by others;
(iii) the framework scaffolds contain germline sequences, which may or may not be consensus sequences;

Provided herein is an alternative approach for identifying suitable VHH for use as framework scaffolds for antibody library construction intended for therapeutic single domain antibody development. Five factors were taken into consideration:

(i) be currently approved for therapeutic use, or undergoing clinical trials;
(ii) have affinity for *Staphylococcus aureus* protein A to facilitate purification upon manufacturing. VHH domains are similar to human VH3 domains, many of which are known to have affinity to protein A;

(iii) lack cysteine residues, except for the canonical pair at framework 1 and framework 3 (Kabat positions 22 and 92);

(iv) have an arginine residue at framework 2 as opposed to the canonical leucine residue present in the VH/VL interface in human antibodies (Kabat position 45);

(v) have the canonical tryptophan residues as the first residue of framework 4 (Kabat position 103). In the final library this region will be sourced from human donors where the majority of sequences will have tryptophan residues at this position;

Nine therapeutic VHH domains were analyzed (Table 1), belonging to 7 different therapeutic molecules—some of which were multidomain/multi-specific (number indicates the domain analyzed). In addition, ozoralizumab, isecarosmab, sonelokimab, and vobarilizumab, all shared one domain targeting human serum albumin (HSA), which was analyzed only once. Protein A binding was predicted[1,2] based on the amino acid sequence (FIG. 1). Four therapeutic VHH domains—caplacizumab, isecarosmab (1), sonelokimab (3), and vobarilizumab (1) were selected as final framework scaffold choices (Table 2 and FIG. 2), since they satisfied the five requirements described above.

One of these (isecarosmab) was also synthesized with two framework mutations (V11L and L89V) making them identical to the other chosen frameworks, and the VH3-23 germline.

For each of the therapeutic antibodies listed in Table 2, three vectors were designed and synthesized, as described in Example 4. The diagrammatic representation of vectors encoding the original framework scaffold, the CDR1, and CDR2 framework scaffolds derived from the four original framework scaffolds listed in Table 2 is shown in FIG. 3. Naturally occurring replicated CDRs can be inserted into these selected exemplary antibody framework scaffolds.

TABLE 1

Analysis of Therapeutic VHH Antibodies.

| Name | Company | Clinical Status | Protein A binding (predicted) | Canonical Cysteines only | Canonical FWK2 | Canonical FWK4 |
|---|---|---|---|---|---|---|
| Caplacizumab | Ablynx | FDA Approved | Yes | Yes | Yes | Yes |
| Envafolimab | Tracon | Phase-III - active | Yes | No | Yes | No |
| Gontivimab | Ablynx | Phase II - abandoned | No | Yes | Yes | Yes |
| Isecarosmab (1) † | Merck | Phase I - active | Yes | Yes | Yes | Yes |
| Ozoralizumab (1) † | Ablynx | Phase III - active | Yes | Yes | No | No |
| Ozoralizumab (HSA)‡ | Ablynx | Phase III - active | Yes | Yes | No | No |
| Sonelokimab (1) † | Merck | Phase II - active | No | Yes | Yes | Yes |
| Sonelokimab (3) † | Merck | Phase II - active | Yes | Yes | Yes | Yes |
| Vobarilizumab (1) † | Ablynx | Phase II - active | Yes | Yes | Yes | Yes |

† Number indicates one VHH domain in a multidomain therapeutic VHH

‡HSA: human albumin binding domain. The domain is also present in isecarosmab, sonelokimab, and vobarilizumab, but is only analyzed once.

Example 2: Expression of the Chosen Framework Scaffolds on the Surface of Filamentous Bacteriophage Phage display technology consist of expressing foreign molecules on the surface of bacteriophages, more commonly the filamentous bacteriophage (M13). This technique is widely used for the development of antibodies. To evaluate the suitability of the four selected framework scaffolds to be used in conjunction with the aforementioned technology, four polynucleotides (Table 3) encoding VHH corresponding to each of the framework scaffolds (Table 3) were synthesized and inserted into a phage display vector (phagemid pDAN5). This vector contains a cloning site upstream of the g3 of the filamentous phage. Restriction enzyme sites for BssHII and NheI are inserted into the four polynucleotides, with a SV5 tag sequence downstream of the NheI site to aid in detection of recombinant protein expression.

TABLE 2

Summary of final framework scaffold choices.

| Name | Company | Clinical Status | Target | Closest Alpaca Germline | Alpaca FWK1-3 Identity | Closest Human Germline | Human FWK1-3 Identity |
|---|---|---|---|---|---|---|---|
| Caplacizumab | Ablynx | Approved 2018: Europe 2019: USA | von Willebrand factor | IGHV3-3 | 88% | IGHV3-23 | 86% |
| Isecarosmab (1) | Merck | Phase I active | ADAMTS L5 | IGHV3-3 | 89% | IGHV3-23 | 83% |

TABLE 2-continued

Summary of final framework scaffold choices.

| Name | Company | Clinical Status | Target | Closest Alpaca Germline | Alpaca FWK1-3 Identity | Closest Human Germline | Human FWK1-3 Identity |
|---|---|---|---|---|---|---|---|
| Isecarosmab (1) (a) | Merck | Phase I active | ADAMTS L5 | IGHV3-3 | 91% | IGHV3-23 | 85% |
| Sonelokimab (3) | Merck | Phase II active | IL-17A and IL-17F | IGHV3-3 | 93% | IGHV3-23 | 91% |
| Vobarilizumab (1) | Ablynx | Phase II active | IL6R | IGHV3S53 | 93% | IGHV3-23 | 89% |

(a) V11L and L89V, Kabat numbering.

TABLE 3

Nucelotide and amino acid sequence for the four exemplary parental scaffolds, flanked by BssHII and NheI restriction sites.

| Scaffold | DNA sequence | SEQ ID NO: |
|---|---|---|
| caplacizumab | gcgcgcatgccgaggtgcagctggt<br>agagtctgggggaggattggtgcag<br>cctggggctctctgagactctcct<br>gtgcagcctctggacgcaccttcag<br>ttacaatcccatgggctggttccgc<br>caggctccagggaaggggcgtgagc<br>ttgtagcagctattagcaggactgg<br>tggtagcacatactatccagactcc<br>gtggagggccgattcaccatctcca<br>gagacaacgccaagagaatggtgta<br>tctgcaaatgaacagcctgagagct<br>gaggacacggccgtttattactgtg<br>ctgctgctggtgttcgtgctgaaga<br>tggtcgtgttcgtaccctgccatct<br>gaatacaccttctggggccagggca<br>cccaggtcactgtctcctcagctag<br>c | 1 |
| isecarosmab 1 | gcgcgcatgccgacgtgcagctggt<br>agagtctgggggaggagtggtgcag<br>cctggggctctctgagactctcct<br>gtgcagcctctggacgcaccgtcag<br>tagctatgccatgggctggttccgc<br>caggctccagggaaggagcgtgagt<br>ttgtggcgggtattagcaggagtgc<br>tgaaagaacatattatgtagattcg<br>ctgaagggccgattcaccatctcca<br>gagacaactccaagaacacggtgta<br>tctgcaaatgaacagcctaagacca<br>gaggacacggccctttattactgtg<br>ctgctgatctggatccaaaccgtat<br>cttctctcgtgaagaatacgcttac<br>tggggccagggcaccctggtcactg<br>tctcctcagctagc | 2 |
| isecarosmab 1 (a) | gcgcgcatgccgacgtgcagctggt<br>agagtctgggggaggattggtgcag<br>cctggggctctctgagactctcct<br>gtgcagcctctggacgcaccgtcag<br>tagctatgccatgggctggttccgc<br>caggctccagggaaggagcgtgagt<br>ttgtggcgggtattagcaggagtgc<br>tgaaagaacatattatgtagattcg<br>ctgaagggccgattcaccatctcca<br>gagacaactccaagaacacggtgta<br>tctgcaaatgaacagcctaagacca<br>gaggacacggccgtttattactgtg<br>ctgctgatctggatccaaaccgtat<br>cttctctcgtgaagaatacgcttac<br>tggggccagggcaccctggtcactg<br>tctcctcagctagc | 57 |
| sonelokimab 3 | gcgcgcatgccgaggtgcagctggt<br>agagtctgggggaggattggtgcag<br>cctggggctctctgagactctcct<br>gtgcagcctctggacgcacctacga<br>tgccatgggctggctccgccaggct<br>ccagggaaggagcgtgagttcgttg<br>ctgctattagcgggagtggtgatga<br>cacatattacgcagactcagtgaag<br>ggccgattcaccatctccagagaca<br>actccaagaacacgctgtatctgca<br>aatgaacagcttaagaccagaggac<br>acggccgtttattactgtgctaccc<br>gtcgtggtctgtactacgtttggga<br>tgctaacgattacgaaaactggggc<br>cagggcaccctggtcactgtctcct<br>cagctagc | 3 |
| vobarilizumab 1 | gcgcgcatgccgaggtgcagctggt<br>agagtctgggggaggattggtgcag<br>cctggggctctctgagactctcct<br>gtgcagcctctggaagcgtcttcaa<br>aatcaatgtcatggcctggtaccgc<br>caggctccagggaaggggcgtgagc<br>tggtcgccggcattataagtggtgg<br>tagcacatcctatgcggattctgtg<br>aagggccgattcaccatctccagag<br>acaacgccaagaacacgctgtatct<br>gcaaatgaacagcctaagacccgag<br>gacacggccgtttattactgtgctt<br>tcatcaccaccgaatctgattacga<br>tctgggtcgtcgttactggggccag<br>ggcaccctggtcactgtctcctcag<br>ctagc | 4 |

TABLE 3-continued

Nucelotide and amino acid sequence for the four exemplary parental scaffolds, flanked by BssHII and NheI restriction sites.

| Scaffold | Amino Acid Sequence | SEQ ID NO: |
|---|---|---|
| caplacizumab | EVQLVESGGGLVQPGGSLRLSCAAS GRTFSYNPMGWFRQAPGKGRELVAA ISRTGGSTYYPDSVEGRFTISRDNA KRMVYLQMNSLRAEDTAVYYCAAAG VRAEDGRVRTLPSEYTFWGQGTQVT VSS | 53 |
| isecarosmab 1 | DVQLVESGGGVVQPGGSLRLSCAAS GRTVSSYAMGWFRQAPGKEREFVAG ISRSAERTYYVDSLKGRFTISRDNS KNTVYLQMNSLRPEDTALYYCAADL DPNRIFSREEYAYWGQGTLVTVSS | 54 |
| isecarosmab 1 (a) | DVQLVESGGGLVQPGGSLRLSCAAS GRTVSSYAMGWFRQAPGKEREFVAG ISRSAERTYYVDSLKGRFTISRDNS KNTVYLQMNSLRPEDTAVYYCAADL DPNRIFSREEYAYWGQGTLVTVSS | 58 |
| sonelokimab 3 | EVQLVESGGGLVQPGGSLRLSCAAS GRTYDAMGWLRQAPGKEREFVAAIS GSGDDTYYADSVKGRFTISRDNSKN TLYLQMNSLRPEDTAVYYCATRRGL YYVWDANDYENWGQGTLVTVSS | 55 |
| vobarilizumab 1 | EVQLVESGGGLVQPGGSLRLSCAAS GSVFKINVMAWYRQAPGKGRELVAG IISGGSTSYADSVKGRFTISRDNAK NTLYLQMNSLRPEDTAVYYCAFITT ESDYDLGRRYWGQGTLVTVSS | 56 |

(a) V11L and L89V, Kabat numbering.

Figure 4:
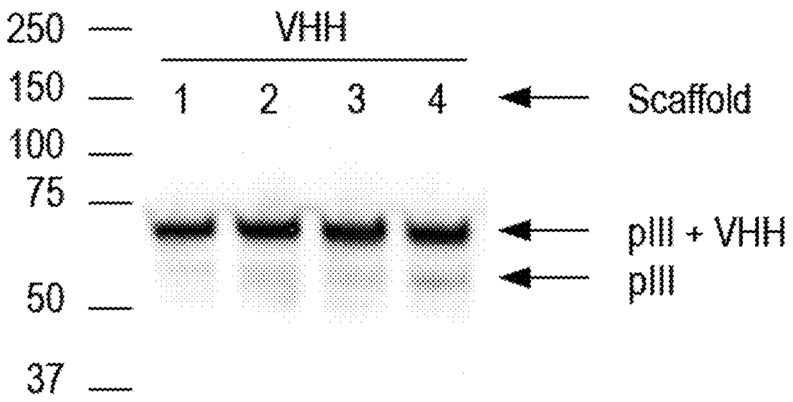
FIG. 4 is a western blot showing expression of the four VHH framework scaffolds in the phages.

The four constructs (VHH therapeutic framework scaffolds inserted into pDAN5) were transformed into *E. coli* bacteria (strain Omnimax 2) and phage particles were produced with the aid of the helper phage M13K07. The display of the VHH by the phage was assessed by SDS-PAGE+ western blot using an antibody that specifically recognizes the SV5 expression tag (FIG. 4) and was confirmed by the observation of the pIII-VHH band.

Figure 5:
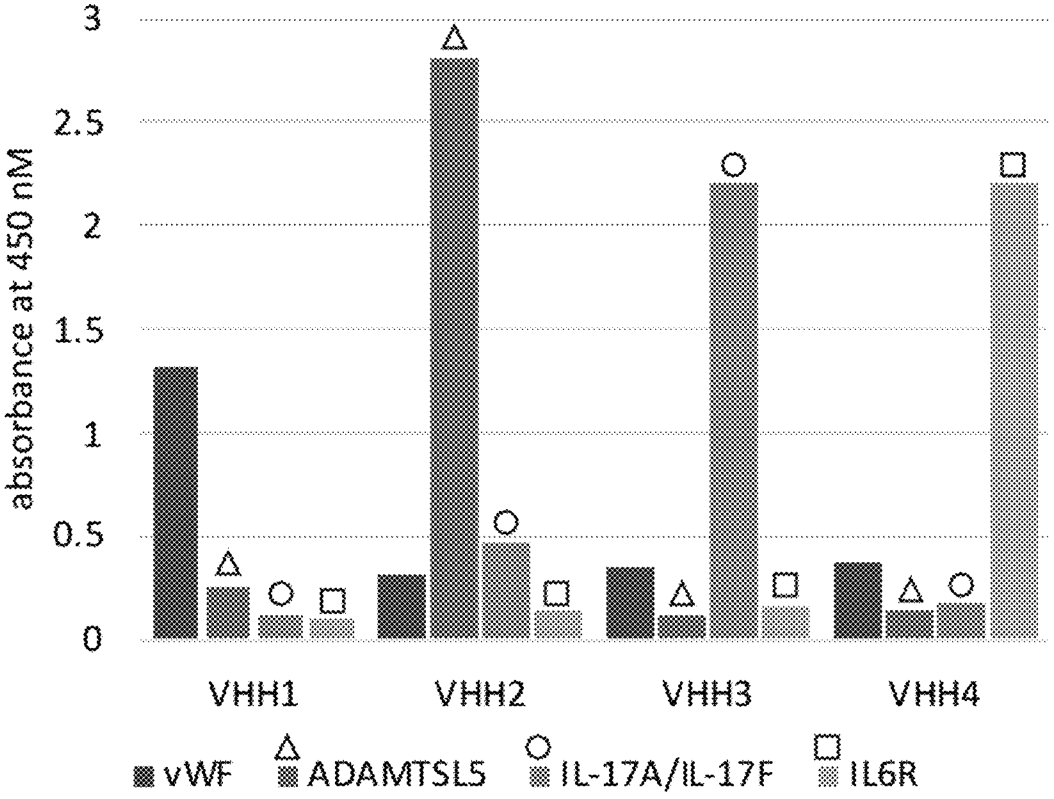
FIG. 5 shows binding of phage expressing the four VHH framework scaffolds to their respective targets by ELISA.

Phage particles were also used in an ELISA assay to detect framework scaffold binding to their respective targets. Targets vWF, ADAMTSL5, IL-17A/IL-17F or IL6R were immobilized on individually in wells of a 96-well microtiter plate. The wells were blocked using a PBST/5% milk, washed, and incubated with phage particles. After washing unbound phages, phage binding was determined by incubation with Horseradish peroxidase anti-M13 phage antibodies followed by visualization with TMB (3,3',5,5'-tetramethylbenzidine, Absorbance at 450 nm). Specific binding activity was observed for each framework scaffold against its intended target, with no binding observed against the other targets (FIG. 5).

Example 3: Expression of the Framework Scaffolds on the Surface of the Yeast

*Saccharomyces Cerevisiae*, and *Staphylococcus Aureus*—Protein A Binding Assessment by Flow Cytometry.

Yeast display technology consists of expressing foreign molecules on the surface of yeast cells, commonly the budding yeast *Saccharomyces cerevisiae*. This technique is widely used for the development of antibodies. To evaluate the suitability of the four selected parental framework scaffolds to be used in conjunction with the aforementioned technology, four polynucleotides encoding VHH (Table 3) corresponding to each of the framework scaffolds were inserted into a yeast display vector (plasmid pSYD). This vector contains a cloning site upstream of the AGA2 gene, comprised of the restriction enzyme sites for BssHII and NheI (inserted into the four polynucleotides) and an SV5 tag sequence downstream of the NheI site, useful for detection of the expression of the recombinant protein.

Figures 6, 6A, 6B, 6C, 6D, 6E, 6F:
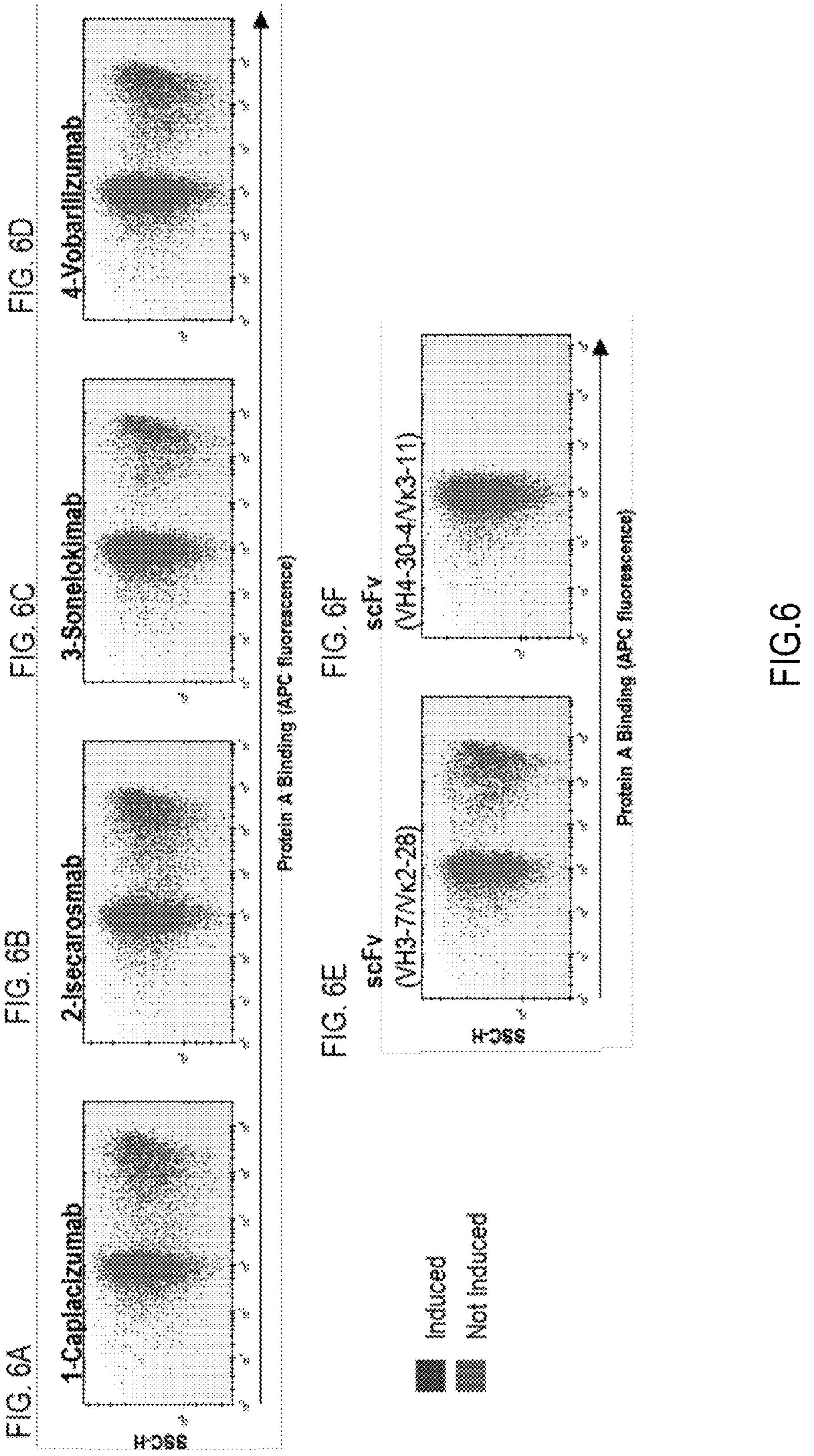
FIGS. 6A-6F shows flow cytometric analysis of VHH expression on the yeast cell surface using APC conjugated Protein A.

The four constructs (VHH framework scaffold inserted into pSYD) were transformed into *S. cerevisiae* (strain EBY100) and display of the VHH was induced using galactose. Display of VHH presentation on the yeast was measured by flow cytometry using allophycocyanin (APC) conjugated Protein A. As control, two different single-chain Fv (scFv) constructs were also used; one having a human VH3 heavy chain (positive control for protein A binding) and one having a human VH4 heavy chain (negative control for protein A binding). All four VHH framework scaffolds showed binding to protein A, indicated by the increase in fluorescence (shift of the population to the right on the X-axis). None of the non-induced cell populations showed binding to protein A, indicating that the observed signal is derived from inducible expression of VHH on the surface of the yeast cell (FIG. 6).

Example 4: Creating Vectors for Experimental CDR Screening

Figure 7:
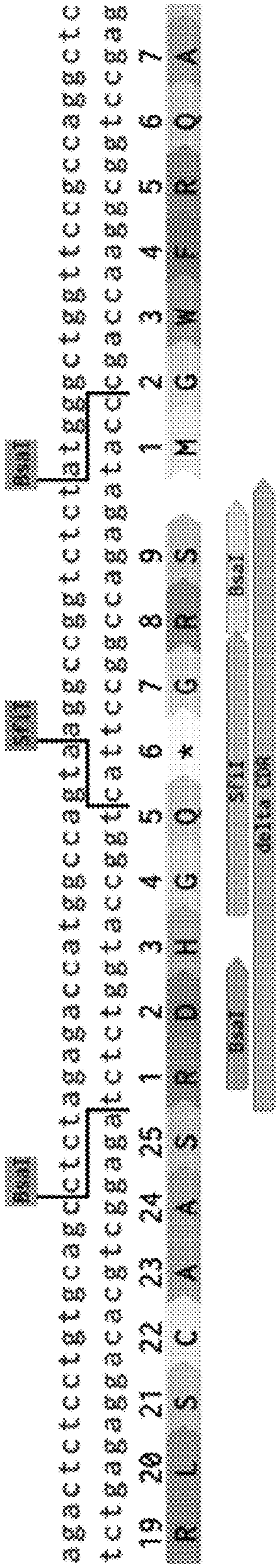
FIG. 7 shows a representation of opposite orientations of BsaI sites and SfiI site replacing a CDR in one of the constructs (SEQ ID NOs: 78 to 80, top to bottom).

For each of the four libraries created using the four framework scaffolds shown in Table 2, three polynucleotides encoding VHH corresponding to each of the framework scaffolds were synthesized. One of the three synthesized polynucleotides encodes for the non-modified VHH (parental) (Example 3), and the other two polynucleotides were modified to have one of the original CDRs replaced by a combination of restriction sites including two inverted BsaI sites (a type IIs enzyme that cuts outside of its recognition sequence), an additional SfiI site to ensure cleavage of the vector and serve as a spacer between the BsaI sites, a frameshift and an ochre stop codon to prevent expression of background sequence (FIGS. 3 and 7). To prevent potential contamination of the final library with camelid CDR1 and CDR2 or with CDR1 and CDR2 containing sequence liabilities, these CDRs were replaced by close human homolog sequences free of sequence liabilities in the two polynucleotides containing the type II restriction sites.

Each of these modified polynucleotides encoding the framework scaffolds was cloned into a yeast display vector (pSYD plasmid), and the presence of the stop codon in this sequence prevented the expression of the framework scaffold on the yeast surface until the deleted CDR is replaced with a functional CDR. The nucleotide and amino acid sequences of the exemplary framework scaffold with the deleted CDRs are shown in Table 4. Due to codon degeneracy, alternative nucleotide sequences encoding the amino acid sequences shown in Table 4 can alternatively be used in the present invention.

TABLE 4

Sequence for the deleted CDR version for the four exemplary parental scaffolds, flanked by BssHII and NheI restriction sites.

| Scaffold | DNA sequence | SEQ ID NO: |
|---|---|---|
| caplacizumab ΔCDR1 | gcgcgcatgccgaggtgcagctggt agagtctgggggaggattggtgcag cctgggggctctctgagactctcct gtgcagcctctagagaccatggcca gtaaggccggtctctatgggctggt tccgccaggctccagggaaggggcg tgagcttgtagcagctatcagttgg agcggaggtagtacatactatccag actccgtggagggccgattcaccat ctccagagacaacgccaagagaatg gtgtatctgcaaatgaacagcctga gagctgaggacacgccgtttatta ctgtgctgctgctggtgttcgtgct gaagatggtcgtgttcgtaccctgc catctgaatacaccttctggggcca gggcacccaggtcactgtctcctca gctagc | 5 |
| caplacizumab ΔCDR2 | gcgcgcatgccgaggtgcagctggt agagtctgggggaggattggtgcag cctgggggctctctgagactctcct gtgcagcctctggattcacctttag cagctatgccatgggctggttccgc caggctccagggaaggggcgtgagc ttgtagcagctagagaccatggcca gtaaggccggtctcttactatccag actccgtggagggccgattcaccat ctccagagacaacgccaagagaatg gtgtatctgcaaatgaacagcctga gagctgaggacacgccgtttatta ctgtgctgctgctggtgttcgtgct gaagatggtcgtgttcgtaccctgc catctgaatacaccttctggggcca gggcacccaggtcactgtctcctca gctagc | 6 |
| isecarosmab 1 ΔCDR1 | gcgcgcatgccgacgtgcagctggt agagtctgggggaggagtggtgcag cctgggggctctctgagactctcct gtgcagcctctagagaccatggcca gtaaggccggtctctatgggctggt tccgccaggctccagggaaggagcg tgagtttgtggcgggtatcagttgg agcggaggtagtacatattatgtag attcgctgaagggccgattcaccat ctccagagacaactccaagaacacg gtgtatctgcaaatgaacagcctaa gaccagaggacacggccctttatta ctgtgctgctgatctggatccaaac cgtatcttctctcgtgaagaatacg cttactggggccagggcaccctggt cactgtctcctcagctagc | 7 |
| isecarosmab 1 ΔCDR2 | gcgcgcatgccgacgtgcagctggt agagtctgggggaggagtggtgcag cctgggggctctctgagactctcct gtgcagcctctggattcacctttag cagctatgccatgggctggttccgc caggctccagggaaggagcgtgagt ttgtggcgggtagagaccatggcca gtaaggccggtctcttattatgtag attcgctgaagggccgattcaccat ctccagagacaactccaagaacacg gtgtatctgcaaatgaacagcctaa gaccagaggacacggccctttatta ctgtgctgctgatctggatccaaac cgtatcttctctcgtgaagaatacg cttactggggccagggcaccctggt cactgtctcctcagctagc | 8 |
| isecarosmab 1 (a) ΔCDR1 | gcgcgcatgccgacgtgcagctggt agagtctgggggaggattggtgcag cctgggggctctctgagactctcct gtgcagcctctagagaccatggcca gtaaggccggtctctatgggctggt tccgccaggctccagggaaggagcg tgagtttgtggcgggtatcagttgg agcggaggtagtacatattatgtag attcgctgaagggccgattcaccat ctccagagacaactccaagaacacg gtgtatctgcaaatgaacagcctaa gaccagaggacacggccgtttatta ctgtgctgctgatctggatccaaac cgtatcttctctcgtgaagaatacg cttactggggccagggcaccctggt cactgtctcctcagctagc | 59 |
| isecarosmab 1 (a) ΔCDR2 | gcgcgcatgccgacgtgcagctggt agagtctgggggaggattggtgcag cctgggggctctctgagactctcct gtgcagcctctggattcacctttag cagctatgccatgggctggttccgc caggctccagggaaggagcgtgagt ttgtggcgggtagagaccatggcca gtaaggccggtctcttattatgtag attcgctgaagggccgattcaccat ctccagagacaactccaagaacacg gtgtatctgcaaatgaacagcctaa gaccagaggacacggccgtttatta ctgtgctgctgatctggatccaaac cgtatcttctctcgtgaagaatacg cttactggggccagggcaccctggt cactgtctcctcagctagc | 60 |
| sonelokimab 3 ΔCDR1 | gcgcgcatgccgaggtgcagctggt agagtctgggggaggattggtgcag cctgggggctctctgagactctcct gtgcagcctctagagaccatggcca gtaaggccggtctctatgggctggc tccgccaggctccagggaaggagcg tgagttcgttgctgctatcagttgg agcggaggtagtacatattacgcag actcagtgaagggccgattcaccat ctccagagacaactccaagaacacg ctgtatctgcaaatgaacagcttaa gaccagaggacacggccgtttatta ctgtgctacccgtcgtggtctgtac tacgtttgggatgctaacgattacg aaaactggggcagggcaccctggt cactgtctcctcagctagc | 9 |

TABLE 4-continued

Sequence for the deleted CDR version for the four exemplary parental scaffolds, flanked by BssHII and NheI restriction sites.

| Scaffold | DNA sequence | SEQ ID NO: |
|---|---|---|
| sonelokimab 3 ΔCDR2 | gcgcgcatgccgaggtgcagctggt<br>agagtctgggggaggattggtgcag<br>cctggggctctctgagactctcct<br>gtgcagcctctggattcacctttag<br>cagctatgccatgggctggctccgc<br>caggctccagggaaggagcgtgagt<br>tcgttgctgctagagaccatggcca<br>gtaaggccggtctcttattacgcag<br>actcagtgaagggccgattcaccat<br>ctccagagacaactccaagaacacg<br>ctgtatctgcaaatgaacagcttaa<br>gaccagaggacacggccgtttatta<br>ctgtgctacccgtcgtggtctgtac<br>tacgtttgggatgctaacgattacg<br>aaaactggggccagggcaccctggt<br>cactgtctcctcagctagc | 10 |
| vobarilizumab 1 ΔCDR1 | gcgcgcatgccgaggtgcagctggt<br>agagtctgggggaggattggtgcag<br>cctggggctctctgagactctcct<br>gtgcagcctctagagaccatggcca<br>gtaaggccggtctctatggcctggt<br>accgccaggctccagggaaggggcg<br>tgagctggtcgccggcatcagttgg<br>agcggaggtagtacatcctatgcgg<br>attctgtgaagggccgattcaccat<br>ctccagagacaacgccaagaacacg<br>ctgtatctgcaaatgaacagcctaa<br>gacccgaggacacggccgtttatta<br>ctgtgctttcatcaccaccgaatct<br>gattacgatctgggtcgtcgttact<br>ggggccagggcaccctggtcactgt<br>ctcctcagctagc | 11 |
| vobarilizumab 1 ΔCDR2 | gcgcgcatgccgaggtgcagctggt<br>agagtctgggggaggattggtgcag<br>cctggggctctctgagactctcct<br>gtgcagcctctggattcacctttag<br>cagctatgccatggcctggtaccgc<br>caggctccagggaaggggcgtgagc<br>tggtcgccggcagagaccatggcca<br>gtaaggccggtctcttcctatgcgg<br>attctgtgaagggccgattcaccat<br>ctccagagacaacgccaagaacacg<br>ctgtatctgcaaatgaacagcctaa<br>gacccgaggacacggccgtttatta<br>ctgtgctttcatcaccaccgaatct<br>gattacgatctgggtcgtcgttact<br>ggggccagggcaccctggtcactgt<br>ctcctcagctagc | 12 |

(a) V11L and L89V, Kabat numbering.

Example 5: Generating a Database of CDR Sequences and Informatic Elimination of CDRs Demonstrating Potential Liabilities To generate a database of naturally occurring CDRs (CDRs found in naturally occurring antibodies such as human antibodies), next-generation sequencing (NGS) of the variable genes derived from a total of 40 human donors, divided into 4 pools of 10 donors (pools A-D), was carried out. B cells bearing CD19+ on their surface were purified from leukopaks using magnetic beads. Total RNA was extracted from the cells, subsequently, polyA+RNA was isolated and reverse transcribed using primers specific to the CH1 region of human IgG and IgM. The heavy chain variable regions were amplified by PCR, gel purified and sequenced using Novaseq SP 2×250 nucleotides, paired-end sequencing. After merging the paired-end reads and applying quality filters, more than 227 million reads were obtained (Table 5). Analysis of the variable gene sequences allowed identification of the numbers of CDRs shown in Table 6.

TABLE 5

Number of assembled reads obtained for each donor pool

| Donor Pool | Number of reads |
|---|---|
| A | 46,165,397 |
| B | 65,679,340 |
| C | 58,225,356 |
| D | 57,884,346 |
| Grand Total | 227,954,439 |

TABLE 6

Exemplary sequence liabilities to be removed

| Type | Liability | Rule |
|---|---|---|
| Post-Translational | Glycosylation | NxS or NxT, where x is not P |
| | Asn Deamidation | NG, NN, NS, NT, GNF, GNG, GNT, GNY |
| | Asp Isomerization | DG, DS, DD |
| | Cysteine | Presence of Cys |
| | Hydrolysis | DP |
| | Gln deamidation | QG |
| Biophysical | Aromatic Trimer | Three aromatics in tandem (His, Phe, Trp, Tyr) |
| | Polyreactivity | GGG, RR, VV, VG, WW, WxW, YY |
| | Positive Charge | Charge > 1 at pH 7 |
| | Arginine | Presence of Arg (except R57) |
| | Hydrophobic | Hydropathy < 0 (Parker scale) |
| Manufacturing | Protein A Affinity | Position 57 is not T, K, or R |

Since VHH antibodies are similar to human VH3 antibodies, we chose to only include CDR1 and CDR2 sequences derived from human VH3 germlines. A total of 128,935 and 389,908 CDR1 and CDR2 sequences were identified, respectively. The IMGT CDR definition was used.

Example 6: Informatic Elimination of CDRs Arising from Sequencing Errors and CDRs Demonstrating Potential Sequence Liabilities Following the creation of the CDR database disclosed in Example 5 above, CDRs that may have arisen as a result of sequencing errors were also computationally eliminated. In general, the presence of a particular CDR in more pools indicates that it is more likely that it is real, and not the result of a sequencing error. Alternatively, the identified CDRs can also be compared to publicly available datasets to validate their existence. It is clear that different threshold numbers can be chosen depending upon the number of total reads, the number of different pools, and the number of total unique CDRs identified. In this case, we chose to keep CDR sequences found in at least three of our sequenced donor pools or, found in 2 of our sequenced donor pools plus at least 1 publicly available dataset or, found in 1 of our sequenced donor pools plus at least 2 publicly available datasets. After the elimination of CDR sequences not meeting the aforementioned criteria, a total of 70,093 and 149,962 CDR1 and CDR2 sequences remained, respectively.

Sequence liabilities are short amino acid sequences that have the potential to create biophysical liabilities in proteins that contain them. A list of exemplary liabilities is described in Table 6, and it is clear that additional sequence-based liabilities may be identified. The list of unique CDRs previously identified was examined for the occurrence of the listed liabilities, and all CDRs containing a liability were computationally eliminated from the list of unique CDRs. In addition, CDRs having an anomalous length (different from 8 amino acids) were also eliminated. Finally, a total of 22,062 and 16,704 CDR1 and CDR2 sequences remained, respectively. A logo representation of the final CDR1 and CDR2 sequences is shown in FIGS. 8A-8B. Additional, or different, sequence liabilities in any combination may be similarly eliminated from databases of CDRs, so providing a list of CDRs free of sequence liabilities.

Example 7: Synthesis and Amplification of Oligonucleotides Corresponding to Final CDRs Sequences encoding the amino acid sequences found in naturally occurring CDRs are termed naturally replicated CDRs. Oligonucleotides encoding naturally replicated CDRs corresponding to those identified for CDR1 and CDR2 after the elimination steps described in the above Examples were synthesized (Agilent Technologies, Inc., Santa Clara, CA). The CDR coding sequences in these oligonucleotides were flanked by 5' and 3' sequences homologous to the framework vectors, into which the CDR coding sequences were cloned. The homologous sequences were used for both amplification of the CDR encoding oligonucleotides, and insertion of the amplified oligonucleotides into the yeast display vectors.

The pool of replicated natural CDRs amplified using primer pairs specific for each library framework scaffold and CDR position, cloned into the yeast display vectors described in Example 4 by homologous recombination, resulted in eight different single CDR loop libraries (two libraries per framework scaffold—CDR1-2).

The pool of oligonucleotides was subjected to amplification using the following primers:

For CDR1: primers identified with HCDR1-F and HCDR1-R in Table 7

For CDR2: primers identified with HCDR2-F and HCDR2-R in Table 7

The exemplary amplification primer sequences and assembly primer sequences are provided in Tables 7 and 8 respectively.

TABLE 7

Exemplary Amplification Primers.

| Name | Sequence-5' to 3' | SEQ ID NO: |
|---|---|---|
| 1-caplacizumab-HCDR1-F | GTGCAGCCTGGGGGCTCTCTGAGACTCTCCTGTGCAGCCTCT | 13 |
| 1-caplacizumab-HCDR1-R | AAGCTCACGCCCCTTCCCTGGAGCCTGGCGGAACCAGCCCAT | 14 |
| 1-caplacizumab-HCDR2-F | TTCCGCCAGGCTCCAGGGAAGGGGCGTGAGCTTGTAGCAGCT | 15 |
| 1-caplacizumab-HCDR2-R | TCTGGAGATGGTGAATCGGCCCTCCACGGAGTCTGGATAGTA | 16 |
| 2-isecarosmab1-HCDR1-F | GTGCAGCCTGGGGGCTCTCTGAGACTCTCCTGTGCAGCCTCT | 17 |
| 2-isecarosmab1-HCDR1-R | AAACTCACGCTCCTTCCCTGGAGCCTGGCGGAACCAGCCCAT | 18 |
| 2-isecarosmab1-HCDR2-F | TTCCGCCAGGCTCCAGGGAAGGAGCGTGAGTTTGTGGCGGGT | 19 |
| 2-isecarosmab 1-HCDR2-R | TCTGGAGATGGTGAATCGGCCCTTCAGCGAATCTACATAATA | 20 |
| 3-sonelokimab3-HCDR1-F | GTGCAGCCTGGGGGCTCTCTGAGACTCTCCTGTGCAGCCTCT | 21 |
| 3-sonelokimab3-HCDR1-R | GAACTCACGCTCCTTCCCTGGAGCCTGGCGGAGCCAGCCCAT | 22 |
| 3-sonelokimab3-HCDR2-F | CTCCGCCAGGCTCCAGGGAAGGAGCGTGAGTTCGTTGCTGCT | 23 |
| 3-sonelokimab3-HCDR2-R | TCTGGAGATGGTGAATCGGCCCTTCACTGAGTCTGCGTAATA | 24 |
| 4-vobarilizumab1-HCDR1-F | GTGCAGCCTGGGGGCTCTCTGAGACTCTCCTGTGCAGCCTCT | 25 |
| 4-vobarilizumab1-HCDR1-R | CAGCTCACGCCCCTTCCCTGGAGCCTGGCGGTACCAGGCCAT | 26 |
| 4-vobarilizumab1-HCDR2-F | TACCGCCAGGCTCCAGGGAAGGGGCGTGAGCTGGTCGCCGGC | 27 |

TABLE 7-continued

| Exemplary Amplification Primers. | | |
|---|---|---|
| Name | Sequence-5' to 3' | SEQ ID NO: |
| 4-vobarilizumab1-HCDR2-R | TCTGGAGATGGTGAATCGGCCCTTCACAGAATCCGCATAGGA | 28 |
| F-L1-HCDR3 | CTGTCTTCTCTGAAATCTGAGGACACGGCCGTGTATTACTGT | 29 |
| F-L3-HCDR3 | ATGAACTCTCTGCGTGCCGAGGACACGGCTGTGTATTACTGT | 30 |
| F-L4-HCDR3 | GTTAACTCTGTTACCGCCGCGGACACGGCTGTGTATTACTGT | 31 |
| JH-universal | GAAAAGGGTTGGGGCGGATGCGCTAGCTGAGGAGACGGTGACC | 32 |

TABLE 8

| Exemplary Assembly Primers | | |
|---|---|---|
| Name | Sequence-5' to 3' | SEQ ID NO: |
| 1-caplacizumab-HCDR1-ASS-R | AGCTGCTACAAGCTCACGCC | 33 |
| 1-caplacizumab-HCDR2-ASS-F | ATGGGCTGGTTCCGCCAGGC | 34 |
| 1-caplacizumab-HCDR2-ASS-R | ACAGTAATAAACGGCCGTGTCC | 35 |
| 1-caplacizumab-HCDR3-ASS-F | GCTGAGGACACGGCCGTTTATTACTGT | 36 |
| 2-isecarosmab1-HCDR1-ASS-R | ACCCGCCACAAACTCACGCT | 37 |
| 2-isecarosmab1-HCDR2-ASS-F | ATGGGCTGGTTCCGCCAGGC | 38 |
| 2-isecarosmab1-HCDR2-ASS-R | ACAGTAATAAAGGGCCGTGTCC | 39 |
| 2-isecarosmab1-HCDR3-ASS-F | CCAGAGGACACGGCCCTTTATTACTGT | 40 |
| 3-sonelokimab3-HCDR1-ASS-R | AGCAGCAACGAACTCACGCT | 41 |
| 3-sonelokimab3-HCDR2-ASS-F | ATGGGCTGGCTCCGCCAGGC | 42 |
| 3-sonelokimab3-HCDR2-ASS-R | ACAGTAATAAACGGCCGTGTCC | 43 |
| 3-sonelokimab3-HCDR3-ASS-F | CCAGAGGACACGGCCGTTTATTACTGT | 44 |
| 4-vobarilizumab1-HCDR1-ASS-R | GCCGGCGACCAGCTCACGCC | 45 |
| 4-vobarilizumab1-HCDR2-ASS-F | ATGGCCTGGTACCGCCAGGC | 46 |

TABLE 8-continued

| Exemplary Assembly Primers | | |
|---|---|---|
| Name | Sequence-5' to 3' | SEQ ID NO: |
| 4-vobarilizumab1-HCDR2-ASS-R | ACAGTAATAAACGGCCGTGTCC | 47 |
| 4-vobarilizumab1-HCDR3-ASS-F | CCCGAGGACACGGCCGTTTATTACTGT | 48 |

While the diversity found in CDR1-2 can be covered by array-based oligonucleotide synthesis relatively easily, this may not be the case for CDR3 where the original diversity can easily exceed $10^8$ different CDR3s. Even after liabilities and CDRs found fewer than 4 times are eliminated, the number of different HCDR3s can exceed $10_7$ if NovaSeq ($3\times10^9$ reads) is used to assess diversity. This can be addressed either by limiting synthetic HCDR3 diversity to $<10^6$ sequences, which is tractable by array-based synthesis; or by combining synthetic CDR1-2 diversity with naturally diverse HCDR3 amplified from donor lymphocytes.

To insert natural HCDR3 diversity from human antibodies into the VHH CDR3 site, RNA from B lymphocytes from Leuko Paks from ten donors, comprising a total of $>10^9$ B cells, was isolated using the Miltenyi STRAIGHTFROM LEUKOPAK CD19 kit. cDNA was prepared using a primer annealing in the IgM constant region. HCDR3s were amplified from the cDNA using forward primers (F-L1-HCDR3, F-L3-HCDR3, F-L4-HCDR3) and a reverse primer (JH-universal) described in Table 7. Next, the amplicons generated are reamplified with framework scaffold-specific forward primers described in Table 8 (HCDR3-ASS-F) and the JH-universal reverse primer—this amplification appends sequences to the 5' end homologous to the framework vectors, into which the HCDR3s are to be cloned.

Example 8: Creating a Replicated Diversity of Non-Redundant CDR3 for Insertion into the Library To insert naturally replicated HCDR3s into the VHH CDR3 site, a subset of sequenced HCDR3s, up to the synthesis limits of the array (or any other) based synthesis are identified. Presently, such limits are 1,000,000 sequences. Such HCDR3s are best chosen from a sequence database of HCDR3s by virtue of their difference one to another, to choose as broad a diversity as possible, given the limited diversity accessible using naturally replicated diversity. Machine learning or artificial intelligence is employed to identify subsets of HCDR3s which are as different from one another as possible.

Numerous methods known to those skilled in the art are available to identify the desired subset of HCDR3, such as unsupervised learning clustering algorithms like K-means, DBSCAN, OPTICS, BIRCH, hierarchical clustering, and others.

Figure 9:
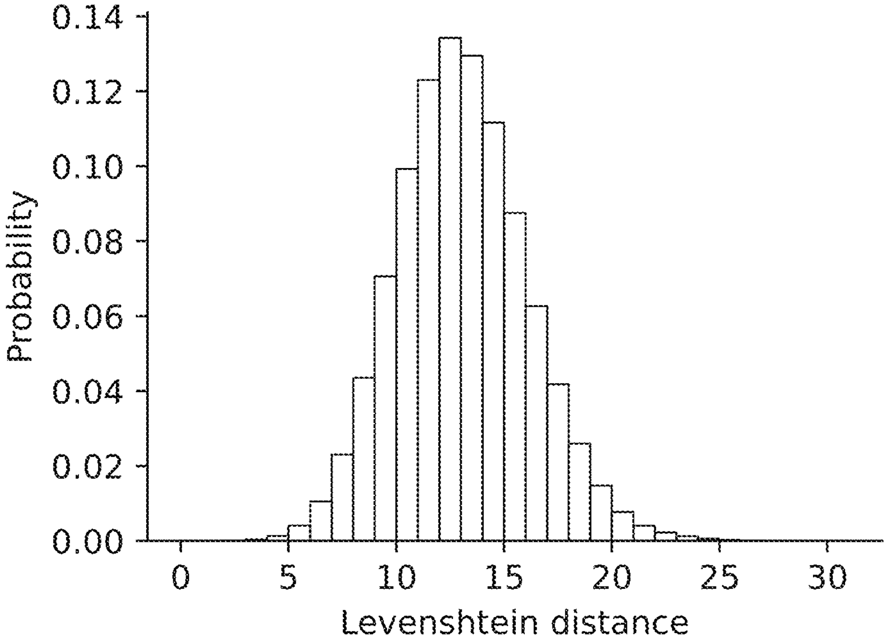
FIG. 9 shows a Levenshtein distance distribution between exemplary dataset of 10,000 naturally found HCDR3 sequences.
Figure 10:
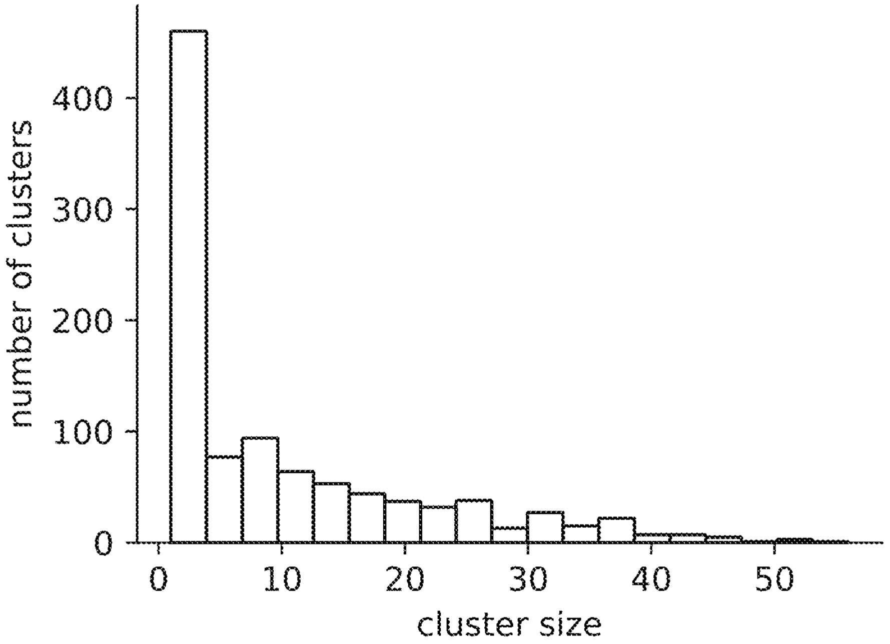
FIG. 10 shows a cluster size distribution of exemplary 1,000 clusters generated.

Exemplified here, 10,000 different HCDR3 amino acid sequences derived from next-generation sequencing of CD19+ B-cells were first assigned a distance score in relation to every other sequence in the dataset. The distance metric used is the Levenshtein distance, but those skilled in the art can easily identify other appropriate metrics of similarity (e.g. Needleman-Wunsch alignment score) or dissimilarity (e.g. Hamming distance) to serve the same purpose. For the given dataset, the distribution of Levenshtein distance calculated can be seen in FIG. 9. Next, the scores were used to feed a modified version of the K-means clustering algorithm suited for large datasets ("Web Scale K-Means clustering" D. Sculley, Proceedings of the 19th international conference on World wide web (2010)), with the number of desired clusters set to 1,000 i.e. ten-fold less than the number of input sequences. A larger or smaller number of clusters can be specified depending on how much one wants to compress the dataset. In FIG. 10 the size distribution (number of HCDR3 per cluster) is shown. Almost 500 clusters contain only one sequence, meaning that these are mostly dissimilar to others in the dataset. Larger clusters are also formed, with the biggest having 52 different HCDR3 sequences. Two exemplary HCDR3 clusters are represented in FIGS. 11A and 11B.

A single sequence from each cluster can be selected to be included in the library. Many forms of choosing the representative can be used by those skilled in the art, such as the sequence that is the closest to the cluster consensus and doesn't have any sequence liabilities, such as the ones specified in Example 6. The clustering process can be repeated with larger datasets or with similar sized datasets until the upper limit that can be practically synthesized is reached. Amplification of such sequences can be performed as described for CDR1 and CDR2 in Example 7.

Example 9: Cloning of CDRs into Single Site CDR Vectors and Selection for Functional CDRs Although natural replicated CDRs are synthesized based on criteria that should ensure their functionality (e.g., in frame, and removal of liabilities), oligonucleotide synthesis may not be 100% accurate. In addition to the problem of incorrect sequences, other unidentified liabilities causing poor expression or polyreactivity may be encoded by the synthesized oligonucleotides. The selection of functional CDRs can be an option to address this issue.

Each of the CDRs remaining from the elimination steps described above was cloned into the appropriate yeast display framework scaffold vector. The coding sequences of the exemplary framework scaffold are in Table 4.

Using CDR1 of library 1 as an example, the CDR1 framework scaffold vector was digested with BsaI and SfiI leaving a gap at the site of CDR1. The cleaved vector and the collection of CDR1 polynucleotides amplified as described in Example 7 were then simultaneously transformed together into yeast. Inside yeast cells, homologous recombination between the cleaved vector and the CDR1 polynucleotides results in the insertion of the CDR1 polynucleotides into the CDR1 framework scaffold vector. The entire population of CDR1 yeast framework scaffold vectors carrying each of the CDR1 polynucleotides identified above constitutes a CDR1 yeast display library (FIG. 3). For the CDR1 framework scaffold vector, all portions of the VHH domain are constant except for the CDR1 that is assessed. Selection for functional CDR1 was carried out by sorting for protein A binding. After the display of the VHH is induced, the yeast cells are incubated with magnetic beads covalently attached to protein A. The positive population (VHH binding protein A) is purified using MACS (magnetic-activated cell sorting). The higher the level of the VHH binding to protein A, the higher the probability of the cell-binding the nanoparticles—especially when competition is employed by having a total number of cells that far exceeds the binding capacity of the nanoparticles, thus, enriching for strong binding sequences.

Figure 12:
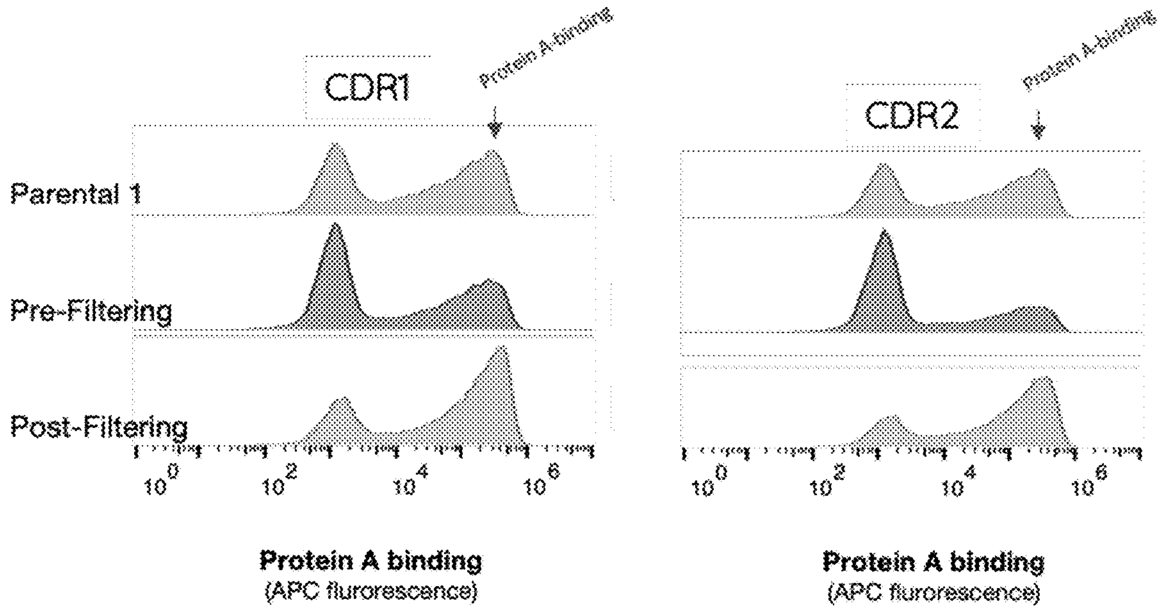
FIG. 12 shows flow cytometric analysis of Library 1-CDR1 and Library 1-CDR2 libraries, before and after sorting for protein A binding.
Figure 13:
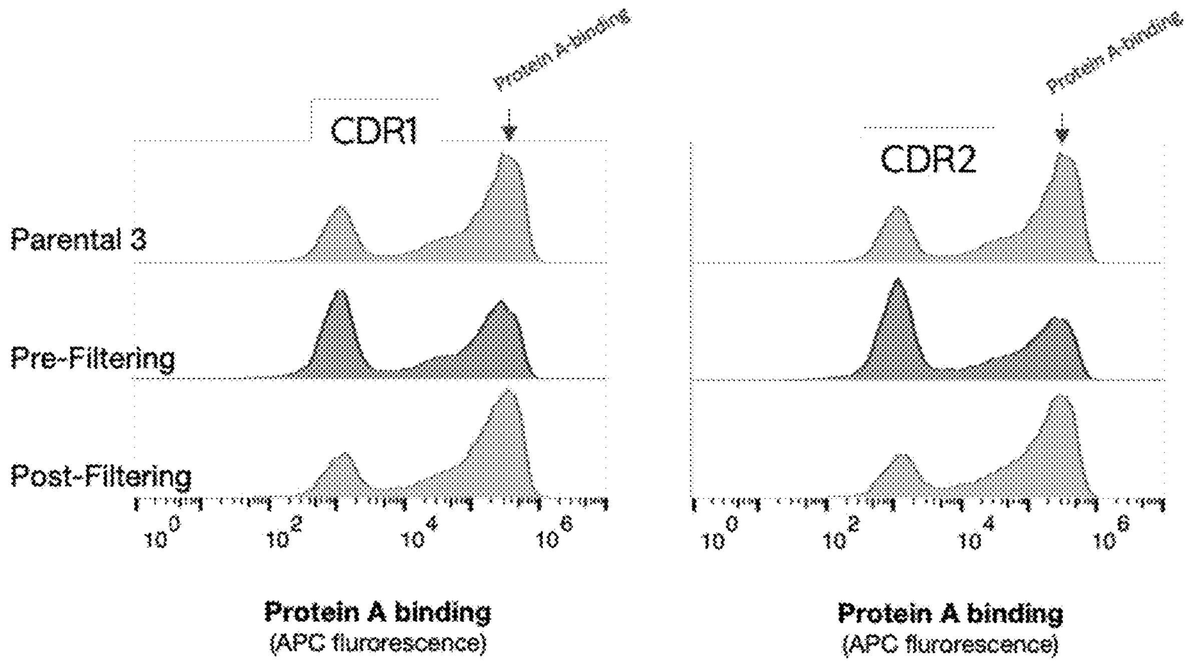
FIG. 13 shows flow cytometric analysis of Library 3-CDR1 and Library 3-CDR2 libraries, before and after sorting for protein A binding.

By sorting libraries of single CDRs by protein A affinity, in addition to the elimination of CDRs that might negatively affect the affinity of VHH to protein A, those CDRs that contain stop codons, frameshifts, or are poorly expressed may be eliminated as well. Effective display on the yeast surface has been previously correlated with improved stability and folding in diverse proteins (Cherf, G. M. and J. R. Cochran (2015). "Applications of Yeast Surface Display for Protein Engineering." Methods Mol Biol 1319: 155-175; Pavoor, T. V., et al., (2012) "An enhanced approach for engineering thermally stable proteins using yeast display." Protein engineering, design & selection: PEDS 25(10): 625-630; Pepper, L. R., et al., (2008). "A decade of yeast surface display technology: where are we now?" Comb Chem High Throughput Screen 11(2): 127-134). After each CDR library is sorted, DNA encoding well-expressed CDRs is obtained by isolating DNA from yeast cells expressing well folded CDRs. The non-filtered and filtered libraries for libraries 1 and 3 are shown in FIGS. 12 and 13. The populations are analyzed by flow cytometry and protein A binding levels (x-axis) are represented as a histogram. The analysis shows a clear improvement after enrichment, with libraries demonstrating binding levels similar to or exceeding that of the original parental molecule from which the framework scaffolds were generated.

In the examples provided here, we have sorted for improved protein A binding levels. However, a similar approach can be taken using any selective method that distinguishes yeast displaying antibodies with desirable properties (e.g. high expression, low polyreactivity, good developability) from yeast displaying antibodies with undesirable properties (e.g. low expression, high polyreactivity, poor developability). For example, to select antibodies with reduced polyreactivity, clones displaying VHH antibodies that do not bind to polyspecificity reagents would be selected. Examples of such polyspecificity reagents include those described previously (Hotzel, I. et al. A strategy for risk mitigation of antibodies with fast clearance. *MAbs* 4, 753-760, doi:10.4161/mabs.22189 (2012); Xu, Y. et al. Addressing polyspecificity of antibodies selected from an in vitro yeast presentation system: a FACS-based, high-throughput selection and analytical tool. *Protein Eng Des Sel* 26, 663-670, doi:10.1093/protein/gzt047 (2013); Kelly, R. L. et al. Chaperone proteins as single component reagents to assess antibody nonspecificity. *MAbs* 9, 1036-1040, doi:10.1080/19420862.2017.1356529 (2017).)

Example 10: Assembly of Full-Length VHH Library

Once each individual CDR library was screened for protein A binding (CDR1 and CDR2) or amplified from donor B-cells (CDR3), the CDRs were assembled into VHH domains containing diversity in all three CDRs. Individual CDRs and neighboring framework regions were amplified using the primers described in Table 8. The three individual fragments corresponding to CDR1, CDR2, and CDR3 (and its neighboring frameworks) for each library were assembled using overlap PCR to form the VHH chains, as shown in FIG. 3.

Example 11: Cloning into a Phage Display Vector (pDan5)

Once the VHH libraries were assembled, they were ligated into a phage display vector, such as pDAN5 to explore their functionality. This vector contains a cloning site upstream of the g3 of the filamentous phage, comprised of the restriction enzyme sites for BssHII and NheI. The VHH created in Example 10 contained the BssHII restriction site upstream of the VHH and the NheI downstream of the VHH. The PCR product was then digested with the same enzymes to generate cohesive ends. The pDAN5 plasmid was cultivated in *E. coli*, extracted by alkaline lysis, and purified by cesium chloride/ethidium bromide gradient. The plasmid was digested with the same enzymes and the backbone purified by agarose gel electrophoresis extraction followed by chromatography to remove contaminants. The backbone was ligated to the VHH library using T4 DNA ligase overnight at 16° C. The ligation was purified and electro-transformed into electro-competent *E. coli* TG1 cells. The transformed cells were plated out on agar plates containing carbenicillin, glucose, and sucrose to select for bacteria that received the plasmid. A combined total of $2.3\times10^{10}$ transformants was obtained (Table 9).

TABLE 9

Number of transformants obtained for each library after electrotransformation.

| Library | Transformants |
|---|---|
| Library 1 | $4.47\times10^{9}$ |
| Library 2 | $6.40\times10^{9}$ |
| Library 3 | $6.64\times10^{9}$ |
| Library 4 | $5.44\times10^{9}$ |
| Total | $2.30\times10^{10}$ |

Example 12: Creation of Bacteriophage Particles, Including Western Blot

The transformed bacteria were cultivated in a shaking flask containing liquid 2xYT media+carbenicillin+glucose (the glucose is to inhibit VHH expression) at 37° C. until an OD600 nm of 0.5 was reached. The bacteria were superinfected with M13KO7 helper phage (at a multiplicity of infection of 5) for 30 min at 37° C. without shaking and 30 min at 37° C. with shaking. The bacteria were centrifuged, the media removed and replaced with 2xYT media+carbenicillin+kanamycin and cultivated for 16 h at 25° C. in a shaker incubator.

Figures 14A, 14B:
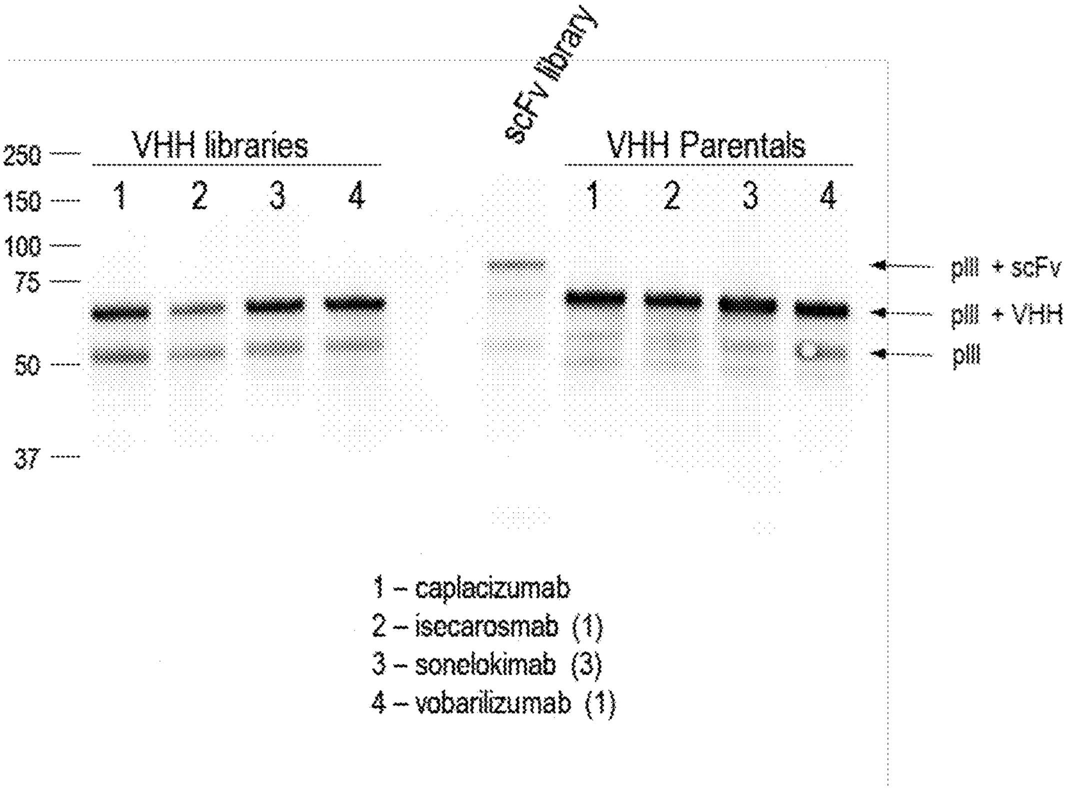
FIGS. 14A-14B show western blots of the libraries.

To recover the phage particles, the cultures were centrifuged to separate the bacteria and the supernatant, where the phage is found. The supernatant was mixed with a 20% PEG 8000+2.5 M NaCl solution at a 5:1 ratio. This causes the phage to precipitate, allowing them to be harvested by centrifugation. The supernatant was discarded, and the phage pellet was resuspended in a PBS solution. The display of the VHH by the phage was assessed by SDS-PAGE+ western blot using an antibody that specifically recognizes the expression tag (SV5) as shown in FIG. 14B.

Figure 15:
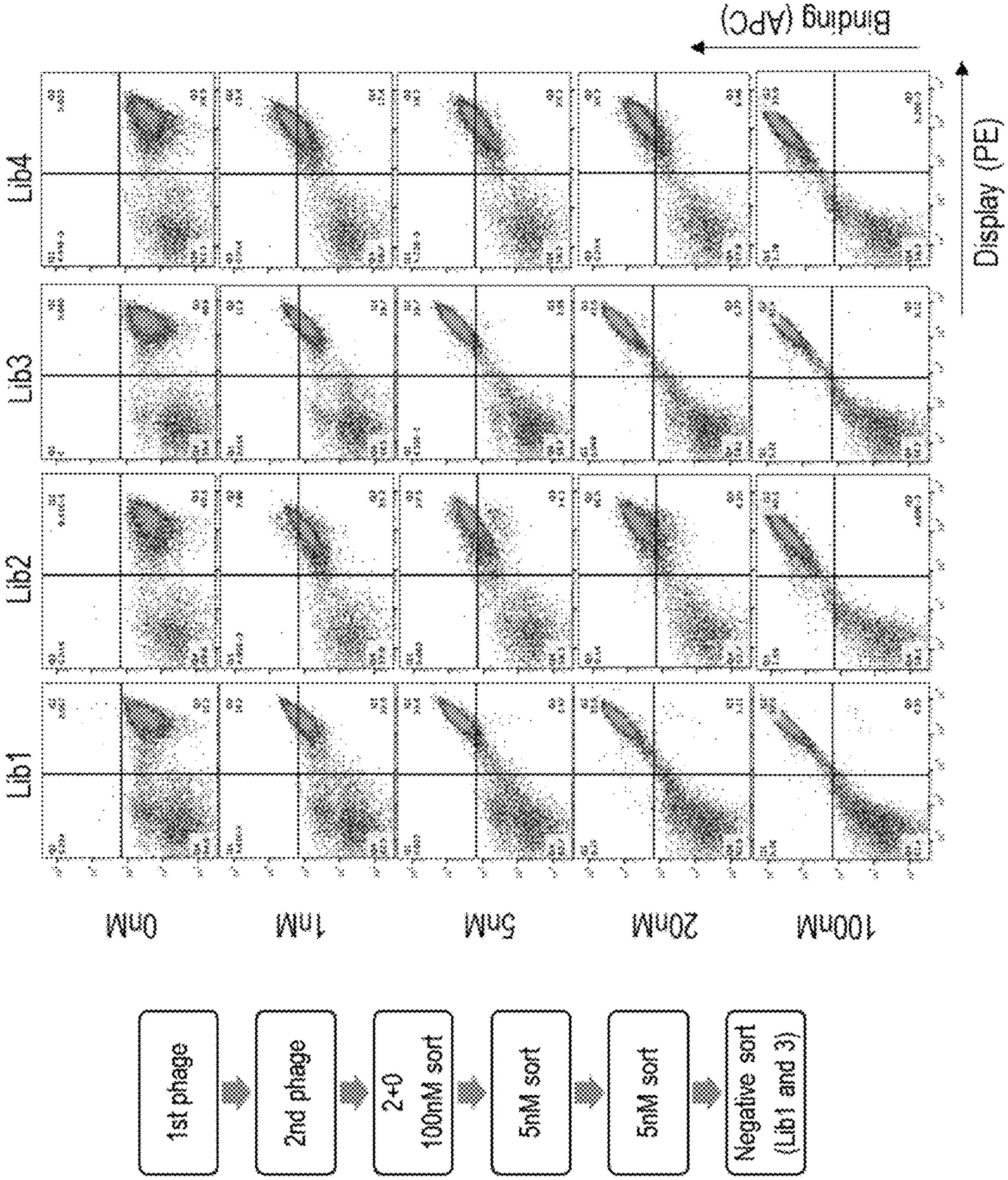
FIG. 15 shows flow cytometry data for Lib1, Lib2, Lib3 and Lib4 selected against human Interferon alpha.

Example 13: Antibody Selection Against Interferon-Alpha-2b by Combined Phage and Yeast Display Using the Library After construction and phage particle production, the library was screened against a target of interest. While selection can be carried out using phage display alone it is preferable to combine phage and yeast display technologies. 1012 phage particles displaying the VHH libraries were used in two rounds of selection against the biotinylated recombinant interferon-alpha using the Kingfisher magnetic bead system. $2\times10^{7}$ streptavidin-conjugated magnetic beads (Dynabeads M-280) coated with the biotinylated proteins (100-400 nM) were washed, coated with the antigen, incubated with the phage particles and washed again to remove non-binders. Phage particles were then eluted by reducing the pH and infecting F' pilus-carrying bacteria (Ominmax-2T1, Thermo Fisher Scientific). The phages were propagated, and the selection cycle was reiterated. After two rounds of phage enrichment, the VHH were PCR amplified and transferred to a C-terminal yeast display system by homologous recombination (pDNL6 yeast display vector), in which the VHH is displayed fused to the C terminus of Aga-2. The transformed yeast was then induced for VHH display by adding galactose to the culture media. The induced yeast mini-libraries were then used for another three rounds of enrichment against the biotinylated recombinant human antigen by fluorescence-activated cell sorting. Target concentration in the first sorting round was 100 nM, reduced to 5 nM in rounds 2 and 3. Two of the libraries underwent an additional negative selection round to remove streptavidin-binding clones. After these rounds of phage and yeast sorting enrichment, the recovered populations were analyzed by flow cytometry to test for binding against the antigens in decreasing concentration of antigen and in the absence of the antigen to check for non-specific binding to secondary reagents (FIG. 15). Results show that the library can successfully yield high-affinity binders to the antigen tested.

Example 14: Affinity Determination of Selected Antibodies

Affinity determination of antibodies selected from the naïve library using the phage +yeast display protocol described in Example 13, was performed following the approaches described herein. The binding affinity of the VHH antibody variants thus obtained to interferon-alpha was examined using a Carterra LSA machine. Briefly, the VHH populations were subcloned into the pDAN5 vector, transformed into *E. coli* Top10F' cells and soluble VHH molecules were produced. The supernatants from bacteria expressing the VHH proteins were immobilized on a Carterra LSA HC30M chip couple to anti-SV5 antibody. The chips were activated with 1:1:1 100 mM MES pH 5.5, 100 mM S-NHS, 400 mM EDC (all reconstituted in MES 5.5), and 100 μL of each were mixed in a vial immediately before running the assay. The monoclonal goat anti-SV5 IgG was immobilized at 50 μg/mL followed by deactivation with 1 M Ethanolamine pH 8.5.

The supernatants were diluted into HBSTE buffer and cycled for 5 minutes across the anti-SV5 surface. Antigens were tested in a four-fold dilution series starting at 150 nM. The antigen samples were tested from the lowest to the highest concentration. Data were processed using Carterra LSA software. Results were double referenced, cropped, and fitted using a 1:1 kinetic model with a fixed Rmax parameter and floating TO parameter. The highest antigen concentration injection was excluded to improve fits.

Figure 16:
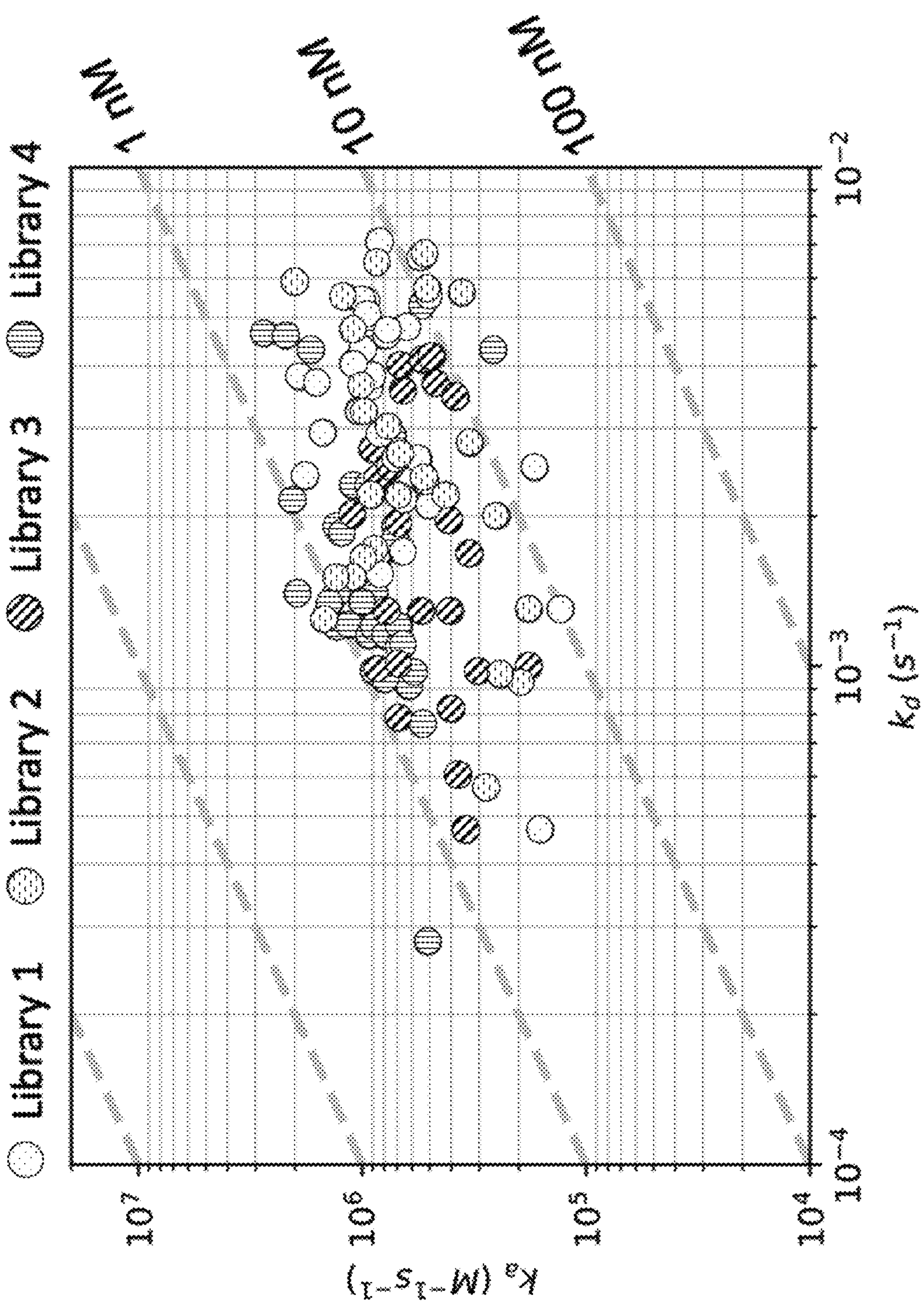
FIG. 16 shows association and dissociation rate of clones from all four libraries against interferon alpha measured by SPR.

As shown in FIG. 16, the affinities of antibodies selected directly from the library, constructed as described in Examples 1-12, are shown to be extremely potent, with the vast majority having affinities of less than 10 nM.

Example 15: Antibody Selection Against B7-H4 Protein by Combined Phage and Yeast Display Using the Library To further validate the library construction and concept, we selected againt another target of interest (B7-H4 protein).

Figure 17:
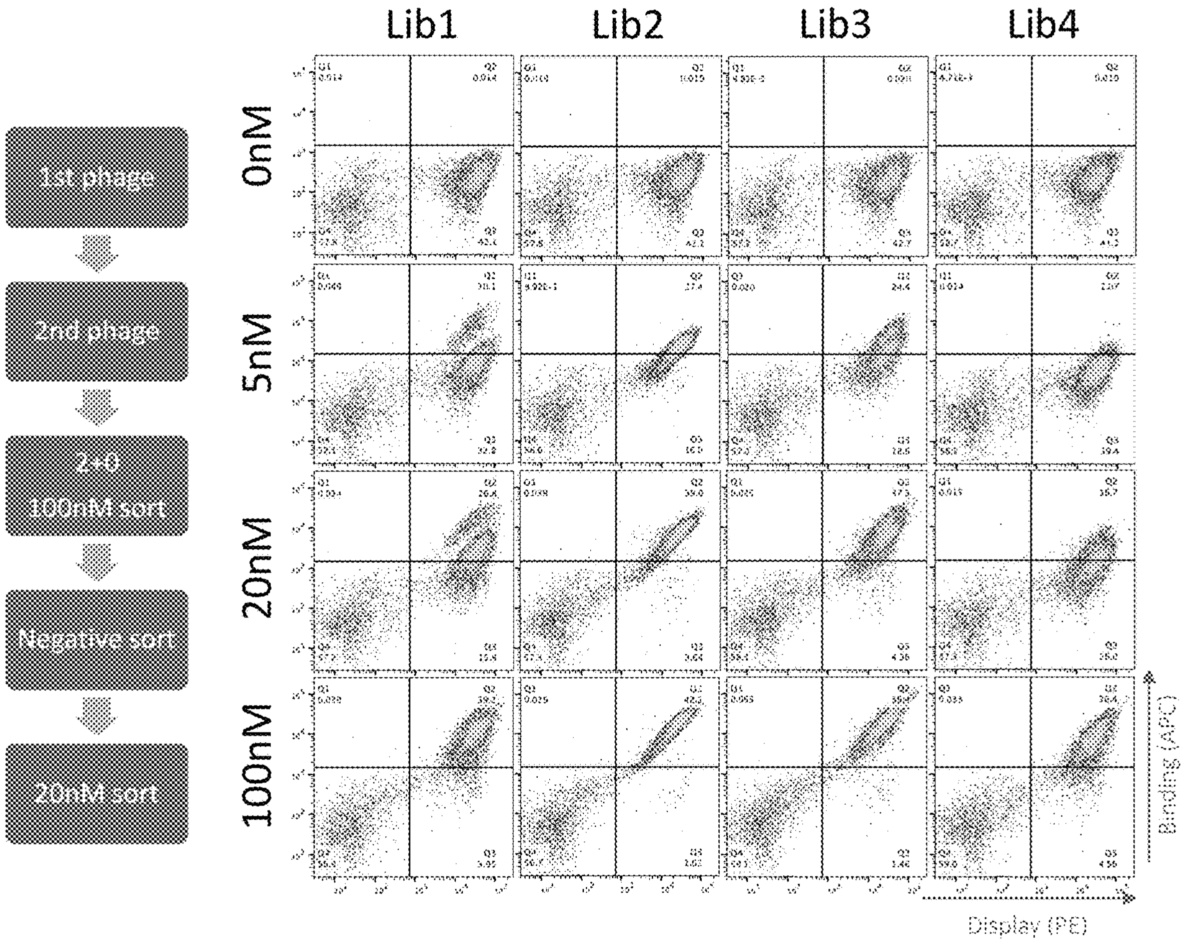
FIG. 17 shows flow cytometry data for Lib1, Lib2, Lib3 and Lib4 selected against human B7-H4.
Figure 18:
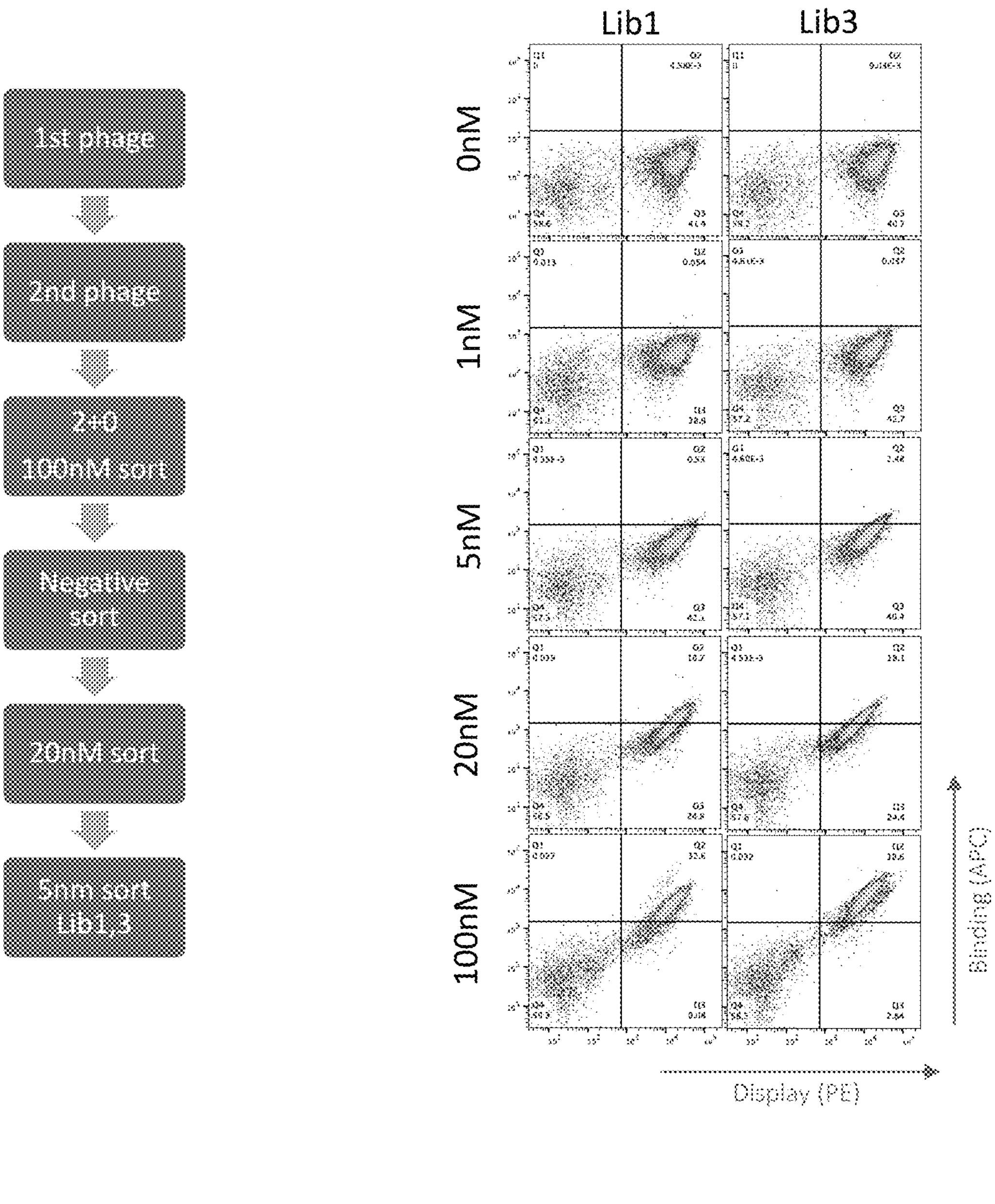
FIG. 18 shows flow cytometry data for Lib1 and Lib3 selected against human B7-H4.

A similar approach to that given in example 12 was followed. where phage particles were submitted to selection against the biotinylated antigen using similar protocols. After two rounds of phage enrichment, the VHH were PCR amplified and transferred to a C-terminal yeast display system by homologous recombination (pDNL6 yeast display vector), in which the VHH is displayed fused to the C terminus of Aga-2. The transformed yeast was then induced for VHH display by adding galactose to the culture media. The induced yeast mini-libraries were then used for another round of positive selection against the biotinylatd antigen at 100 nM concentration. This round was followed by a negative selection in which only clones not showing binding to the secondary reagents (anti-SV5 monoclonal antibody labeled with PE fluorophore and streptavidin labeled with AlexaFluor 633 fluorophore) were sorted. All four sublibraries were subjected to another positive selection round, now at antigen concentration equal to 20 nM and, after that, Libraries 1 and 3 were subject to another round of selection at antigen concentration equal to 5 nM. After these rounds of phage and yeast sorting enrichment, the recovered populations were analyzed by flow cytometry to test for binding against the antigens in decreasing concentration of antigen and in the absence of the antigen to check for non-specific binding to secondary reagents. The populations tested are the ones obtained after 2 positives and 1 negative round of yeast display selection (FIG. 17) and the ones obtained after 3 positives and 1 negative round of yeast display selection (FIG. 18). Results show that the library can successfully yield high-affinity binders to the antigen tested.

Example 16: Next-Generation Sequencing of Selected Yeast Populations Against the Antigens Interferon-Alpha and B7-H4

In order to identify the sequences present in a given selected population, one can apply low throughput DNA sequencing techniques such as the Sanger method or, alternatively, next-generation sequencing techniques such as those in the Illumina platforms and others. The latter is able to provide a far larger number of sequences, enabling better profiling of the selected populations. Selected populations from the interferon-alpha and B7-H4 selection campaigns, such as those exemplified in Table 10 were subject to next-generation sequencing using Illumina Miseq. The obtained sequences were annotated to identify the scaffold and CDR identities. Also, in order to identify more distinct clones, one can apply clustering techniques such as described in Example 8, or in the case of this example, clustering was performed by re-encoding CDR3 amino acid sequences to reflect their physicochemical characteristics, which were then compared to each other to quantify the Levenshtein distance, and finally clustered using the OPTICS method.

Figure 19:
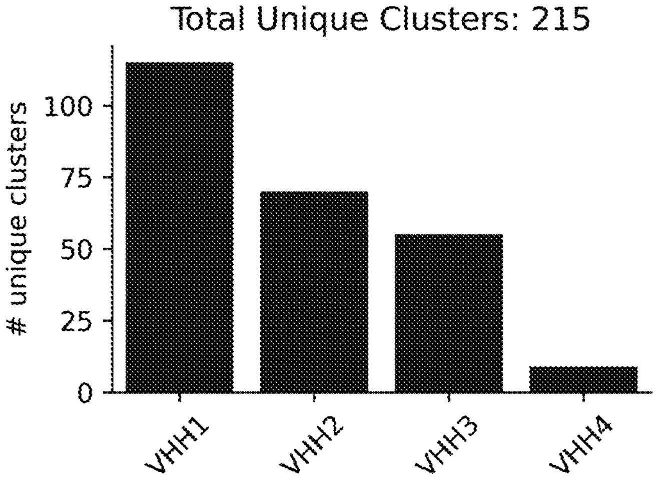
FIG. 19 shows the number of unique CDR3 cluster identified by next-generation sequencing against huma B7-H4.
Figure 20:
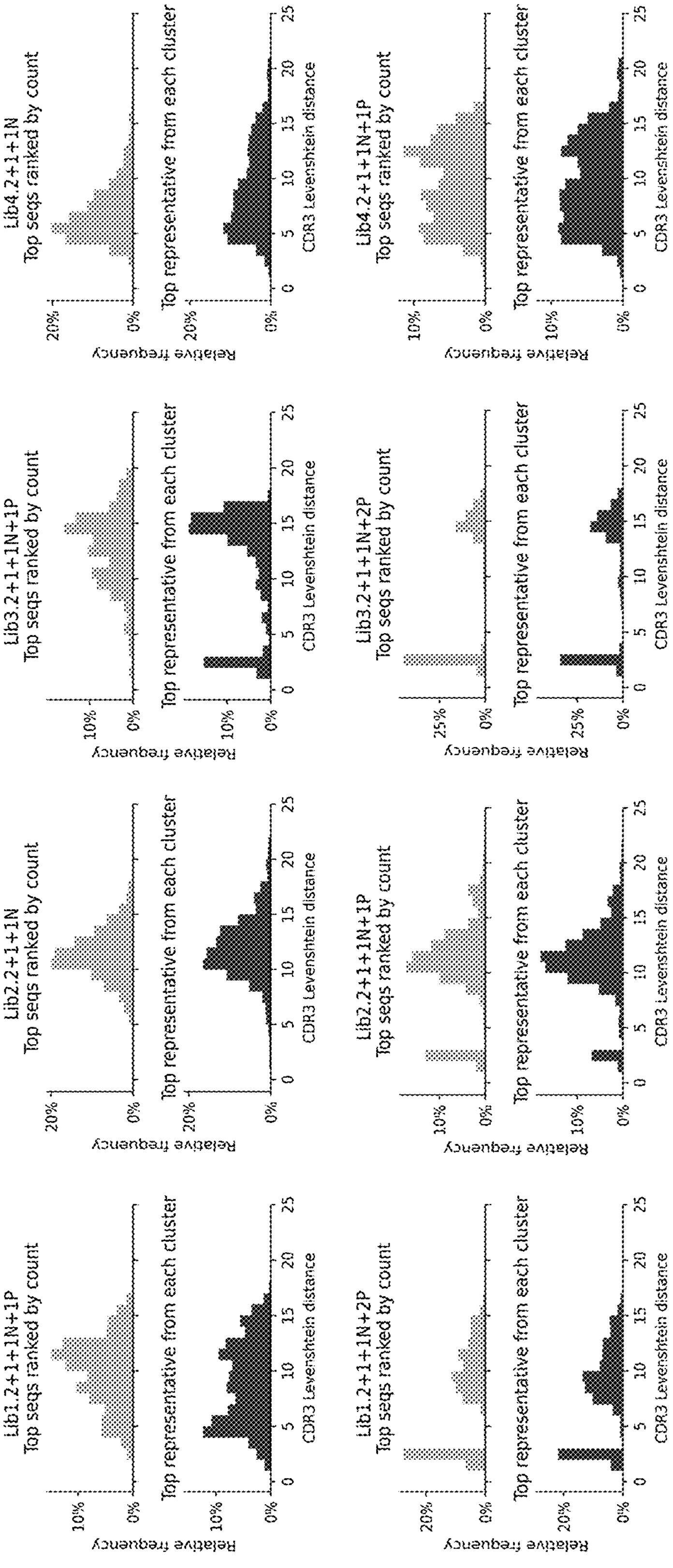
FIG. 20 shows the histogram disitribution of the Levenshtein distance between CDR3 sequences (up to 100) identified against B7-H4.
Figure 21:
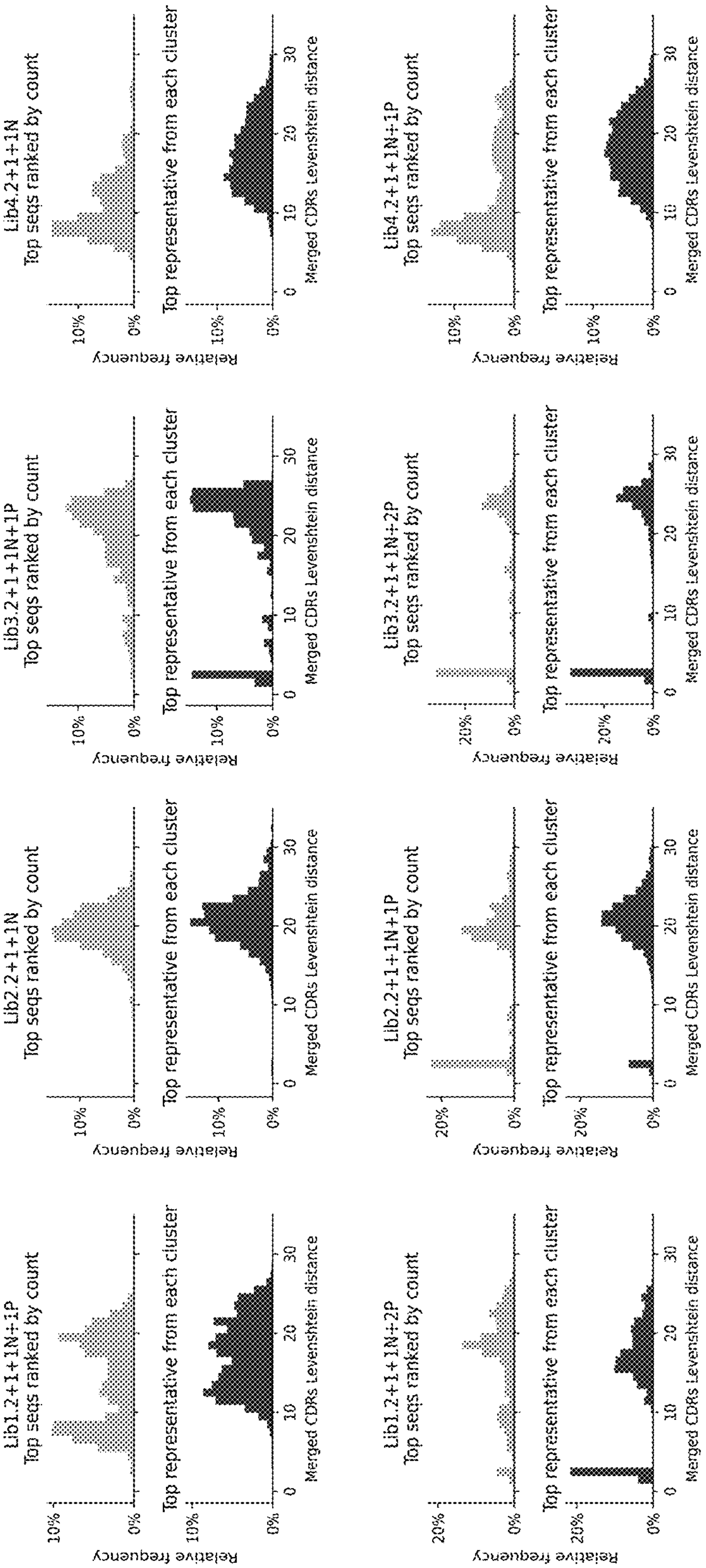
FIG. 21 shows the histogram disitribution of the combined Levenshtein distance between CDR1, CDR2, and CDR3 sequences (up to 100) identified against B7-H4.
Figure 22:
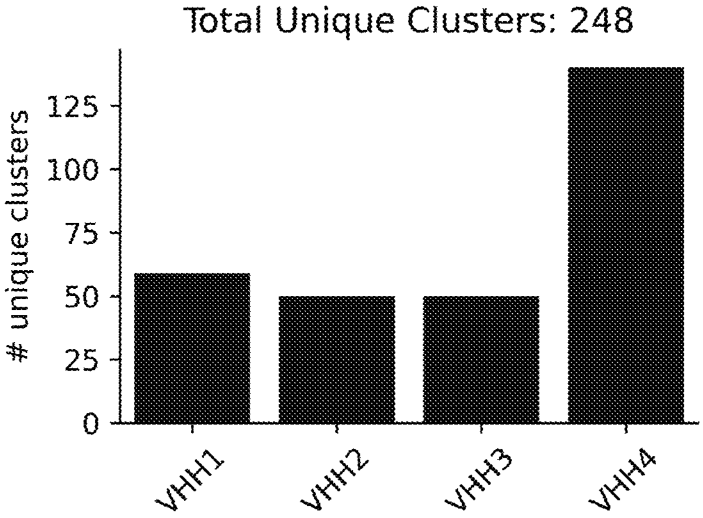
FIG. 22 shows the number of unique CDR3 cluster identified by next-generation sequencing against huma interferon alpha.
Figure 23:
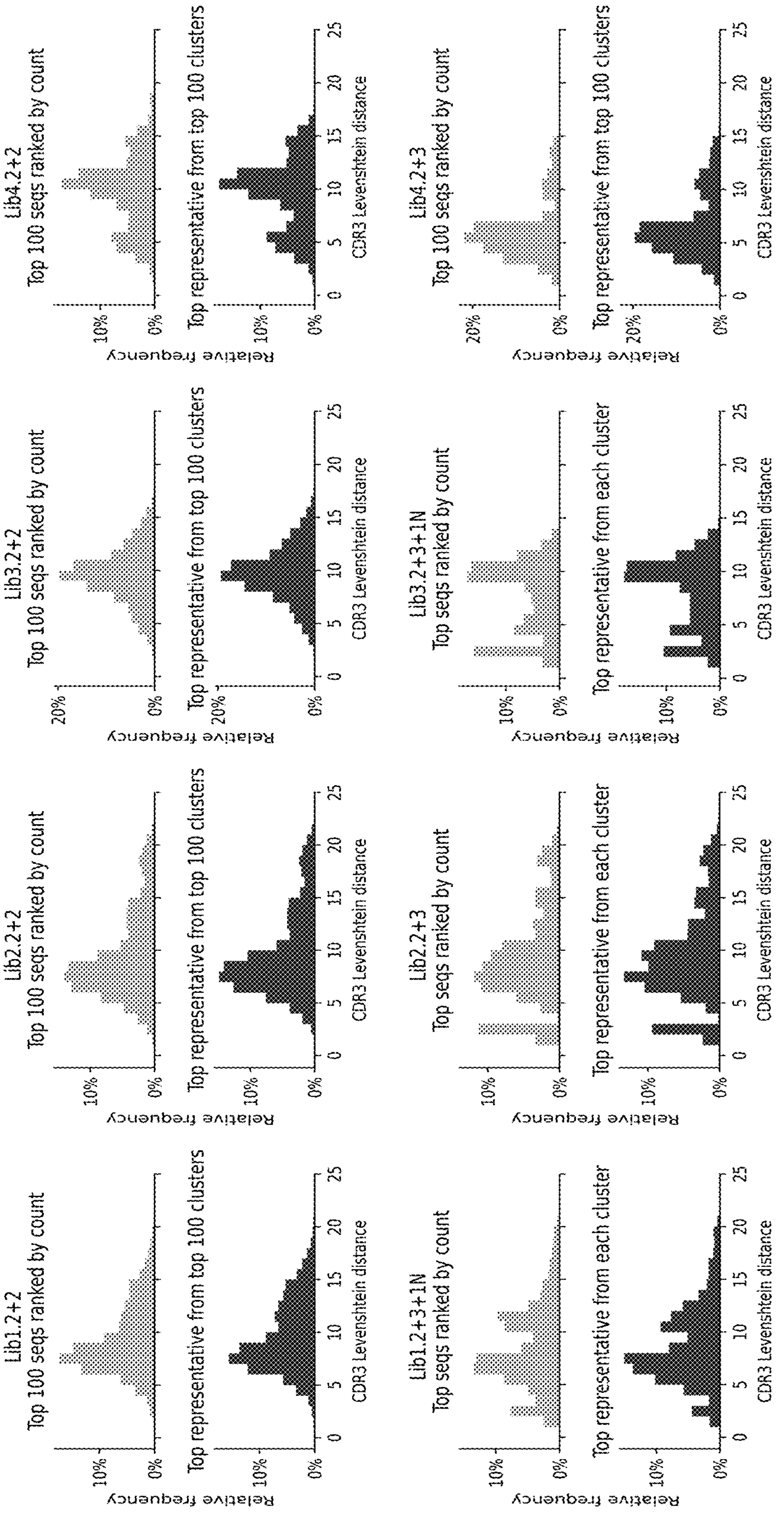
FIG. 23 shows the histogram disitribution of the Levenshtein distance between CDR3 sequences (up to 100) identified against interferon alpha.
Figure 24:
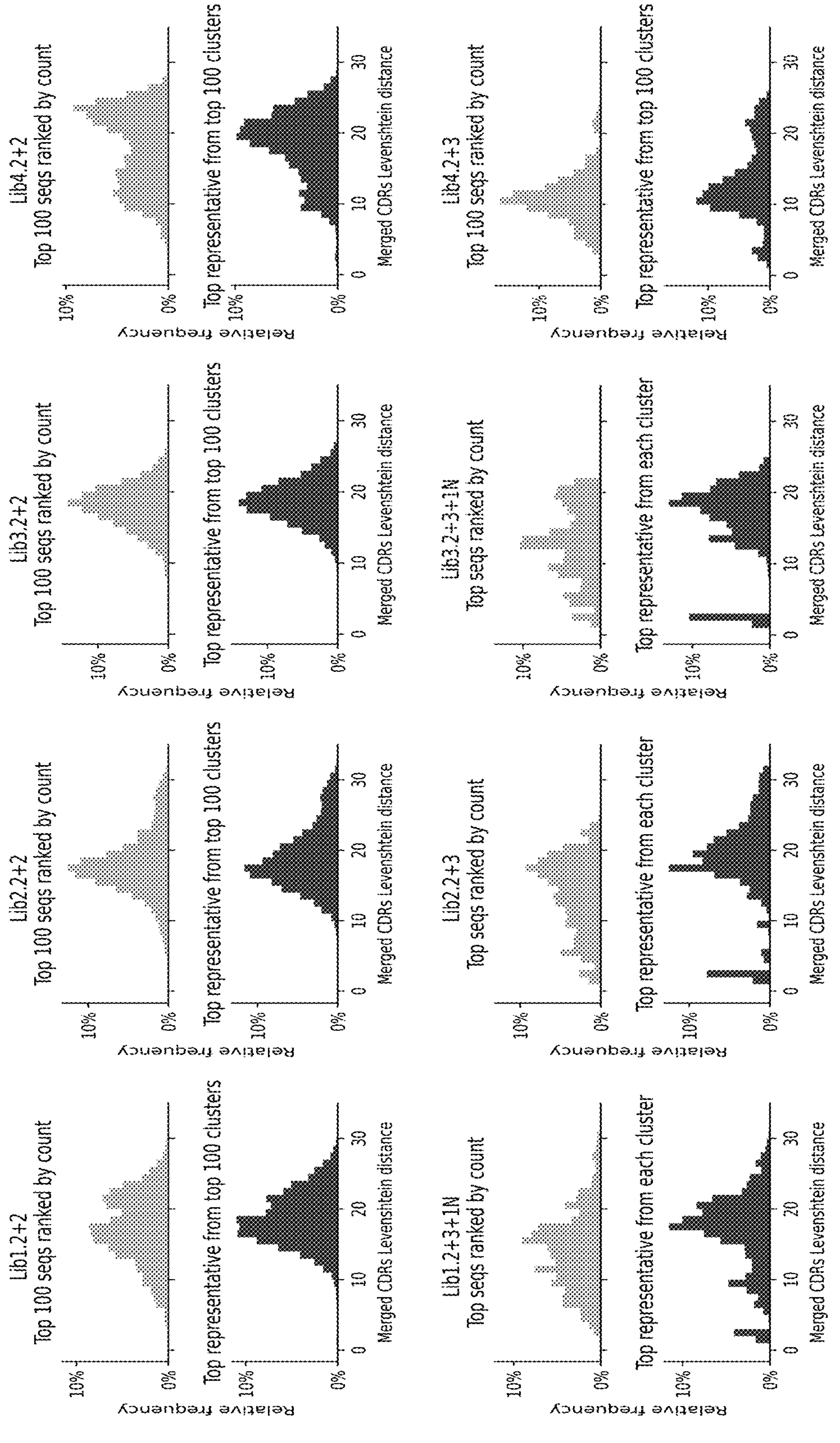
FIG. 24 shows the histogram disitribution of the combined Levenshtein distance between CDR1, CDR2, and CDR3 sequences (up to 100) identified against interferon alpha.
Figure 25:
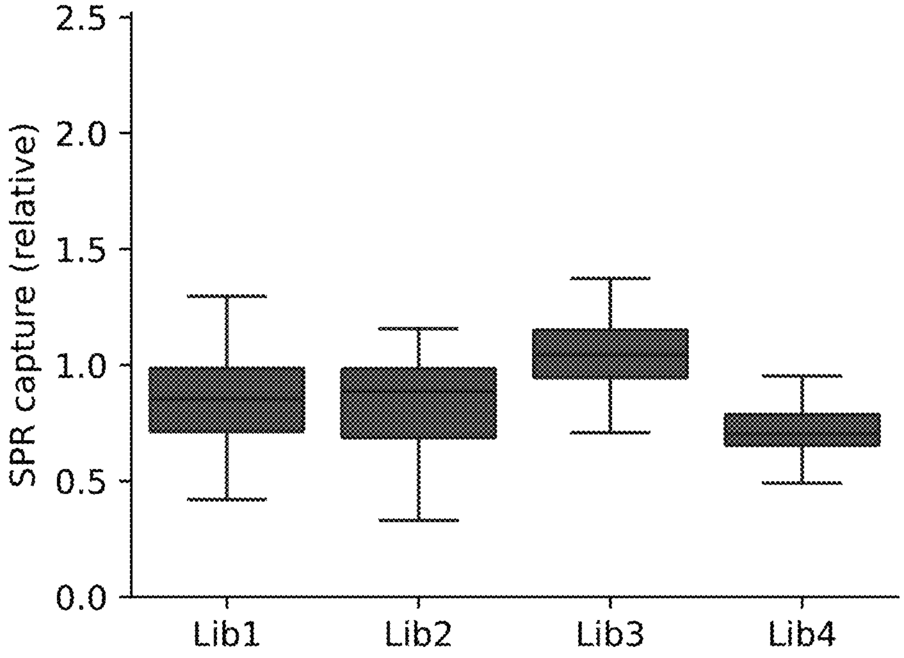
FIG. 25 shows expression levels assessed by protein A capture by surface plasmon resonance.

A total of 215 CDR3 clusters were identified for B7H4 (FIG. 19) among the four VHH libraries and 248 CDR3 clusters were identified for interferon-alpha (FIG. 22) for the four libraries. For each population, up to 100 unique CDR3 sequences were compared against each other using the Levenshtein distance, and alternatively, up to 100 of the top representative CDR3s of each cluster were selected for comparison using the Levenshtein distance—results for B7-H4 are shown in FIG. 20 and for interferon-alpha in FIG. 23. One can also compare all CDRs between the identified clones. Up to 100 unique clones were compared in all three CDRs using Levenshtein distance, and alternatively, up to 100 top representative clones of each cluster were selected for comparison using the Levenshtein distance—results for B7-H4 are shown in FIG. 21 and for interferon-alpha in FIG. 24. As can be seen in both figures the identified cluster representatives and top unique CDR3s are very different to one another.

TABLE 10

Selected populations submitted to next-generation sequencing.

| Antigen | Library | Rounds Of Phage Display | Positive Rounds of Yeast Display (P) | Negative Rounds of Yeast Display (N) | Notation |
|---|---|---|---|---|---|
| interferon-alpha | Lib1 | 2 | 2 | None | 2 + 2P |
| interferon-alpha | Lib2 | 2 | 2 | None | 2 + 2P |
| interferon-alpha | Lib3 | 2 | 2 | None | 2 + 2P |
| interferon-alpha | Lib4 | 2 | 2 | None | 2 + 2P |
| interferon-alpha | Lib1 | 2 | 3 | 1 | 2 + 3P + 1N |
| interferon-alpha | Lib2 | 2 | 3 | None | 2 + 3P |
| interferon-alpha | Lib3 | 2 | 3 | 1 | 2 + 3P + 1N |
| interferon-alpha | Lib4 | 2 | 3 | None | 2 + 3P |
| B7-H4 | Lib1 | 2 | 3 | 1 | 2 + 1P + 1N + 2P |
| B7-H4 | Lib2 | 2 | 1 | 1 | 2 + 1P + 1N |
| B7-H4 | Lib3 | 2 | 3 | 1 | 2 + 1P + 1N + 2P |
| B7-H4 | Lib4 | 2 | 1 | 1 | 2 + 1P + 1N |
| B7-H4 | Lib1 | 2 | 2 | 1 | 2 + 1P + 1N + 1P |
| B7-H4 | Lib2 | 2 | 2 | 1 | 2 + 1P + 1N + 1P |
| B7-H4 | Lib3 | 2 | 2 | 1 | 2 + 1P + 1N + 1P |
| B7-H4 | Lib4 | 2 | 2 | 1 | 2 + 1P + 1N + 1P |

Example 16: Antibody Maturation

To select an optimized VHH and assemble the CDRs into a mature antibody, the following approach can be used. First, two libraries are created: one where the CDR1 is replaced with the CDRs from the naïve library made using the corresponding framework scaffold and CDR2 and 3 are kept constant; another where CDR2 is replaced with the CDRs from the naïve library made using the corresponding framework scaffold and CDR1 and 3 are kept constant. The libraries are selected for high-affinity binding to the antigen. Next, the two selected libraries are combined and further selected for higher affinity to the target, yielding a mature antibody.

Example 17: Building a Library with a Modified Framework

Figure 26:
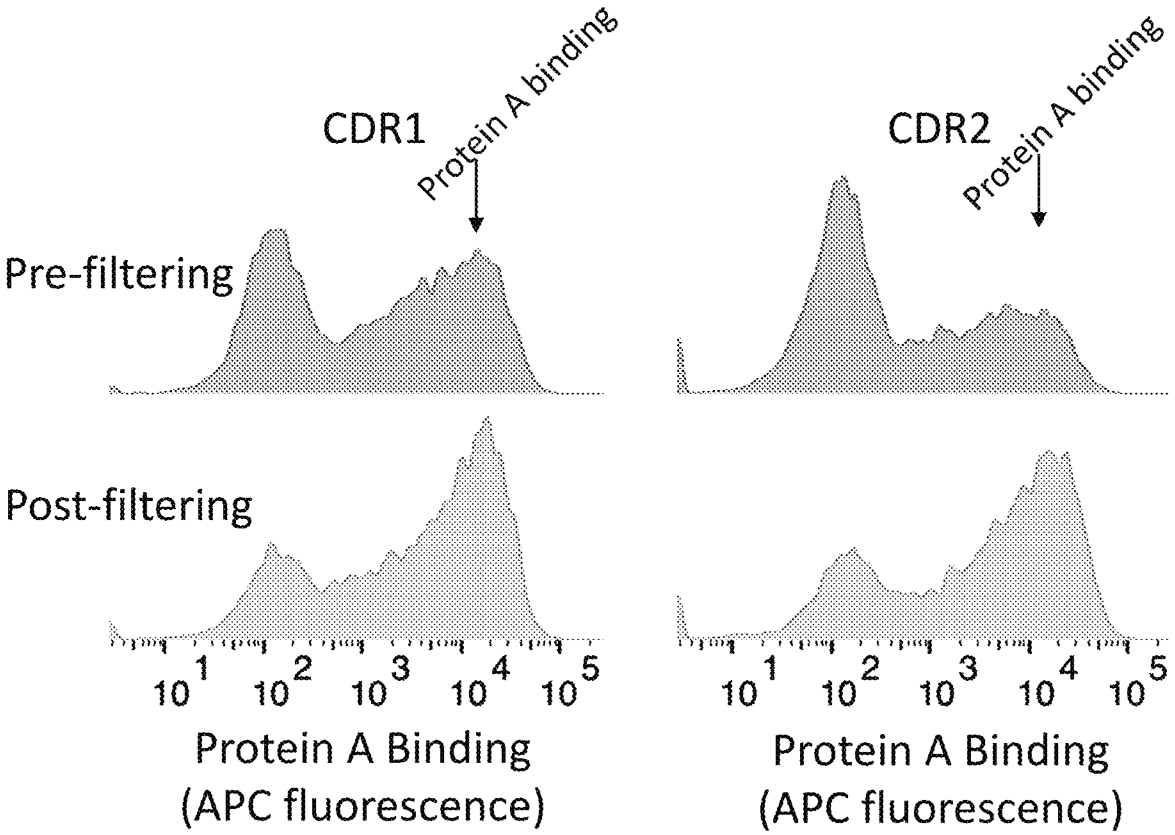
FIG. 26 shows flow cytometric analysis of Library 2A-CDR1 and Library 2A-CDR2 libraries, before and after sorting for protein A binding. This library was generated using the modified isecarosmab(1)(a) scaffold.

One can modify a chosen scaffold to achieve a desired goal, such as making it more similar to the natural germline. The isecarosmab(1) scaffold was mutated in two distinct positions: V11L and L89V (Kabat numbering), generating a new scaffold that is close to both the human germline (IGHV3-23) and alpaca germline (IGHV3-3). The yeast display CDR filtering for the protein A binding process was repeated for this scaffold (FIG. 26). The filtered CDRs were amplified, combined with the CDR3 amplified from donors, cloned into the pDAN5 phage display vector, and transformed into *E. coli* TG1 cells by electroporation, generating $4.8\times10^9$ transformants (Library 2A).

Figure 27:
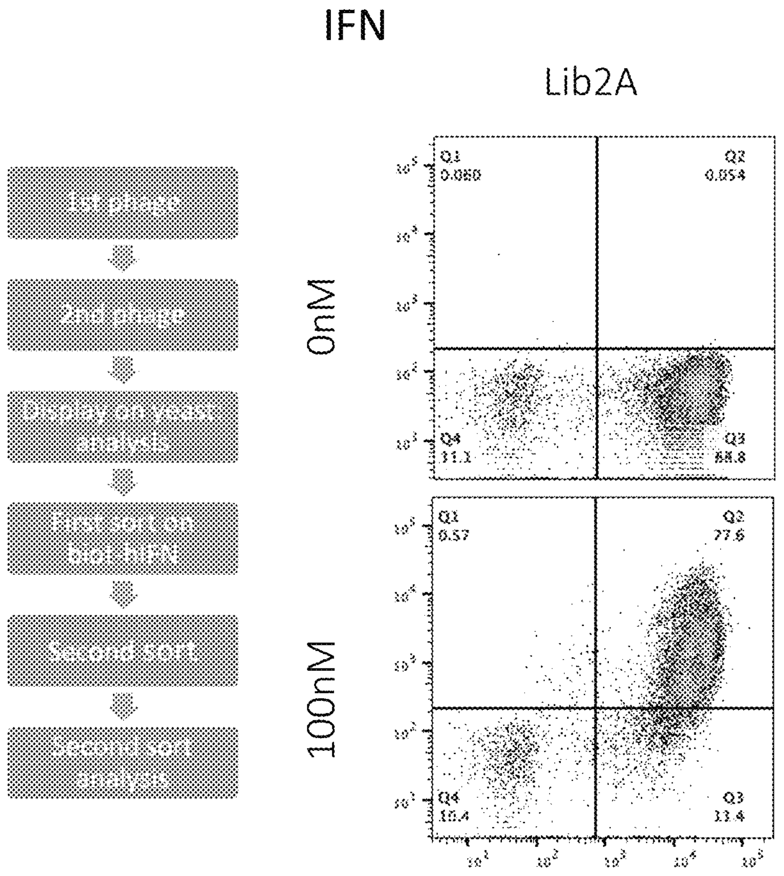
FIG. 27 shows flow cytometry data for Library 2A selected against human Interferon alpha.
Figure 28:
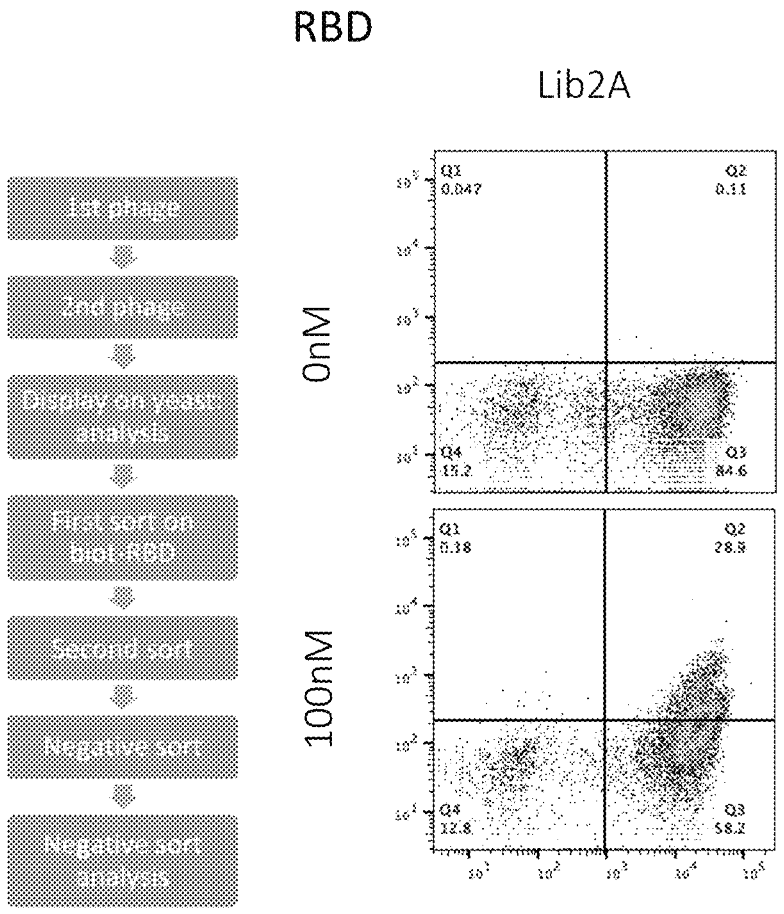
FIG. 28 shows flow cytometry data for Library 2A selected against receptor-binding domain of Sars-CoV-2.

Example 18: Generating Polyclonal Binding Populations from a Library with a Modified Framework The modified library was used for phage particle production and screened against a target of interest. While selection can be carried out using phage display alone it is preferable to combine phage and yeast display technologies. 1012 phage particles displaying the VHH libraries were used in two rounds of selection against the biotinylated recombinant interferon-alpha (IFN) and the receptor-binding domain from Sars-CoV-2 (RBD) using the Kingfisher magnetic bead system. $2\times10^7$ streptavidin-conjugated magnetic beads (Dynabeads M-280) coated with the biotinylated proteins (100-400 nM) were washed, coated with the antigen, incubated with the phage particles and washed again to remove non-binders. Phage particles were then eluted by reducing the pH and infecting F' pilus-carrying bacteria (Ominmax-2T1, Thermo Fisher Scientific)—output titers shown on Table 11. The phages were propagated, and the selection cycle was reiterated. After two rounds of phage enrichment, the VHH were PCR amplified and transferred to a C-terminal yeast display system by homologous recombination (pDNL6 yeast display vector), in which the VHH is displayed fused to the C terminus of Aga-2. The transformed yeast were then induced for VHH display by adding galactose to the culture media. The induced yeast mini-libraries were then used for another two rounds of enrichment against the biotinylated recombinant antigen by fluorescence-activated cell sorting. In the case of RBD, a third round using negative sorting was performed to remove streptavidin binders. The target concentration was kept at 100 nM in both positive enrichment rounds. After phage and yeast sorting enrichment, the recovered populations were analyzed by flow cytometry to test for binding against the antigens and in the absence of the antigen to check for non-specific binding to secondary reagents (IFN: FIG. 27; RBD: FIG. 28). Results show that the library successfully yielded binders to the antigen tested.

TABLE 11

Phage output titers after selection round using Library 2A.

| | $1^{st}$ round phage | $2^{nd}$ round phage |
|---|---|---|
| IFN | $4.6\times10^5$ CFU | $4.1\times10^8$ CFU |
| RBD | $2.2\times10^4$ CFU | $3.5\times10^8$ CFU |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for producing a VHH library, comprising:

(a) providing a first plurality of nucleic acids encoding amino acid sequences of one or more CDR1 fragments replicated from naturally occurring antibodies;

(b) providing a second plurality of nucleic acids encoding amino acid sequences of one or more CDR2 fragments replicated from naturally occurring antibodies;

(c) providing a third plurality of nucleic acids encoding amino acid sequences of one or more CDR3 fragments replicated from naturally occurring antibodies;

(d) providing a nucleic acid gene encoding amino acid sequences of a common VHH domain comprising a framework region 1, a CDR1 region, a framework region 2, a CDR2 region, a framework region 3, a CDR3 region, and a framework region 4; and (e) assembling the first plurality of nucleic acids, the second plurality of nucleic acids, and the third plurality of nucleic acids into the CDR1 region, the CDR2 region, and the CDR3 region, respectively, of the common VHH domain, thereby producing a population of nucleic acids encoding a VHH domain library;

the VHH domain library comprising:

a plurality of nucleic acids encoding a population of VHH domains comprising one or more CDR1s, one or more CDR2s, and one or more CDR3s located at the CDR1 region, the CDR2 region, and the CDR3 region of a VHH gene, respectively;

wherein the nucleic acid sequences encoding the amino acid sequences of the one or more CDR1s and the one or more CDR2s are from naturally occurring antibodies of a mammalian species;

wherein at least 90% of the one or more CDR1s and at least 90% of the one or more CDR2s are free of amino acid sequence liabilities, wherein the amino acid sequence liabilities are: (i) a glycosylation site comprising the motif NXS, NXT, or NXC, in which X represents any naturally occurring amino acid residue except for proline; (ii) a deamidation site comprising the motif of NG, NS, NT, NN, NA, NH, ND, NQ, NF, NW or NY; (iii) an isomerization site comprising the motif of DT, DH, DS, DG, DN, DR, DY or DD; (iv) any cysteines; (v) net charge greater than 1; (vi) a tripeptide motif containing at least two residues with aromatic side chains comprising F, H, W or Y; (vii) a polyspecificity site comprising the motif GG, GGG, RR, VG, W, WV, WW, WWW, YY, or WXW, in which X represents any amino acid residue; (viii) a protease sensitive or hydrolysis prone site comprising the motif of DX, in which X is P, G, S, V, Y, F, Q, K, L, or D; (ix) an integrin binding site comprising RGD, RYD, LDV, or KGD; (x) a lysine glycation site comprising KE, EK, or ED; (xi) a metal catalyzed fragmentation site comprising the motif of HS, SH, KT, HXS, or SXH, in which X represents any amino acid residue; (xii) a polyspecificity aggregation site comprising a motif of X.sub.1X.sub.2X.sub.3, wherein each of X.sub.1, X.sub.2, and X.sub.3 is independently selected from the group consisting of F, I, L, V, W and Y; (xiii) a streptavidin binding motif comprises the motif HPQ, EPDW (SEQ ID NO: 49), PWXWL (SEQ ID NO: 50), in which X represents any amino acid residue, GDWVFI (SEQ ID NO: 51), or PWPWLG (SEQ ID NO: 52); (xiv) one or more arginine residues; (xv) a hydrophobic CDR sequence; and/or (xvi) a CDR mutation that reduces binding to protein A said CDR mutation comprising any mutation in the last amino acid of the CDR2, according to the IMGT definition, to A, G, C, D, E, F, G, H, I, L, M, N, P, Q, S, V, W or Y;

wherein at least 95% of the one or more CDR1s, at least 95% of the one or more CDR2s, and at least 95% of the one or more CDR3s are free of non-functional members; wherein functional members are well folded and can form well folded VHHs;

wherein the framework regions 1, 2, 3, and 4 are from a partially humanized VH germline sequence or from a single therapeutic antibody VHH; wherein the therapeutic antibody VHH is selected from the group consisting of Caplacizumab, Envafolimab, Gontivimab, Isecarosmab, Ozoralizumab, Sonelokimab, and Vobarilizumab;

wherein each framework region can contain up to five amino acid substitutions, and wherein the nucleic acid sequences encoding the amino acid sequences of the one or more CDR3s are from heavy chain CDR3s of human donor lymphocytes.

2. The method of claim 1, wherein the first plurality of nucleic acids, the second plurality of nucleic acids, and the third plurality of nucleic acids is produced by a process comprising:

(a) obtaining amino acid sequences of the heavy chain CDR1 regions, heavy chain CDR2 regions and heavy chain CDR3 regions of a population of naturally occurring antibodies;

(b) excluding from (a) the heavy chain CDR1 amino acid sequences, the heavy chain CDR2 amino acid sequences, and the heavy chain CDR3 amino acid sequences amino acid sequences that comprise any or all of (i) to (xvi) to obtain sequence liability-free heavy chain CDR1 sequences, sequence liability-free heavy chain CDR2 sequences and sequence liability-free heavy chain CDR3 sequences; and (c) synthesizing the first plurality of nucleic acids that encode the sequence liability-free heavy chain CDR1 regions, the second plurality of nucleic acids that encode the sequence liability-free heavy chain CDR2 regions, and the third plurality of nucleic acids that encode the sequence liability-free heavy chain CDR3 regions.

3. The method of claim 1, wherein the human donor lymphocytes are B-cells.

4. The method of claim 1, wherein the processes for producing the first plurality of nucleic acids, the second plurality of nucleic acids, and the third plurality of nucleic acids further comprise isolating functional members from the liability-free heavy chain CDR1 and CDR2 regions, and from the CDR3 regions, wherein:

(i) the functional members of the sequence liability-free heavy chain CDR1 and CDR2 regions or the functional members of the CDR3 regions are isolated by expressing antibodies comprising the sequence liability-free heavy chain CDR1 and CDR2 regions, and the CDR3 regions in host cells in a manner that the antibodies are displayed on surface of the host cells, isolating the host cells that display antibodies on their surface, and using the CDR1, CDR2, and CDR3 regions in the displayed antibodies, which are functional members of the CDR1, CDR2, and/or CDR3 regions; or (ii) the functional members of the sequence liability-free heavy chain CDR1 and CDR2 regions, and the CDR3 regions are isolated by expressing antibodies comprising the sequence liability-free heavy chain CDR1 and CDR2 regions, and the CDR3 regions in fusion with a folding reporter, which optionally is β-lactamase or green fluorescent protein, or fragments thereof, to obtain members with improved folding.

5. The method of claim 1, wherein the mammalian species is human or camelid.

* * * * *

SEQUENCE LISTING

```
Sequence total quantity: 102
SEQ ID NO: 1           moltype = DNA  length = 401
FEATURE                Location/Qualifiers
source                 1..401
                       mol_type = other DNA
                       organism = synthetic construct
```

-continued

```
SEQUENCE: 1
gcgcgcatgc cgaggtgcag ctggtagagt ctgggggagg attggtgcag cctgggggct  60
ctctgagact ctcctgtgca gcctctggac gcaccttcag ttacaatccc atgggctggt  120
tccgccaggc tccagggaag ggcgtgagc  ttgtagcagc tattagcagg actggtggta  180
gcacatacta tccagactcc gtggagggcc gattcaccat ctccagagac aacgccaaga  240
gaatggtgta tctgcaaatg aacagcctga gagctgagga cacggccgtt tattactgtg  300
ctgctgctgg tgttcgtgct gaagatggtc gtgttcgtac cctgccatct gaatacacct  360
tctggggcca gggcacccag gtcactgtct cctcagctag c                      401

SEQ ID NO: 2           moltype = DNA  length = 389
FEATURE                Location/Qualifiers
source                 1..389
                       mol_type = other DNA
                       organism = synthetic construct
SEQUENCE: 2
gcgcgcatgc cgacgtgcag ctggtagagt ctgggggagg agtggtgcag cctgggggct  60
ctctgagact ctcctgtgca gcctctggac gcaccgtcag tagctatgcc atgggctggt  120
tccgccaggc tccagggaag gagcgtgagt ttgtggcggg tattagcagg agtgctgaaa  180
gaacatatta tgtagattcg ctgaagggcc gattcaccat ctccagagac aactccaaga  240
acacggtgta tctgcaaatg aacagcctaa gaccagagga cacggccctt tattactgtg  300
ctgctgatct ggatccaaac cgtatcttct ctcgtgaaga atacgcttac tggggccagg  360
gcaccctggt cactgtctcc tcagctagc                                   389

SEQ ID NO: 3           moltype = DNA  length = 383
FEATURE                Location/Qualifiers
source                 1..383
                       mol_type = other DNA
                       organism = synthetic construct
SEQUENCE: 3
gcgcgcatgc cgaggtgcag ctggtagagt ctgggggagg attggtgcag cctgggggct  60
ctctgagact ctcctgtgca gcctctggac gcacctacga tgccatgggc tggctccgcc  120
aggctccagg gaaggagcgt gagttcgttg ctgctattag cgggagtggt gatgacacat  180
attacgcaga ctcagtgaag ggccgattca ccatctccag agacaactcc aagaacacgc  240
tgtatctgca aatgaacagc ttaagaccag aggacacggc cgtttattac tgtgctaccc  300
gtcgtggtct gtactacgtt tgggatgcta acgattacga aaactggggc cagggcaccc  360
tggtcactgt ctcctcagct agc                                          383

SEQ ID NO: 4           moltype = DNA  length = 380
FEATURE                Location/Qualifiers
source                 1..380
                       mol_type = other DNA
                       organism = synthetic construct
SEQUENCE: 4
gcgcgcatgc cgaggtgcag ctggtagagt ctgggggagg attggtgcag cctgggggct  60
ctctgagact ctcctgtgca gcctctggaa gcgtcttcaa aatcaatgtc atggcctggt  120
accgccaggc tccagggaag ggcgtgagc  tggtcgccgg cattataagt ggtggtagca  180
catcctatgc ggattctgtg aagggccgat tcaccatctc cagagacaac gccaagaaca  240
cgctgtatct gcaaatgaac agcctaagac ccgaggacac ggccgtttat tactgtgctt  300
tcatcaccac cgaatctgat tacgatctgg gtcgtcgtta ctggggccag ggcaccctgg  360
tcactgtctc ctcagctagc                                              380

SEQ ID NO: 5           moltype = DNA  length = 406
FEATURE                Location/Qualifiers
source                 1..406
                       mol_type = other DNA
                       organism = synthetic construct
SEQUENCE: 5
gcgcgcatgc cgaggtgcag ctggtagagt ctgggggagg attggtgcag cctgggggct  60
ctctgagact ctcctgtgca gcctctagag accatggcca gtaaggccgg tctctatggg  120
ctggttccgc caggctccag ggaaggggcg tgagcttgta gcagctatca gttggagcgg  180
aggtagtaca tactatccag actccgtgga gggccgattc accatctcca gagacaacgc  240
caagagaatg gtgtatctgc aaatgaacag cctgagagct gaggacacgg ccgtttatta  300
ctgtgctgct gctggtgttc gtgctgaaga tggtcgtgtt cgtaccctgc catctgaata  360
caccttctgg ggccagggca cccaggtcac tgtctcctca gctagc                 406

SEQ ID NO: 6           moltype = DNA  length = 406
FEATURE                Location/Qualifiers
source                 1..406
                       mol_type = other DNA
                       organism = synthetic construct
SEQUENCE: 6
gcgcgcatgc cgaggtgcag ctggtagagt ctgggggagg attggtgcag cctgggggct  60
ctctgagact ctcctgtgca gcctctggat tcacctttag cagctatgcc atgggctggt  120
tccgccaggc tccagggaag ggcgtgagc  ttgtagcagc tagagaccat ggccagtaag  180
gccggtctct tactatccag actccgtgga gggccgattc accatctcca gagacaacgc  240
caagagaatg gtgtatctgc aaatgaacag cctgagagct gaggacacgg ccgtttatta  300
ctgtgctgct gctggtgttc gtgctgaaga tggtcgtgtt cgtaccctgc catctgaata  360
caccttctgg ggccagggca cccaggtcac tgtctcctca gctagc                 406
```

-continued

```
SEQ ID NO: 7           moltype = DNA  length = 394
FEATURE                Location/Qualifiers
source                 1..394
                       mol_type = other DNA
                       organism = synthetic construct
SEQUENCE: 7
gcgcgcatgc cgacgtgcag ctggtagagt ctgggggagg agtggtgcag cctgggggct  60
ctctgagact ctcctgtgca gcctctagag accatggcca gtaaggccgg tctctatggg  120
ctggttccgc caggctccag ggaaggagcg tgagtttgtg gcgggtatca gttggagcgg  180
aggtagtaca tattatgtag attcgctgaa gggccgattc accatctcca gagacaactc  240
caagaacacg gtgtatctgc aaatgaacag cctaagacca gaggacacgg ccctttatta  300
ctgtgctgct gatctggatc caaaccgtat cttctctcgt gaagaatacg cttactgggg  360
ccagggcacc ctggtcactg tctcctcagc tagc                             394

SEQ ID NO: 8           moltype = DNA  length = 394
FEATURE                Location/Qualifiers
source                 1..394
                       mol_type = other DNA
                       organism = synthetic construct
SEQUENCE: 8
gcgcgcatgc cgacgtgcag ctggtagagt ctgggggagg agtggtgcag cctgggggct  60
ctctgagact ctcctgtgca gcctctggat tcacctttag cagctatgcc atgggctggt  120
tccgccaggc tccagggaag gagcgtgagt ttgtggcggg tagagaccat ggccagtaag  180
gccggtctct tattatgtag attcgctgaa gggccgattc accatctcca gagacaactc  240
caagaacacg gtgtatctgc aaatgaacag cctaagacca gaggacacgg ccctttatta  300
ctgtgctgct gatctggatc caaaccgtat cttctctcgt gaagaatacg cttactgggg  360
ccagggcacc ctggtcactg tctcctcagc tagc                             394

SEQ ID NO: 9           moltype = DNA  length = 394
FEATURE                Location/Qualifiers
source                 1..394
                       mol_type = other DNA
                       organism = synthetic construct
SEQUENCE: 9
gcgcgcatgc cgaggtgcag ctggtagagt ctgggggagg attggtgcag cctgggggct  60
ctctgagact ctcctgtgca gcctctagag accatggcca gtaaggccgg tctctatggg  120
ctggctccgc caggctccag ggaaggagcg tgagttcgtt gctgctatca gttggagcgg  180
aggtagtaca tattacgcag actcagtgaa gggccgattc accatctcca gagacaactc  240
caagaacacg ctgtatctgc aaatgaacag cttaagacca gaggacacgg ccgtttatta  300
ctgtgctacc cgtcgtggtc tgtactacgt ttgggatgct aacgattacg aaaactgggg  360
ccagggcacc ctggtcactg tctcctcagc tagc                             394

SEQ ID NO: 10          moltype = DNA  length = 394
FEATURE                Location/Qualifiers
source                 1..394
                       mol_type = other DNA
                       organism = synthetic construct
SEQUENCE: 10
gcgcgcatgc cgaggtgcag ctggtagagt ctgggggagg attggtgcag cctgggggct  60
ctctgagact ctcctgtgca gcctctggat tcacctttag cagctatgcc atgggctggc  120
tccgccaggc tccagggaag gagcgtgagt tcgttgctgc tagagaccat ggccagtaag  180
gccggtctct tattacgcag actcagtgaa gggccgattc accatctcca gagacaactc  240
caagaacacg ctgtatctgc aaatgaacag cttaagacca gaggacacgg ccgtttatta  300
ctgtgctacc cgtcgtggtc tgtactacgt ttgggatgct aacgattacg aaaactgggg  360
ccagggcacc ctggtcactg tctcctcagc tagc                             394

SEQ ID NO: 11          moltype = DNA  length = 388
FEATURE                Location/Qualifiers
source                 1..388
                       mol_type = other DNA
                       organism = synthetic construct
SEQUENCE: 11
gcgcgcatgc cgaggtgcag ctggtagagt ctgggggagg attggtgcag cctgggggct  60
ctctgagact ctcctgtgca gcctctagag accatggcca gtaaggccgg tctctatggc  120
ctggtaccgc caggctccag ggaaggggcg tgagctggtc gccggcatca gttggagcgg  180
aggtagtaca tcctatgcgg attctgtgaa gggccgattc accatctcca gagacaacgc  240
caagaacacg ctgtatctgc aaatgaacag cctaagaccc gaggacacgg ccgtttatta  300
ctgtgctttc atcaccaccg aatctgatta cgatctgggt cgtcgttact ggggccaggg  360
caccctggtc actgtctcct cagctagc                                    388

SEQ ID NO: 12          moltype = DNA  length = 388
FEATURE                Location/Qualifiers
source                 1..388
                       mol_type = other DNA
                       organism = synthetic construct
SEQUENCE: 12
gcgcgcatgc cgaggtgcag ctggtagagt ctgggggagg attggtgcag cctgggggct  60
ctctgagact ctcctgtgca gcctctggat tcacctttag cagctatgcc atggcctggt  120
accgccaggc tccagggaag gggcgtgagc tggtcgccgg cagagaccat ggccagtaag  180
```

```
gccggtctct tcctatgcgg attctgtgaa gggccgattc accatctcca gagacaacgc  240
caagaacacg ctgtatctgc aaatgaacag cctaagaccc gaggacacgg ccgtttatta  300
ctgtgctttc atcaccaccg aatctgatta cgatctgggt cgtcgttact ggggccaggg  360
caccctggtc actgtctcct cagctagc                                      388

SEQ ID NO: 13          moltype = DNA  length = 42
FEATURE                Location/Qualifiers
source                 1..42
                       mol_type = other DNA
                       organism = synthetic construct
SEQUENCE: 13
gtgcagcctg ggggctctct gagactctcc tgtgcagcct ct                     42

SEQ ID NO: 14          moltype = DNA  length = 42
FEATURE                Location/Qualifiers
source                 1..42
                       mol_type = other DNA
                       organism = synthetic construct
SEQUENCE: 14
aagctcacgc cccttccctg gagcctggcg gaaccagccc at                     42

SEQ ID NO: 15          moltype = DNA  length = 42
FEATURE                Location/Qualifiers
source                 1..42
                       mol_type = other DNA
                       organism = synthetic construct
SEQUENCE: 15
ttccgccagg ctccagggaa ggggcgtgag cttgtagcag ct                     42

SEQ ID NO: 16          moltype = DNA  length = 42
FEATURE                Location/Qualifiers
source                 1..42
                       mol_type = other DNA
                       organism = synthetic construct
SEQUENCE: 16
tctggagatg gtgaatcggc cctccacgga gtctggatag ta                     42

SEQ ID NO: 17          moltype = DNA  length = 42
FEATURE                Location/Qualifiers
source                 1..42
                       mol_type = other DNA
                       organism = synthetic construct
SEQUENCE: 17
gtgcagcctg ggggctctct gagactctcc tgtgcagcct ct                     42

SEQ ID NO: 18          moltype = DNA  length = 42
FEATURE                Location/Qualifiers
source                 1..42
                       mol_type = other DNA
                       organism = synthetic construct
SEQUENCE: 18
aaactcacgc tccttccctg gagcctggcg gaaccagccc at                     42

SEQ ID NO: 19          moltype = DNA  length = 42
FEATURE                Location/Qualifiers
source                 1..42
                       mol_type = other DNA
                       organism = synthetic construct
SEQUENCE: 19
ttccgccagg ctccagggaa ggagcgtgag tttgtggcgg gt                     42

SEQ ID NO: 20          moltype = DNA  length = 42
FEATURE                Location/Qualifiers
source                 1..42
                       mol_type = other DNA
                       organism = synthetic construct
SEQUENCE: 20
tctggagatg gtgaatcggc ccttcagcga atctacataa ta                     42

SEQ ID NO: 21          moltype = DNA  length = 42
FEATURE                Location/Qualifiers
source                 1..42
                       mol_type = other DNA
                       organism = synthetic construct
SEQUENCE: 21
gtgcagcctg ggggctctct gagactctcc tgtgcagcct ct                     42

SEQ ID NO: 22          moltype = DNA  length = 42
FEATURE                Location/Qualifiers
```

```
                        source                 1..42
                                               mol_type = other DNA
                                               organism = synthetic construct
SEQUENCE: 22
gaactcacgc tccttccctg gagcctggcg gagccagccc at                              42

SEQ ID NO: 23           moltype = DNA   length = 42
FEATURE                 Location/Qualifiers
source                  1..42
                        mol_type = other DNA
                        organism = synthetic construct
SEQUENCE: 23
ctccgccagg ctccagggaa ggagcgtgag ttcgttgctg ct                              42

SEQ ID NO: 24           moltype = DNA   length = 42
FEATURE                 Location/Qualifiers
source                  1..42
                        mol_type = other DNA
                        organism = synthetic construct
SEQUENCE: 24
tctggagatg gtgaatcggc ccttcactga gtctgcgtaa ta                              42

SEQ ID NO: 25           moltype = DNA   length = 42
FEATURE                 Location/Qualifiers
source                  1..42
                        mol_type = other DNA
                        organism = synthetic construct
SEQUENCE: 25
gtgcagcctg ggggctctct gagactctcc tgtgcagcct ct                              42

SEQ ID NO: 26           moltype = DNA   length = 42
FEATURE                 Location/Qualifiers
source                  1..42
                        mol_type = other DNA
                        organism = synthetic construct
SEQUENCE: 26
cagctcacgc cccttccctg gagcctggcg gtaccaggcc at                              42

SEQ ID NO: 27           moltype = DNA   length = 42
FEATURE                 Location/Qualifiers
source                  1..42
                        mol_type = other DNA
                        organism = synthetic construct
SEQUENCE: 27
taccgccagg ctccagggaa ggggcgtgag ctggtcgccg gc                              42

SEQ ID NO: 28           moltype = DNA   length = 42
FEATURE                 Location/Qualifiers
source                  1..42
                        mol_type = other DNA
                        organism = synthetic construct
SEQUENCE: 28
tctggagatg gtgaatcggc ccttcacaga atccgcatag ga                              42

SEQ ID NO: 29           moltype = DNA   length = 42
FEATURE                 Location/Qualifiers
source                  1..42
                        mol_type = other DNA
                        organism = synthetic construct
SEQUENCE: 29
ctgtcttctc tgaaatctga ggacacggcc gtgtattact gt                              42

SEQ ID NO: 30           moltype = DNA   length = 42
FEATURE                 Location/Qualifiers
source                  1..42
                        mol_type = other DNA
                        organism = synthetic construct
SEQUENCE: 30
atgaactctc tgcgtgccga ggacacggct gtgtattact gt                              42

SEQ ID NO: 31           moltype = DNA   length = 42
FEATURE                 Location/Qualifiers
source                  1..42
                        mol_type = other DNA
                        organism = synthetic construct
SEQUENCE: 31
gttaactctg ttaccgccgc ggacacggct gtgtattact gt                              42
```

```
SEQ ID NO: 32          moltype = DNA  length = 43
FEATURE                Location/Qualifiers
source                 1..43
                       mol_type = other DNA
                       organism = synthetic construct
SEQUENCE: 32
gaaaagggtt ggggcggatg cgctagctga ggagacggtg acc                    43

SEQ ID NO: 33          moltype = DNA  length = 20
FEATURE                Location/Qualifiers
source                 1..20
                       mol_type = other DNA
                       organism = synthetic construct
SEQUENCE: 33
agctgctaca agctcacgcc                                              20

SEQ ID NO: 34          moltype = DNA  length = 20
FEATURE                Location/Qualifiers
source                 1..20
                       mol_type = other DNA
                       organism = synthetic construct
SEQUENCE: 34
atgggctggt tccgccaggc                                              20

SEQ ID NO: 35          moltype = DNA  length = 22
FEATURE                Location/Qualifiers
source                 1..22
                       mol_type = other DNA
                       organism = synthetic construct
SEQUENCE: 35
acagtaataa acggccgtgt cc                                           22

SEQ ID NO: 36          moltype = DNA  length = 27
FEATURE                Location/Qualifiers
source                 1..27
                       mol_type = other DNA
                       organism = synthetic construct
SEQUENCE: 36
gctgaggaca cggccgttta ttactgt                                      27

SEQ ID NO: 37          moltype = DNA  length = 20
FEATURE                Location/Qualifiers
source                 1..20
                       mol_type = other DNA
                       organism = synthetic construct
SEQUENCE: 37
acccgccaca aactcacgct                                              20

SEQ ID NO: 38          moltype = DNA  length = 20
FEATURE                Location/Qualifiers
source                 1..20
                       mol_type = other DNA
                       organism = synthetic construct
SEQUENCE: 38
atgggctggt tccgccaggc                                              20

SEQ ID NO: 39          moltype = DNA  length = 22
FEATURE                Location/Qualifiers
source                 1..22
                       mol_type = other DNA
                       organism = synthetic construct
SEQUENCE: 39
acagtaataa agggccgtgt cc                                           22

SEQ ID NO: 40          moltype = DNA  length = 27
FEATURE                Location/Qualifiers
source                 1..27
                       mol_type = other DNA
                       organism = synthetic construct
SEQUENCE: 40
ccagaggaca cggcccttta ttactgt                                      27

SEQ ID NO: 41          moltype = DNA  length = 20
FEATURE                Location/Qualifiers
source                 1..20
                       mol_type = other DNA
                       organism = synthetic construct
```

```
SEQUENCE: 41
agcagcaacg aactcacgct                                              20

SEQ ID NO: 42          moltype = DNA  length = 20
FEATURE                Location/Qualifiers
source                 1..20
                       mol_type = other DNA
                       organism = synthetic construct
SEQUENCE: 42
atgggctggc tccgccaggc                                              20

SEQ ID NO: 43          moltype = DNA  length = 22
FEATURE                Location/Qualifiers
source                 1..22
                       mol_type = other DNA
                       organism = synthetic construct
SEQUENCE: 43
acagtaataa acggccgtgt cc                                           22

SEQ ID NO: 44          moltype = DNA  length = 27
FEATURE                Location/Qualifiers
source                 1..27
                       mol_type = other DNA
                       organism = synthetic construct
SEQUENCE: 44
ccagaggaca cggccgttta ttactgt                                      27

SEQ ID NO: 45          moltype = DNA  length = 20
FEATURE                Location/Qualifiers
source                 1..20
                       mol_type = other DNA
                       organism = synthetic construct
SEQUENCE: 45
gccggcgacc agctcacgcc                                              20

SEQ ID NO: 46          moltype = DNA  length = 20
FEATURE                Location/Qualifiers
source                 1..20
                       mol_type = other DNA
                       organism = synthetic construct
SEQUENCE: 46
atggcctggt accgccaggc                                              20

SEQ ID NO: 47          moltype = DNA  length = 22
FEATURE                Location/Qualifiers
source                 1..22
                       mol_type = other DNA
                       organism = synthetic construct
SEQUENCE: 47
acagtaataa acggccgtgt cc                                           22

SEQ ID NO: 48          moltype = DNA  length = 27
FEATURE                Location/Qualifiers
source                 1..27
                       mol_type = other DNA
                       organism = synthetic construct
SEQUENCE: 48
cccgaggaca cggccgttta ttactgt                                      27

SEQ ID NO: 49          moltype = AA  length = 4
FEATURE                Location/Qualifiers
source                 1..4
                       mol_type = protein
                       organism = synthetic construct
SEQUENCE: 49
EPDW                                                               4

SEQ ID NO: 50          moltype = AA  length = 5
FEATURE                Location/Qualifiers
source                 1..5
                       mol_type = protein
                       organism = synthetic construct
SEQUENCE: 50
PWXWL                                                              5

SEQ ID NO: 51          moltype = AA  length = 6
FEATURE                Location/Qualifiers
```

-continued

```
source                  1..6
                        mol_type = protein
                        organism = synthetic construct
SEQUENCE: 51
GDWVFI                                                          6

SEQ ID NO: 52           moltype = AA  length = 6
FEATURE                 Location/Qualifiers
source                  1..6
                        mol_type = protein
                        organism = synthetic construct
SEQUENCE: 52
PWPWLG                                                          6

SEQ ID NO: 53           moltype = AA  length = 128
FEATURE                 Location/Qualifiers
source                  1..128
                        mol_type = protein
                        organism = synthetic construct
SEQUENCE: 53
EVQLVESGGG LVQPGGSLRL SCAASGRTFS YNPMGWFRQA PGKGRELVAA ISRTGGSTYY  60
PDSVEGRFTI SRDNAKRMVY LQMNSLRAED TAVYYCAAAG VRAEDGRVRT LPSEYTFWGQ  120
GTQVTVSS                                                           128

SEQ ID NO: 54           moltype = AA  length = 124
FEATURE                 Location/Qualifiers
source                  1..124
                        mol_type = protein
                        organism = synthetic construct
SEQUENCE: 54
DVQLVESGGG VVQPGGSLRL SCAASGRTVS SYAMGWFRQA PGKEREFVAG ISRSAERTYY  60
VDSLKGRFTI SRDNSKNTVY LQMNSLRPED TALYYCAADL DPNRIFSREE YAYWGQGTLV  120
TVSS                                                               124

SEQ ID NO: 55           moltype = AA  length = 122
FEATURE                 Location/Qualifiers
source                  1..122
                        mol_type = protein
                        organism = synthetic construct
SEQUENCE: 55
EVQLVESGGG LVQPGGSLRL SCAASGRTYD AMGWLRQAPG KEREFVAAIS GSGDDTYYAD  60
SVKGRFTISR DNSKNTLYLQ MNSLRPEDTA VYYCATRRGL YYVWDANDYE NWGQGTLVTV  120
SS                                                                 122

SEQ ID NO: 56           moltype = AA  length = 121
FEATURE                 Location/Qualifiers
source                  1..121
                        mol_type = protein
                        organism = synthetic construct
SEQUENCE: 56
EVQLVESGGG LVQPGGSLRL SCAASGSVFK INVMAWYRQA PGKGRELVAG IISGGSTSYA  60
DSVKGRFTIS RDNAKNTLYL QMNSLRPEDT AVYYCAFITT ESDYDLGRRY WGQGTLVTVS  120
S                                                                  121

SEQ ID NO: 57           moltype = DNA  length = 389
FEATURE                 Location/Qualifiers
source                  1..389
                        mol_type = other DNA
                        organism = synthetic construct
SEQUENCE: 57
gcgcgcatgc cgacgtgcag ctggtagagt ctgggggagg attggtgcag cctgggggct  60
ctctgagact ctcctgtgca gcctctggac gcaccgtcag tagctatgcc atgggctggt  120
tccgccaggc tccagggaag gagcgtgagt ttgtggcggg tattagcagg agtgctgaaa  180
gaacatatta tgtagattcg ctgaagggcc gattcaccat ctccagagac aactccaaga  240
acacggtgta tctgcaaatg aacagcctaa gaccagagga cacggccgtt tattactgtg  300
ctgctgatct ggatccaaac cgtatcttct ctcgtgaaga atacgcttac tggggccagg  360
gcaccctggt cactgtctcc tcagctagc                                   389

SEQ ID NO: 58           moltype = AA  length = 124
FEATURE                 Location/Qualifiers
source                  1..124
                        mol_type = protein
                        organism = synthetic construct
SEQUENCE: 58
DVQLVESGGG LVQPGGSLRL SCAASGRTVS SYAMGWFRQA PGKEREFVAG ISRSAERTYY  60
VDSLKGRFTI SRDNSKNTVY LQMNSLRPED TAVYYCAADL DPNRIFSREE YAYWGQGTLV  120
TVSS                                                               124

SEQ ID NO: 59           moltype = DNA  length = 394
```

-continued

```
FEATURE                 Location/Qualifiers
source                  1..394
                        mol_type = other DNA
                        organism = synthetic construct
SEQUENCE: 59
gcgcgcatgc cgacgtgcag ctggtagagt ctgggggagg attggtgcag cctgggggct  60
ctctgagact ctcctgtgca gcctctagag accatggcca gtaaggccgg tctctatggg  120
ctggttccgc caggctccag ggaaggagcg tgagtttgtg gcgggtatca gttggagcgg  180
aggtagtaca tattatgtag attcgctgaa gggccgattc accatctcca gagacaactc  240
caagaacacg gtgtatctgc aaatgaacag cctaagacca gaggacacgg ccgtttatta  300
ctgtgctgct gatctggatc caaaccgtat cttctctcgt gaagaatacg cttactgggg  360
ccagggcacc ctggtcactg tctcctcagc tagc                             394

SEQ ID NO: 60           moltype = DNA  length = 394
FEATURE                 Location/Qualifiers
source                  1..394
                        mol_type = other DNA
                        organism = synthetic construct
SEQUENCE: 60
gcgcgcatgc cgacgtgcag ctggtagagt ctgggggagg attggtgcag cctgggggct  60
ctctgagact ctcctgtgca gcctctggat tcacctttag cagctatgcc atgggctggt  120
tccgccaggc tccagggaag gagcgtgagt ttgtggcggg tagagaccat ggccagtaag  180
gccggtctct tattatgtag attcgctgaa gggccgattc accatctcca gagacaactc  240
caagaacacg gtgtatctgc aaatgaacag cctaagacca gaggacacgg ccgtttatta  300
ctgtgctgct gatctggatc caaaccgtat cttctctcgt gaagaatacg cttactgggg  360
ccagggcacc ctggtcactg tctcctcagc tagc                             394

SEQ ID NO: 61           moltype = AA  length = 96
FEATURE                 Location/Qualifiers
source                  1..96
                        mol_type = protein
                        organism = synthetic construct
SEQUENCE: 61
EVQLVESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYC                           96

SEQ ID NO: 62           moltype = AA  length = 96
FEATURE                 Location/Qualifiers
source                  1..96
                        mol_type = protein
                        organism = synthetic construct
SEQUENCE: 62
EVQLVESGGG LVQPGGSLRL SCAASGRTFS YNPMGWFRQA PGKGRELVAA ISRTGGSTYY  60
PDSVEGRFTI SRDNAKRMVY LQMNSLRAED TAVYYC                           96

SEQ ID NO: 63           moltype = AA  length = 96
FEATURE                 Location/Qualifiers
source                  1..96
                        mol_type = protein
                        organism = synthetic construct
SEQUENCE: 63
QVQLVESGGG LVQPGGSLRL SCAASGKMSS RRCMAWFRQA PGKERERVAK LLTTSGSTYL  60
ADSVKGRFTI SRDNSKNTVY LQMNSLRAED TAVYYC                           96

SEQ ID NO: 64           moltype = AA  length = 96
FEATURE                 Location/Qualifiers
source                  1..96
                        mol_type = protein
                        organism = synthetic construct
SEQUENCE: 64
DVQLVESGGG LVQAGGSLSI SCAASGGSLS NYVLGWFRQA PGKEREFVAA INWRGDITIG  60
PPNVEGRFTI SRDNAKNTGY LQMNSLAPDD TAVYYC                           96

SEQ ID NO: 65           moltype = AA  length = 96
FEATURE                 Location/Qualifiers
source                  1..96
                        mol_type = protein
                        organism = synthetic construct
SEQUENCE: 65
DVQLVESGGG VVQPGGSLRL SCAASGRTVS SYAMGWFRQA PGKEREFVAG ISRSAERTYY  60
VDSLKGRFTI SRDNSKNTVY LQMNSLRPED TALYYC                           96

SEQ ID NO: 66           moltype = AA  length = 96
FEATURE                 Location/Qualifiers
source                  1..96
                        mol_type = protein
                        organism = synthetic construct
```

-continued

```
SEQUENCE: 66
DVQLVESGGG LVQPGGSLRL SCAASGRTVS SYAMGWFRQA PGKEREFVAG ISRSAERTYY  60
VDSLKGRFTI SRDNSKNTVY LQMNSLRPED TAVYYC                            96

SEQ ID NO: 67          moltype = AA  length = 96
FEATURE                Location/Qualifiers
source                 1..96
                       mol_type = protein
                       organism = synthetic construct
SEQUENCE: 67
EVQLVESGGG LVQPGGSLRL SCAASGFTFS DYWMYWVRQA PGKGLEWVSE INTNGLITKY  60
PDSVKGRFTI SRDNAKNTLY LQMNSLRPED TAVYYC                            96

SEQ ID NO: 68          moltype = AA  length = 96
FEATURE                Location/Qualifiers
source                 1..96
                       mol_type = protein
                       organism = synthetic construct
SEQUENCE: 68
EVQLVESGGG LVQPGNSLRL SCAASGFTFS SFGMSWVRQA PGKGLEWVSS ISGSGSDTLY  60
ADSVKGRFTI SRDNAKTTLY LQMNSLRPED TAVYYC                            96

SEQ ID NO: 69          moltype = AA  length = 96
FEATURE                Location/Qualifiers
source                 1..96
                       mol_type = protein
                       organism = synthetic construct
SEQUENCE: 69
DVQLVESGGG LVQPGGSLRL SCAASGRTFS SYVVGWFRQA PGKEREFIGA ISGSGESIYY  60
AVSEKGRFTI SRDNSKNTLY LQMNSLRPED TAVYYC                            96

SEQ ID NO: 70          moltype = AA  length = 94
FEATURE                Location/Qualifiers
source                 1..94
                       mol_type = protein
                       organism = synthetic construct
SEQUENCE: 70
EVQLVESGGG LVQPGGSLRL SCAASGRTYD AMGWLRQAPG KEREFVAAIS GSGDDTYYAD  60
SVKGRFTISR DNSKNTLYLQ MNSLRPEDTA VYYC                              94

SEQ ID NO: 71          moltype = AA  length = 96
FEATURE                Location/Qualifiers
source                 1..96
                       mol_type = protein
                       organism = synthetic construct
SEQUENCE: 71
EVQLVESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYC                            96

SEQ ID NO: 72          moltype = AA  length = 96
FEATURE                Location/Qualifiers
source                 1..96
                       mol_type = protein
                       organism = synthetic construct
SEQUENCE: 72
EVQLVESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYC                            96

SEQ ID NO: 73          moltype = AA  length = 96
FEATURE                Location/Qualifiers
source                 1..96
                       mol_type = protein
                       organism = synthetic construct
SEQUENCE: 73
EVQLVESGGG LVQPGGSLRL SCAASGRTFS YNPMGWFRQA PGKGRELVAA ISRTGGSTYY  60
PDSVEGRFTI SRDNAKRMVY LQMNSLRAED TAVYYC                            96

SEQ ID NO: 74          moltype = AA  length = 96
FEATURE                Location/Qualifiers
source                 1..96
                       mol_type = protein
                       organism = synthetic construct
SEQUENCE: 74
DVQLVESGGG VVQPGGSLRL SCAASGRTVS SYAMGWFRQA PGKEREFVAG ISRSAERTYY  60
VDSLKGRFTI SRDNSKNTVY LQMNSLRPED TALYYC                            96

SEQ ID NO: 75          moltype = AA  length = 96
FEATURE                Location/Qualifiers
```

-continued

```
source                  1..96
                        mol_type = protein
                        organism = synthetic construct
SEQUENCE: 75
DVQLVESGGG LVQPGGSLRL SCAASGRTVS SYAMGWFRQA PGKEREFVAG ISRSAERTYY  60
VDSLKGRFTI SRDNSKNTVY LQMNSLRPED TAVYYC                            96

SEQ ID NO: 76           moltype = AA  length = 96
FEATURE                 Location/Qualifiers
source                  1..96
                        mol_type = protein
                        organism = synthetic construct
SEQUENCE: 76
EVQLVESGGG LVQPGGSLRL SCAASGRTFS YNPMGWFRQA PGKGRELVAA ISRTGGSTYY  60
PDSVEGRFTI SRDNAKRMVY LQMNSLRAED TAVYYC                            96

SEQ ID NO: 77           moltype = AA  length = 95
FEATURE                 Location/Qualifiers
source                  1..95
                        mol_type = protein
                        organism = synthetic construct
SEQUENCE: 77
EVQLVESGGG LVQPGGSLRL SCAASGSVFK INVMAWYRQA PGKGRELVAG IISGGSTSYA  60
DSVKGRFTIS RDNAKNTLYL QMNSLRPEDT AVYYC                             95

SEQ ID NO: 78           moltype = DNA  length = 72
FEATURE                 Location/Qualifiers
source                  1..72
                        mol_type = other DNA
                        organism = synthetic construct
SEQUENCE: 78
agactctcct gtgcagcctc tagagaccat ggccagtaag gccggtctct atgggctggt  60
tccgccaggc tc                                                      72

SEQ ID NO: 79           moltype = DNA  length = 72
FEATURE                 Location/Qualifiers
source                  1..72
                        mol_type = other DNA
                        organism = synthetic construct
SEQUENCE: 79
tctgagagga cacgtcggag atctctggta ccggtcattc cggccagaga tacccgacca  60
aggcggtccg ag                                                      72

SEQ ID NO: 80           moltype = AA  length = 22
FEATURE                 Location/Qualifiers
source                  1..22
                        mol_type = protein
                        organism = synthetic construct
SEQUENCE: 80
RLSCAASRDH GQGRSMGWFR QA                                           22

SEQ ID NO: 81           moltype = AA  length = 12
FEATURE                 Location/Qualifiers
source                  1..12
                        mol_type = protein
                        organism = synthetic construct
SEQUENCE: 81
AKDRYSSYYF DY                                                      12

SEQ ID NO: 82           moltype = AA  length = 12
FEATURE                 Location/Qualifiers
source                  1..12
                        mol_type = protein
                        organism = synthetic construct
SEQUENCE: 82
ARDRSSWYYF DY                                                      12

SEQ ID NO: 83           moltype = AA  length = 12
FEATURE                 Location/Qualifiers
source                  1..12
                        mol_type = protein
                        organism = synthetic construct
SEQUENCE: 83
ARDSSGWYNF DY                                                      12

SEQ ID NO: 84           moltype = AA  length = 12
FEATURE                 Location/Qualifiers
```

-continued

```
source                 1..12
                       mol_type = protein
                       organism = synthetic construct
SEQUENCE: 84
ARDSSSWHYF DY                                                      12

SEQ ID NO: 85          moltype = AA  length = 12
FEATURE                Location/Qualifiers
source                 1..12
                       mol_type = protein
                       organism = synthetic construct
SEQUENCE: 85
ARDSSSWYVF DY                                                      12

SEQ ID NO: 86          moltype = AA  length = 12
FEATURE                Location/Qualifiers
source                 1..12
                       mol_type = protein
                       organism = synthetic construct
SEQUENCE: 86
AREDSSWYYF DY                                                      12

SEQ ID NO: 87          moltype = AA  length = 13
FEATURE                Location/Qualifiers
source                 1..13
                       mol_type = protein
                       organism = synthetic construct
SEQUENCE: 87
ARRDKSGWYY FDY                                                     13

SEQ ID NO: 88          moltype = AA  length = 12
FEATURE                Location/Qualifiers
source                 1..12
                       mol_type = protein
                       organism = synthetic construct
SEQUENCE: 88
ARTSSGWYLF DY                                                      12

SEQ ID NO: 89          moltype = AA  length = 12
FEATURE                Location/Qualifiers
source                 1..12
                       mol_type = protein
                       organism = synthetic construct
SEQUENCE: 89
ATDSSGWYYF DY                                                      12

SEQ ID NO: 90          moltype = AA  length = 15
FEATURE                Location/Qualifiers
source                 1..15
                       mol_type = protein
                       organism = synthetic construct
SEQUENCE: 90
ARDLSSGWYR DAFDI                                                   15

SEQ ID NO: 91          moltype = AA  length = 16
FEATURE                Location/Qualifiers
source                 1..16
                       mol_type = protein
                       organism = synthetic construct
SEQUENCE: 91
ARDRYYGSGS YDAFDI                                                  16

SEQ ID NO: 92          moltype = AA  length = 15
FEATURE                Location/Qualifiers
source                 1..15
                       mol_type = protein
                       organism = synthetic construct
SEQUENCE: 92
AREGYSSGWS DAFDI                                                   15

SEQ ID NO: 93          moltype = AA  length = 16
FEATURE                Location/Qualifiers
source                 1..16
                       mol_type = protein
                       organism = synthetic construct
SEQUENCE: 93
ARGRDFWSGY YDAFDI                                                  16

SEQ ID NO: 94          moltype = AA  length = 15
```

-continued

```
FEATURE                Location/Qualifiers
source                 1..15
                       mol_type = protein
                       organism = synthetic construct
SEQUENCE: 94
ARGRYSSGWF DAFDI                                           15

SEQ ID NO: 95          moltype = AA  length = 15
FEATURE                Location/Qualifiers
source                 1..15
                       mol_type = protein
                       organism = synthetic construct
SEQUENCE: 95
ARLRYSGSYL DAFDI                                           15

SEQ ID NO: 96          moltype = AA  length = 15
FEATURE                Location/Qualifiers
source                 1..15
                       mol_type = protein
                       organism = synthetic construct
SEQUENCE: 96
ARPLYSGSYQ PAFDI                                           15

SEQ ID NO: 97          moltype = AA  length = 15
FEATURE                Location/Qualifiers
source                 1..15
                       mol_type = protein
                       organism = synthetic construct
SEQUENCE: 97
ARPRYSSNYY DAFDI                                           15

SEQ ID NO: 98          moltype = AA  length = 15
FEATURE                Location/Qualifiers
source                 1..15
                       mol_type = protein
                       organism = synthetic construct
SEQUENCE: 98
ARQRSSGWYW DAFDI                                           15

SEQ ID NO: 99          moltype = AA  length = 15
FEATURE                Location/Qualifiers
source                 1..15
                       mol_type = protein
                       organism = synthetic construct
SEQUENCE: 99
ARQVHSSGWY DAFDI                                           15

SEQ ID NO: 100         moltype = AA  length = 15
FEATURE                Location/Qualifiers
source                 1..15
                       mol_type = protein
                       organism = synthetic construct
SEQUENCE: 100
ARRFDSGSYF DAFDI                                           15

SEQ ID NO: 101         moltype = AA  length = 16
FEATURE                Location/Qualifiers
source                 1..16
                       mol_type = protein
                       organism = synthetic construct
SEQUENCE: 101
ARRGYSSGWY KDAFDI                                          16

SEQ ID NO: 102         moltype = AA  length = 15
FEATURE                Location/Qualifiers
source                 1..15
                       mol_type = protein
                       organism = synthetic construct
SEQUENCE: 102
ARVRYSSGWY DAFDI                                           15
```